(12) United States Patent  (10) Patent No.: US 9,969,758 B2
Anderson et al.  (45) Date of Patent: May 15, 2018

(54) ANTIMICROBIAL COMPOUNDS

(71) Applicant: BIOMERIEUX, Marcy-l'Etoile (FR)

(72) Inventors: Rosaleen Joy Anderson, Sunderland Tyne and Wear (GB); Alexandre F. Bedernjak, Morthomiers (FR); Marie Cellier, Montalieu-Verceu (FR); Keng Tiong Ng, Kuala Lumpur (MY); Sylvain Orenga, Neuville-sur-Ain (FR); John D. Perry, Tyne and Wear (GB); Linda Varadi, Sajovamos (HU)

(73) Assignee: Biomerieux, Marcy-l'Etolle (FR)

( * ) Notice: Subject to any disclaimer, the term of this patent is extended or adjusted under 35 U.S.C. 154(b) by 0 days. days.

(21) Appl. No.: 15/127,564

(22) PCT Filed: Mar. 23, 2015

(86) PCT No.: PCT/FR2015/050727
§ 371 (c)(1),
(2) Date: Sep. 20, 2016

(87) PCT Pub. No.: WO2015/140481
PCT Pub. Date: Sep. 24, 2015

(65) Prior Publication Data
US 2017/0158720 A1  Jun. 8, 2017

(30) Foreign Application Priority Data
Mar. 21, 2014 (FR) ...................... 14 52424

(51) Int. Cl.
C12Q 1/04 (2006.01)
C07F 9/38 (2006.01)
C12Q 1/06 (2006.01)
C12Q 1/18 (2006.01)

(52) U.S. Cl.
CPC ............. *C07F 9/3886* (2013.01); *C12Q 1/04* (2013.01); *C12Q 1/06* (2013.01); *C12Q 1/18* (2013.01)

(58) Field of Classification Search
CPC ................................ C07F 9/3886; C12Q 1/04
See application file for complete search history.

(56) References Cited

FOREIGN PATENT DOCUMENTS

| EP | 1325024 | 7/2003 |
|---|---|---|
| WO | 2002/22785 | 3/2002 |
| WO | 2002/24725 A1 | 3/2002 |
| WO | 2010/128120 A1 | 11/2010 |

OTHER PUBLICATIONS

Atherton, F.R., et al., "Synthesis and Structure-Activity Relationships of Antibacterial Phosphonopeptides", Journal of Medicinal Chemistry, American Chemical Society (1986), vol. 29, No. 1, pp. 29-40.
Hahn, F.E., "Alafosfalin, A New Synthetic Antibacterial Compound", Naturwissenschaften (1981), vol. 68, No. 2, p. 90.
Cheung, K.S., et al., "Chloroalanyl Antibiotic Peptides: Antagonism of Their Antimicrobial Effects by L-Alanine and L-Alanyl Peptides in Gram-Negative Bacteria", Journal of Medicinal Chemistry, (1986), pp. 2060-2068.
International Search Report for PCT/FR2015/050727, dated Jul. 13, 2015.
Written Opinion of the International Searching Authority dated Sep. 29, 2016 (including English translation) for PCT/FR2015/050727.
Atherton, F.R., et al., "Synthesis and Structure-Activity Relationships of Antibacterial Phosphonopeptides incorporating (1-Aminoethyl)phosphonic Acid and (Aminomethyl)phosphonic Acid", Journal of Medical Chemistry (1986), vol. 29, No. 1, pp. 29-40.
Atherton, F.R., et al., "Phosphonopeptides as Antibacterial Agents: Rationale, Chemistry, and Structure-Activity Relationships", Antimicrobial Agents and Chemotherapy, (May 1979), pp. 677-683.
Andrews, J.M., "Determination of Minimum Inhibitory Concentrations", Journal of Antimicrobial Chemotherapy, vol. 48, Supplement 1 (Jul. 2001), pp. 5-16.
Arfin, S.M., et al., "Inhibition of Growth of *Salmonella typhimurium* and of Threonine Deaminase and Transaminase B by b-Chloroalanine", Journal of Bacteriology, vol. 105, No. 2 (Feb. 1971), pp. 519-522.
Boduszek, B., et al., "ChemInform Abstract: Application of Silicon-Phosphorous Based Reagents in Synthesis of Aminophosphonates", Polish J. Chem., vol. 76 (2002), pp. 1105-1111.
Cheung, K-S., et al. "Chloroalanyl and Propargylglycyl Dipeptides. Suicide Substrate Containing Antibacterials", J. Med. Chem. (1983), vol. 26, pp. 1733-1741.
Gibson, M.M., et al., "Genetic Characterization and Molecular Cloning of the Tripeptide Permease (tpp) Genes of *Salmonella typhimurium*", Journal of Bacteriology, vol. 160, No. 1 (Oct. 1984), pp. 122-130.
Kametani, T., et al., "Studies on the Synthesis of Chemotherapeutics, Part XIII. Synthesis and Biological Studies on Phosphonopeptides having Alykl-, Phenyl-, and heterocyclic Substituents", Heterocycles, vol. 18 (1982), p. 295-319.
Kudzin, Z.H., et al., "Synthesis of 1-Aminoalkanephosphonates via Thioureidoalkanephosphonates", Communications, (Jun. 1978), pp. 469-472.
Kudzin, Z.H., et al., "A Facile Conversation of Aminoalkanephosphonic Acids Into O,O-Dialkyl N-Acylaminoalkanephosphonate Derivatives", Synthesis (May 1995), pp. 509-511.
Lavielle, S., et al., "Synthesis of a Glycotripeptide and a Glycosomatostatin Containing the 3-O-(2-Acetamido-2-Deoxy-B-D-Glucopyranosyl)-L-Serine Residue", Carbohydrate Research, vol. 89 (1981), pp. 229-236.

(Continued)

*Primary Examiner* — Golam M M Shameem
(74) *Attorney, Agent, or Firm* — Brinks Gilson & Lione

(57) ABSTRACT

An antimicrobial compound, as well as the salts, derivatives and analogs thereof, said compound being represented by the general formula (I):

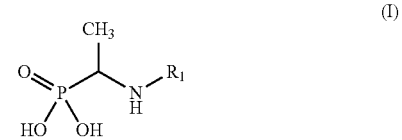

(I)

Figure 1:
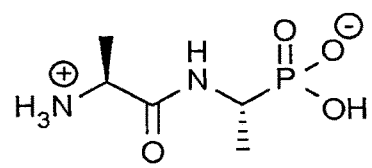
Figure 1:
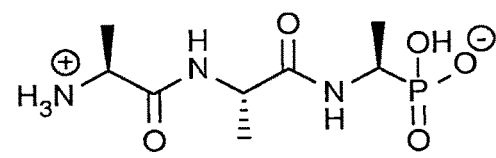
Figure 1:
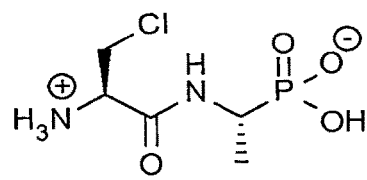
Figure 1:
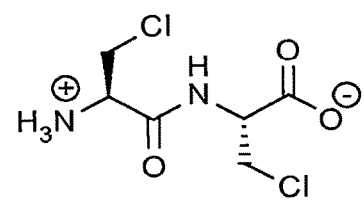
Figure 1:
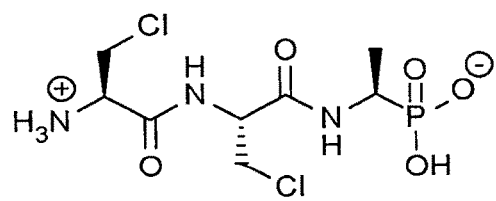
Figure 1:
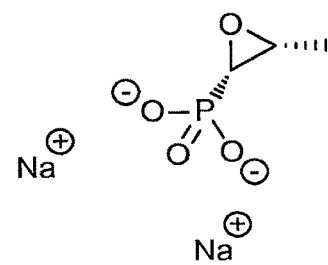

wherein $R_1$ represents a peptide part P1 or a peptide part P2.

44 Claims, 7 Drawing Sheets

(56) References Cited

OTHER PUBLICATIONS

Nakata, T., et al., "Peptide Synthesis in Aqueous Solution. V. Properties and Reactivities of (p-Hydroxyphenyl)benzylmethylsulfonium Salts for Direct Benzyl Esterification of N-Acylpeptides", Bull. Chem. Soc. Jpn., vol. 69 (1996), pp. 1099-1106.

Rao, J., et al., "Design, Synthesis, and Characterization of a High-Affinity Trivalent System Derived from Vancomycin and L-Lys-D-Ala-D-Ala", J. Am. Chem. Soc., vol. 122 (2000), pp. 2698-2710.

Varadi, L., et al., "Synthesis and Evaluation of Fluorogenic 2-amino-1, 8-naphthyridine Derivatives for the Detection of Bacteria", Organic and Biomolecular Chemistry, Org. Biomol. Chem., vol. 10 (2012), pp. 2578.

Yuan, C., et al., "Enzymatic Synthesis of Optically Active 1- and 2-aminoalkanephosphonates", Tetrahedron, vol. 59 (2003), pp. 6095-6102.

Cheung, K.S., et al., "Chloroalanyl Antibiotic Peptides: Antagonism of Their Antimicrobial Effects by L-Alanine and L-Alanyl Peptides in Gram-Negative Bacteria", J. Med. Chem., vol. 29 (1986), pp. 2060-2068.

Orenga, S., et al., "Enzymatic Substrates in Microbiology", Journal of Microbiological Methods, vol. 79 (2009), pp. 139-155.

A

B

C

D

E

F

G

H

I

J

ANTIMICROBIAL COMPOUNDS

This application is a National Stage application of International Application No. PCT/FR2015/050727 filed Mar. 23, 2015. This application also claims priority under 35 U.S.C. § 119 to FR Patent Application No. 1452424, filed Mar. 21, 2014.

TECHNICAL FIELD

The present invention concerns new antimicrobial compounds, new reaction media comprising them, and their uses. In particular, the new compounds according to the invention are proving to be effective against microorganisms which are multi-resistant to antimicrobials, and notably against bacteria multi-resistant to conventional antibacterials.

STATE OF THE ART

The increase in microorganisms presenting multiple resistance to classic antimicrobial agents (for example to antibacterials) regularly requires development of new antimicrobial agents endowed with a new type of modes of action. A worrying lack of new antimicrobials, notably with regard to treatment of multi-resistant gram-negative bacteria, such as those producing carbapenemases, is proving of particular concern. What is more, these multi-resistant microorganisms are capable of giving rise to erroneous diagnostics, generating false-positive results if said multi-resistant microorganisms are present in reaction media which are referred to as specific to other microorganisms, thereby inducing major problems in terms of detection specificity.

Microbiological diagnostic techniques are still based largely on culturing steps to isolate the microorganisms of interest. If they are used to seek pathogens potentially present in small quantities within an abundant commensal microbial flora, it is necessary to use selective culture media. These media are based notably on using specific inhibitors acting on the main commensal flora species without inhibiting growth of the pathogens sought.

In the late 1970s, "mimetic peptides" were developed for their antibacterial properties. These typically consisted of an "active" antibacterial part bound covalently to one or more amino acid(s) intended to facilitate the absorption of these "mimetic peptides" by means of the microbial peptides transport system. Intracellular hydrolytic cleavage (due to an aminopeptidase activity) then released the active antibacterial part inside the bacteria of interest for interaction with its target. As a "mimetic peptide", mention may be made of alafosfalin (L-alanyl-L-1-aminoethylphosphonic acid; CAS number: 60668-24-8), developed by Roche in the late 1970s. Bacterial absorption of alafosfalin is described in the literature as being performed by means of LL-dipeptide permeases. Once inside the target bacteria, the active antibacterial part, in this case fosfalin (L-1-aminoethylphosphonic acid), is hydrolysed (more accurately "released" from the alanine residue by hydrolysis of the peptide bond joining it to said alanine residue), and then binds to the alanine racemase, thereby preventing synthesis of D-alanine, an essential ingredient for biosynthesis of peptidoglycan [1]. Alafosfalin has been described as possessing a broad spectrum of antibacterial activity Pt both in vitro and in vivo, against certain aerobic Gram-positive microorganisms (*Staphylococcus aureus*, *Enterococcus faecalis*, but neither Group A streptococci nor Group B streptococci such as *S. agalactiae*, nor *Streptococcus pneumoniae*), anaerobic bacteria (*Bacteroides* sp. and *Clostridium perfringens*, but not *Clostridium difficile*) and numerous Gram-negative bacilli species, but not *Pseudomonas* or *Acinetobacter*.

Use of alafosfalin was also described in patent application WO 02/22785 and in patent EP-B-1325024 as a selective agent for development of a selective culture medium enabling the isolation of microorganisms belonging to the *Salmonella* spp family.

However, in 1984, Gibson et al. 131 disclosed the fact that alafosfalin proved to be inactive against numerous bacterial strains because of the high frequency of the resistant strains.

Other synthetic antibacterials developed in the 1980s used a similar administration method and/or mode of action. For example, Cheung et al. 141 studied the antibacterial activity of several halogenated dipeptides, including L-β-chloroalanyl-L-β-chloroalanine. The β-chloroalanine, released by hydrolysis, appears to interact with certain enzyme systems, including alanine racemase, and also appears to present a broad spectrum of antibacterial activity [5]. Within the framework of an attempt to optimise the substrates of Cheung et al. [4], the β-Cl-L-Alanine (β-Cl-L-Ala) residue was incorporated into various di- and tripeptides [5]. However, not only did none of the peptides thus obtained make it possible to significantly improve the antibacterial activity of the compound L-β-chloroalanyl-L-β-chloroalanine, but the authors of this publication concluded that di- and tripeptides comprising an L-alanyl residue were devoid of antibacterial activity, notably with regard to Gram-negative microorganisms. The authors of this publication deduced from this that the absence of antibacterial activity observed with regard to di- and tri-peptide residues comprising an L-alanyl residue could be correlated with the property of L-alanine to protect the alanine racemase in Gram-negative bacteria against β-Cl-L-Ala residues. In other words, competition seems to occur between β-Cl-L-Ala residue and L-alanyl residue in relation to alanine racemase.

Also with a view to optimisation, Atherton et al. [6] attempted to combine, in the same molecule, alafosfalin on the one hand, and β-chloro-L-alanine (β-Cl-L-ala), on the other. However, this attempt ended in failure, insofar as this hybrid molecule did not present any antibacterial activity, despite the known antibacterial properties of β-chloroalanine [7]. Atherton et al. concluded that this result was due to the inability of L,L dipeptide permeases to effectively transport this compound within bacteria.

At a time when resistance to classic/conventional antimicrobials is increasing, one objective therefore consists in developing new antimicrobial compounds, both with regard to human or animal treatment, and with regard to in vitro diagnosis employing these new antimicrobial agents as selective agents. This task is made all the tougher since, as indicated previously (cf. publications [5] and [6]), the modifications and other combinations of existing antimicrobial compounds are likely to bring about a decrease in—or even complete loss of—their antimicrobial activity.

Statement of the Invention

The Applicant has discovered, surprisingly, that the aforementioned objective was achieved by compounds of general formula (I):

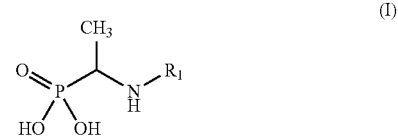

as well as salt(s), derivative(s) and analogue(s) thereof, preferably their salt(s)

wherein $R_1$ represents:
- a peptide part P1 consisting in a linear sequence of one to five amino acid residues; said peptide part P1 comprising at least one β-chloroalanine residue, preferably β-chloro-L-alanine, or
- a peptide part P2, said peptide part P2 being represented by the following general formula (II):

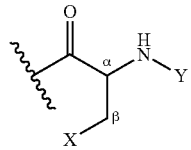

(II)

wherein X represents a hydrogen or chlorine atom, and Y represents a hydrogen atom or a linear sequence of one to four amino acid residues, advantageously comprising at least one β-chloroalanine residue, preferably β-chloro-L-alanine, and/or at least one norvaline residue, preferably L-norvaline, and/or at least one methionine residue, preferably L-methionine, and wherein if X represents a hydrogen atom, Y is as defined previously with the exception of a hydrogen atom or an alanine residue, whether this alanine residue is in the N-terminal position ("at the chain end") or it is bound to another amino acid residue via a peptide bond (between the α amino function of said alanine residue and the α carboxylic acid function of the other amino acid residue).

Of course, as the terminology used indicates, and in particular the expression "peptide part", a linear sequence consisting of a plurality of amino acid residues means that the plurality of amino acid residues are bound together via peptide bonds. As is well known in biochemistry, a peptide bond is a covalent bond which is formed between the carboxyl function carried by the α carbon of an amino acid ("α carboxyl function") and the amino function carried by the α carbon of the next amino acid in the peptide chain ("α amino function"). This peptide bond corresponds to an amide function.

Preferably, $R_1$ is represented by the general formula (III):

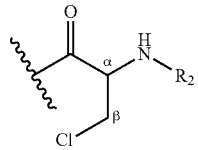

(III)

wherein $R_2$ is a hydrogen atom or a linear sequence of one to four amino acid residues, advantageously comprising at least one β-chloroalanine residue, preferably β-chloro-L-alanine, and/or at least one norvaline residue, preferably L-norvaline, and/or at least one methionine residue, preferably L-methionine.

By definition, if $R_2$ is a hydrogen atom, $R_1$ is a peptide part including a single amino acid residue, namely a β-chloroalanine residue, preferably β-chloro-L-alanine.

As indicated previously, and according to a preferred embodiment, if $R_2$ is a linear sequence of one to four amino acid residues, this comprises at least one β-chloroalanine residue (preferably β-chloro-L-alanine), and/or at least one norvaline residue (preferably L-norvaline), and/or at least one methionine residue (preferably L-methionine). Advantageously, the abovementioned β-chloroalanine residue (preferably β-chloro-L-alanine), norvaline residue (preferably L-norvaline) or methionine residue (preferably L-methionine) is directly bound via a peptide bond to the β-chloro-L-alanine residue represented in general formula (III) (said peptide bond being formed between the α carboxylic acid function of said β-chloroalanine, norvaline or methionine residue and the amino function represented in general formula (III)).

According to a particular embodiment, $R_2$ consists in a norvaline residue, preferably L-norvaline or a methionine residue, preferably L-methionine.

According to a preferred embodiment, $R_1$ is represented by the general formula (IV):

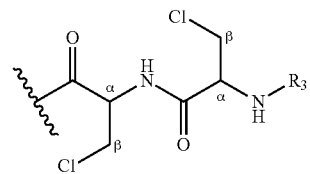

(IV)

wherein $R_3$ is a hydrogen atom or a linear sequence of one to three amino acid residues, advantageously comprising at least one β-chloroalanine residue, preferably β-chloro-L-alanine.

In accordance with the notation conventions in force in chemistry (notably in terms of topological formulae), the so-called "wave" or "zigzag" symbol, represented on formulae (II), (III) and (IV) above, is used to depict the bond between the $R_1$ group and the rest of the compound of general formula (I) (via the formation of a peptide bond).

By definition, if $R_3$ is a hydrogen atom, $R_1$ is a peptide part including only two identical amino acid residues, namely two β-chloroalanine residues, preferably β-chloro-L-alanine, bound to each other via a peptide bond. The unit formed in this way is denoted "β-chloroalanyl-β-chloroalanine".

According to a particular embodiment, $R_3$ comprises a norvaline residue, preferably L-norvaline, or a methionine residue, preferably L-methionine. Advantageously, said norvaline residue (preferably L-norvaline) or methionine residue (preferably L-methionine) is directly bound via a peptide bond (between the α carboxylic acid function of said norvaline or methionine residue and the amino function NH—$R_3$ of the β-chloroalanyl-β-chloroalanine residue represented in general formula (IV)) to the β-chloroalanyl-β-chloroalanine residue (preferably to the β-chloro-L-alanyl-β-chloro-L-alanine residue) represented in general formula (IV). As is well known to the person skilled in the art, the formation of this peptide bond is obtained by a condensation reaction between the primary amino function of the β-chloroalanyl-β-chloroalanine unit (preferably β-chloro-L-alanyl-β-chloro-L-alanine) and the carboxylic acid function of norvaline (preferably L-norvaline) or of methionine (preferably L-methionine), in order to form a peptide bond between said β-chloroalanyl-β-chloroalanine unit and said norvaline (preferably L-norvaline) or said methionine (preferably L-methionine). According to a particular embodiment, $R_3$ consists in a norvaline residue, preferably L-norvaline, or a methionine residue, preferably L-methionine.

Preferably, said peptide part $R_1$ of the compound of general formula (I) consists in a linear chain of two to three, preferably two, amino acid residues; these amino acid residues being bound together via peptide bonds, as explained previously.

Generally speaking, said amino acid residue(s) is/are selected from glycine, sarcosine and the L and D forms, preferably L, of the residues of β-chloroalanine, alanine, arginine, asparagine, aspartic acid, cysteine, glutamic acid, gamma-glutamic acid, glutamine, histidine, isoleucine, leucine, lysine, methionine, norvaline, phenylalanine, proline, pyroglutamic acid, serine, threonine, tryptophan, tyrosine and valine. Advantageously, said amino acid residue(s) is/are selected from the L and D forms, preferably L, of the residues of β-chloroalanine, alanine, methionine, norvaline and valine.

According to another embodiment, the antimicrobial compound according to the invention is defined by the aforementioned general formula (I), wherein $R_1$ represents said peptide part P2 and wherein X represents a hydrogen atom. Advantageously, in this other embodiment, Y is an amino acid residue selected from glycine, sarcosine, the L and D forms, preferably L, of the residues of β-chloroalanine, arginine, asparagine, aspartic acid, cysteine, glutamic acid, gamma-glutamic acid, glutamine, histidine, isoleucine, leucine, lysine, methionine, norvaline, phenylalanine, proline, pyroglutamic acid, serine, threonine, tryptophan, tyrosine and valine; advantageously Y is an amino acid residue selected from the L and D forms, preferably L, of residues of methionine and norvaline.

According to a particularly preferred embodiment, the antimicrobial compound according to the invention consists in:
  β-chloro-L-alanyl-D/L-1-aminoethylphosphonic acid, preferably β-chloro-L-alanyl-L-1-aminoethylphosphonic acid, and/or
  β-chloro-L-alanyl-β-chloro-L-alanyl-D/L-1-aminoethylphosphonic acid, preferably β-chloro-L-alanyl-β-chloro-L-alanyl-L-1-aminoethylphosphonic acid, and/or
  L-norvalinyl-β-chloro-L-alanyl-D/L-1-aminoethylphosphonic acid, preferably L-norvalinyl-β-chloro-L-alanyl-L-1-aminoethylphosphonic acid, and/or
  L-methionyl-β-chloro-L-alanyl-D/L-1-aminoethylphosphonic acid, preferably L-methionyl-β-chloro-L-alanyl-L-1-aminoethylphosphonic acid, and/or
  L-norvalinyl-L-alanyl-D/L-1-aminoethylphosphonic acid, preferably L-norvalinyl-L-alanyl-L-1-aminoethylphosphonic acid, and/or
  L-methionyl-L-alanyl-D/L-1-aminoethylphosphonic acid, preferably L-methionyl-L-alanyl-L-1-aminoethylphosphonic acid;
  advantageously said antimicrobial compound consisting in β-chloro-L-alanyl-D/L-1-aminoethylphosphonic acid, preferably β-chloro-L-alanyl-L-1-aminoethylphosphonic acid, and/or
  β-chloro-L-alanyl-β-chloro-L-alanyl-D/L-1-aminoethylphosphonic acid, preferably β-chloro-L-alanyl-β-chloro-L-alanyl-L-1-aminoethylphosphonic acid.

Advantageously, the antimicrobial compound according to the invention consists in β-chloro-L-alanyl-D/L-1-aminoethylphosphonic acid, preferably β-chloro-L-alanyl-L-1-aminoethylphosphonic acid, and/or β-chloro-L-alanyl-β-chloro-L-alanyl-D/L-1-aminoethylphosphonic acid, preferably β-chloro-L-alanyl-β-chloro-L-alanyl-L-1-aminoethylphosphonic acid, or a mixture of both.

According to a preferred embodiment of the invention, the N-terminal amino function of the antimicrobial compound according to the invention is protected by a protecting group such as a tertiobutylocarbonyl, 9-fluorenylmethoxycarbonyl or benzyloxycarbonyl group.

The present invention also concerns a reaction medium comprising at least one antimicrobial compound as defined previously, said compound being present in a final concentration of between 0.002 and 1024.0 mg/L, preferably between 0.003 and 32.0 mg/L, advantageously between 0.2 and 8.0 mg/L, preferably between 0.2 and 2.0 mg/L.

According to a preferred embodiment, said reaction medium is a medium making it possible to detect and/or identify and/or count at least one target microorganism, preferably at least one target bacterium, in a sample capable of containing it, such as a sample of industrial origin or of clinical origin, wherein said at least one compound is at least one selective agent making it possible to inhibit the survival and/or growth of non-target microorganism(s) so as to favour the survival and/or growth of said at least one target microorganism.

Advantageously, said reaction medium is a culture medium comprising at least one nutrient enabling the growth of said at least one target microorganism, wherein said at least one selective agent makes it possible to inhibit the growth of non-target microorganism(s) so as to favour the growth of said at least one target microorganism.

Preferably, said reaction medium comprises, moreover, an enzyme substrate specific to an enzymatic activity of said at least one target microorganism.

Preferably, said reaction medium comprises at least one selective agent consisting in:
  β-chloro-L-alanyl-L-1-aminoethylphosphonic acid, preferably at a final concentration of between 0.002 and 1024.0 mg/L, preferably between 0.003 and 32.0 mg/L, advantageously between 0.2 and 8.0 mg/L, preferably between 0.2 and 2.0 mg/L, or
  β-chloro-L-alanyl-β-chloro-L-alanyl-L-1-aminoethylphosphonic acid, preferably at a final concentration of between 0.002 and 1024.0 mg/L, preferably between 0.003 and 32.0 mg/L, advantageously between 0.2 and 8.0 mg/L, preferably between 0.2 and 2.0 mg/L, or
  a mixture of both.

According to an advantageous embodiment, said reaction medium makes it possible to detect and/or identify and/or count at least one target microorganism (microorganism of interest), said at least one target microorganism being:
  at least one Gram-negative target microorganism belonging to the genus *Salmonella*, for example belonging to the species *Salmonella enterica*, to the serotype *Salmonella Typhimurium* or to the serotype *Salmonella Enteridis*, to the genus *Acinetobacter*, for example to the species *Acinetobacter baumannii*, to the genus *Burkholderia*, for example to the species *Burkholderia cepacia*, to the genus *Pseudomonas*, for example to the species *Pseudomonas aeruginosa*; advantageously said at least one Gram-negative target microorganism belonging to the genus *Salmonella*; or
  at least one Gram-positive target microorganism, belonging to the genus *Listeria*, for example belonging to the species *Listeria monocytogenes*, or to the genus *Streptococcus*, for example *Streptococcus agalactiae* and/or *Streptococcus pneumoniae* and/or *Streptococcus pyogenes*; advantageously said at least one Gram-positive target microorganism belonging to the genus *Listeria*.

According to an advantageous embodiment, said reaction medium makes it possible to detect and/or identify and/or count at least one target microorganism belonging to the genus *Salmonella*.

According to a particularly advantageous embodiment, said reaction medium makes it possible to detect and/or identify and/or count at least one target microorganism belonging to the genus *Salmonella*, said medium comprising:
- at least one nutrient agent, such as peptones, for example of porcine or bovine origin, at a concentration of between 0.2 and 30.0 g/L,
- possibly a buffer,
- at least one chromogenic marker, such as an esterase enzyme substrate and/or an alpha-galactosidase enzyme substrate, at a concentration of between 0.05 and 15.0 g/L,
- agar at a concentration of between 9.0 and 28.0 g/L, and
- at least one selective agent as defined in one of claims 12 to 16, preferably at a concentration of between 0.002 and 1024.0 mg/L, preferably between 0.003 and 32.0 mg/L, advantageously between 0.2 and 8.0 mg/L, preferably between 0.2 and 2.0 mg/L.

Advantageously, said reaction medium comprises a mixture of at least one esterase enzyme substrate and/or at least one alpha-galactosidase enzyme substrate. It may moreover comprise a glucosidase enzyme substrate (advantageously of β-glucosidase) and/or a galactosidase enzyme substrate. According to a preferred embodiment, said reaction medium comprises at least one esterase enzyme substrate or at least one alpha-galactosidase enzyme substrate, in association with at least one β-glucosidase enzyme substrate. According to a particularly preferred embodiment, said reaction medium comprises at least one esterase enzyme substrate in association with one β-glucosidase enzyme substrate.

An example of this type of reaction medium is illustrated below in table 2 (cf. example 3.1 below).

Preferably, said non-target microorganisms is/are within the group consisting of:
- genera of the Enterobacteriaceae family, such as the genus *Enterobacter* (for example *Enterobacter cloacae*) and/or the genus *Escherichia* (for example *Escherichia Coli*) and/or the genus *Klebsiella* (for example *Klebsiella pneumoniae*) and/or the genus *Serratia* (for example *Serratia marcescens*) and/or the genus *Yersinia* (for example *Yersinia enterocolitica*), and/or
- the genus *Enterococcus* (for example *Enterococcus faecalis* and/or *Enterococcus faecium*), and/or
- the genus *Staphylococcus* (for example *Staphylococcus epidermidis* and/or *Staphylococcus aureus*)
- preferably the non-target microorganism(s) is/are resistant to at least one conventional antibacterial.

Bacteria of the Enterobacteriaceae family (enterobacteria), such as for example *E. coli*, are Gram-negative bacteria frequently encountered in biological samples, including in mixture with Gram-negative target bacteria, such as bacteria from the genus *Salmonella*. These enterobacteria grow readily on the culture medium and thus may mask said Gram-negative target bacteria (also known as Gram-negative bacteria of interest). Insofar as the antimicrobial compounds according to the present invention inhibit, selectively and at low concentration, certain enterobacteria relative to Gram-negative target bacteria (such as bacteria of the genus *Salmonella*), said antimicrobial agents according to the invention are particularly suitable for preparing reaction media intended for detecting and/or identifying and/or counting Gram-negative target bacteria such as bacteria of the genus *Salmonella*. From the above it results that the antimicrobial compounds according to the invention are particularly recommended for preparing reaction media aimed at detecting and/or identifying and/or counting bacteria of the genus *Salmonella*.

Furthermore, enterococci and notably those belonging to the species *Enterococcus faecalis* are Gram-positive bacteria frequently encountered in biological samples, including in mixture with other Gram-positive bacteria. These enterococci grow readily on/in the culture media, and may consequently mask Gram-positive target bacteria (Gram-positive bacteria of interest) such as bacteria of the genus *Listeria* (for example belonging to the species *Listeria monocytogenes*), bacteria of the species *Staphylococcus aureus*, bacteria of the genus *Streptococcus* (including *Streptococcus agalactiae, Streptococcus pneumoniae* or *Streptococcus pyogenes*). Insofar as the antimicrobial compounds according to the invention inhibit, selectively and at low concentration, the abovementioned enterococci relative to Gram-positive target bacteria (such as bacteria of the genus *Listeria*), said antimicrobial compounds according to the invention are particularly appropriate for preparing reaction media intended for detecting and/or identifying and/or counting Gram-positive target bacteria, such as those mentioned above.

Another object of the invention concerns the in vitro use of a reaction medium to detect and/or identify and/or count at least one target microorganism, preferably at least one target bacterium, in a sample capable of containing it, such as a sample of industrial origin or of clinical origin.

Another object of the invention concerns a method of detecting and/or identifying and/or counting at least one target microorganism, preferably at least one target bacterium, in a sample capable of containing it, such as a sample of industrial origin or of clinical origin, said method comprising the following steps:
a) seeding the reaction medium as defined previously with said sample,
b) if necessary incubating the assembly for a sufficient period of time to enable detection and/or identification and/or counting of at least one target microorganism,
c) identifying the colonies formed by said at least one target microorganism.

The invention also concerns the antimicrobial compound, as defined above, for its use as a medication for human or veterinary use.

Another object of the invention concerns the use of the compound as defined above for its use as a medication in the treatment of microbial infections, preferably bacterial infections, for human or veterinary use.

According to a preferred embodiment, compounds of formula (I), as well as salts, derivatives and analogues thereof (in particular their salts), are particularly effective against bacteria presenting multiple resistance (also known as multi-resistant) to conventional antibiotics (notably to classic antibiotics), at concentrations varying from 0.002 to 1024.0 mg/L preferably from 0.003 to 32.0 mg/L, preferably from 0.2 to 8.0 mg/L, advantageously from 0.2 to 2.0 mg/L.

Thus, the present invention concerns new antimicrobial compounds, preferably antibacterial compounds (for example bactericidal antibiotics or bacteriostatic antibiotics), making it possible to treat microbial infections, preferably bacterial infections which are difficult to treat using conventional antibacterial agents such as classic antibiotics, namely those commonly used to treat said infections.

"Amino acid residue" is understood to mean, in the terms of the present invention, the rest of an amino acid of interest after it has established at least one peptide bond with at least one other amino acid. For example, if the aforementioned general formula (IV) is examined, it is apparent that the molecule represented by the general formula (III) is bound to a β-chloroalanine residue, itself bound to the substituent R₃; said β-chloroalanine residue per se therefore having the following formula:

i)

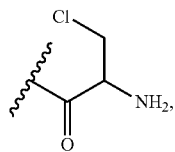 [SMILES: *C(=O)C(N)CCl]

if R₃ is a hydrogen atom, or ii)

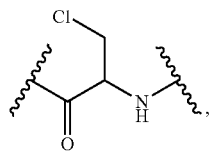 [SMILES: *NC(CCl)C(*)=O]

if R₃ is a linear sequence (chain) of one to three amino acid residues; in which case said β-chloroalanine residue is bound to another amino acid residue due to the formation of a peptide bond between the α amino function of the β-chloroalanine residue and the α carboxylic acid function of the other amino acid residue.

Of course, the same rationale applies by analogy to the definition of the amino acid residues other than an alanine residue.

"Antimicrobial compound" is understood to mean a compound active against microorganisms, namely intended to combat the latter. According to a preferred embodiment, this antimicrobial compound is an antibacterial compound, namely active against bacteria (and intended to combat the latter). In terms of the present invention, the antibacterial compound may be a bactericidal antibiotic, namely which destroys bacteria or a bacteriostatic antibiotic, namely which blocks bacterial growth; in other words which prevents bacterial multiplication without necessarily killing them. It should be noted that an antibiotic may be bacteriostatic at low dose and bactericidal at a higher dose.

According to another embodiment, the "antimicrobial compound" may consist in an "antifungal" compound. "Antifungal compound" is understood to mean any compound capable of preventing or slowing the growth of a yeast or a mould. By way of indication, it is possible to mention notably amphotericin B, fluconazole, itraconazole, voriconazole and cycloheximide. Preferably, if at least one antifungal agent is used, the latter is used at concentrations known to the person skilled in the art to obtain the aforementioned effect.

"Reaction medium" is understood to mean a medium comprising all the elements necessary for the expression of metabolism and/or survival and/or growth of microorganisms. This reaction medium may either be used solely as a revealing medium, or be used as a culture and revealing medium. In the first case, the microorganisms may be cultured before seeding and, in the second case, the reaction medium also constitutes the culture medium. The reaction medium may be solid, semi-solid or liquid. "Semi-solid medium" is understood to mean a gelled medium, for example. Agar is the conventional gelling agent used in microbiology for culturing microorganisms, but it is possible to use other gelling agents such as for example gelrite, gelatine, agarose, as well as other natural or artificial gelling agents. A number of preparations are commercially available, for instance Columbia agar, Trypcase-soy agar, MacConkey agar, Mueller Hinton agar or more generally those described in the Handbook of Microbiological Media (CRC Press). The reaction medium according to the invention may moreover comprise possible additives such as for example amino acids, peptones (in an appropriate concentration known to the person skilled in the art so as not to risk cancelling out the inhibiting effect of the antimicrobial compounds which are the object of the present invention), one or more growth factors, carbohydrates, amino acids, nucleotides, minerals, vitamins, one or more selective agents, buffers, one or more gelling agents, etc. Said reaction medium may also comprise a dye. As an indication, possible dyes may be Evans blue, neutral red, sheep blood, horse blood, an opacifier such as titanium oxide, nitroaniline, malachite green, brilliant green, one or more metabolic indicators, one or more metabolic regulators, etc. This reaction medium may, for example, come in liquid form, namely ready-to-use gel, i.e. ready to be seeded in a tube, in a flask or on a Petri dish.

The person skilled in the art may also use a bi-plate, which makes it possible to easily compare two media, comprising different substrates or different selective mixtures, onto which the same biological sample will have been deposited. The reaction medium may comprise one or more selective agents.

"Selective agent" is understood to mean any compound capable of preventing or slowing the growth of a so-called "non-target" microorganism, namely one other than the target microorganism(s). Without being limiting, a concentration of between 0.002 and 1024.0 mg/L, preferably between 0.003 and 32.0 mg/L, advantageously between 0.2 and 8.0 mg/L, preferably between 0.2 and 2.0 mg/L, is particularly suitable for the present invention. Generally speaking, we recommend a selective agent concentration of between 0.01 mg/l and 5.0 g/l.

"Detection" is understood to mean detecting with the naked eye or using an optical apparatus the existence of a growth of the target microorganisms (preferably of the target bacteria). If the reaction medium from which it is desired to detect the target microorganisms comprises a chromogenic or fluorogenic substrate, the detection may be performed using an optical apparatus for fluorogenic substrates, or with the naked eye or using an optical apparatus for chromogenic substrates.

"Counting at least one target microorganism" is understood to mean recording/quantifying the number of target microorganisms, for example the number of bacterial colonies if the target microorganism is a bacterium.

"Sample" is understood to mean a small part or small isolated quantity of an entity for analysis. The sample may be of industrial origin, or, according to a non-exhaustive list, an air specimen, a water specimen, a specimen taken from a surface, a part or a manufactured product, or a food product. Amongst the samples of food origin, non-exhaustive mention may be made of a sample of dairy products (yogurts, cheeses, . . . ), meat, fish, egg, fruits, vegetables, water, beverages (milk, fruit juice, soda, etc.). These food samples may also come from sauces or ready meals. Finally, a food sample may come from an animal feed, such as animal or plant meals. The sample may be of biological origin, either animal, vegetable or human. In this case it may correspond to a specimen of biological fluid (whole blood, serum, plasma, urine, cerebrospinal fluid, organic secretion, stool, . . . ), an external specimen (skin, nose, throat, perineum, rectum, vagina, . . . ) or tissue specimen or isolated cells. This specimen may be used as-is or, prior to the analysis, undergo preparation by enrichment, extraction, concentration or purification, according to methods known to the person skilled in the art.

Microbiological control corresponds to analysing a sample for the purpose of detecting and/or counting microorganisms suspected/capable of being present within said sample.

As nutrients enabling growth of at least one target microorganism on the reaction medium or within the reaction medium according to the invention, mention may be made notably of amino acids, peptones (in an appropriate concentration known to the person skilled in the art so as not to risk cancelling out the inhibiting effect of the antimicrobial compounds which are the object of the present invention), carbohydrates, nucleotides, minerals and vitamins.

If the reaction medium according to the invention comprises moreover an enzyme substrate specific to an enzymatic activity of said at least one target microorganism, preferably a chromogenic and/or fluorogenic substrate is used.

"Chromogenic and/or fluorogenic substrate" is understood to mean a substrate making it possible to detect an enzymatic or metabolic activity of the target/sought microorganisms by means of a directly or indirectly detectable signal. For direct detection, this substrate may be bound to a part acting as a fluorescent or coloured marker [8]. For indirect detection, the reaction medium according to the invention may also contain a pH indicator, sensitive to the pH variation induced by the consumption of the substrate and revealing the metabolism of the target microorganisms. Said pH indicator may be a chromophore or a fluorophore. As examples of chromophores, mention may be made of bromocresol purple, bromothymol blue, neutral red, aniline blue and bromocresol blue.

The chromogenic enzyme substrates usable in the terms of the present invention may be of different natures.

Firstly, mention should be made of substrates based on indoxyl and its derivatives which, after hydrolysis and in the presence of oxygen, produce a precipitate varying from blue to pink. These substrates based on indoxyl and its derivatives are particularly preferred in terms of the present invention due to their relatively easy employment and their good sensitivity within the framework of detecting and/or counting bacteria. Their applications substantially relate to the osidase-, esterase-, lipase- and phosphatase-type enzymatic activities (phosphatase being an esterase activity of phosphoric acid). Being well suited to a use on a solid or semi-solid support (filter, agar, electrophoresis gel, etc.), they are less so to use in liquid medium (formation of a precipitate).

Certain Aldol®-type indoxyl derivatives represent enzyme substrates of interest in terms of the present invention, insofar as the appearance of a coloured precipitate does not require any addition (oxygen, metal salts, etc.). The use of such enzyme substrates may therefore prove particularly advantageous within the framework of pour seeding of bacteria. These Aldol®-type indoxyl derivatives are particular indoxyl derivatives (1H-indolyl-3-yl), namely indoxyl-based substrates joined onto the cyclic amine (N-arylated), as disclosed in the PCT application published under reference WO 2010/128120 (in the name of Biosynth® AG [CH]). These enzyme substrates may be obtained from Biosynth® AG, and in particular, may be ordered via the Biosynth® AG website, namely: http://www.biosynth.com.

Secondly, there are enzyme substrates based on hydroxyquinoline, dihydroxyanthraquinone, catechol, dihydroxyflavone or esculetin and their derivatives which, in the presence of iron salts, produce a coloured precipitate. There too, their applications substantially relate to osidase-, esterase- and phosphatase-type enzymatic activities.

Thirdly, mention may be made of enzyme substrates based on nitrophenol and nitroaniline and derivatives, which result in the formation of a yellow compound. They make it possible to detect osidase, esterase and phosphatase activities in the case of nitrophenol-based substrates and peptidase activities in the case of nitroaniline-based substrates. However, in the case of detection of peptidase activities, the released nitroaniline is toxic for the bacteria which it is desired to identify or characterise, which may prove to be detrimental to ongoing or subsequent analyses. On the other hand, they are generally little suited to use on a solid support and better suited to use in a liquid medium. In addition, the colour (yellow) has a low contrast in biological media (which affects the detection sensitivity of the corresponding microbiological tests).

Fourthly, there are enzyme substrates based on naphthol and naphthylamine and its derivatives. In this case, the enzyme-substrate reaction takes place in two steps, naphthol or naphthylamine released by the enzymatic activity undergoes "azo-coupling" in the presence of a diazonium salt which is added at the moment of revealing, leading to the formation of an insoluble coloured compound. They make it possible to detect osidase and esterase activities by means of naphthol and peptidase activities by means of naphthylamine. The "azo-coupling" reaction take place in a medium which is often chemically aggressive, toxic to bacteria and making the sample unusable for other analyses, in addition naphthylamines are carcinogenic.

Among the fluorogenic enzyme substrates usable in terms of the present invention, mention may be made notably of the derivatives of coumarin, fluorescein, rhodamine, phenoxazine and hydroxyflavone, or even the enzyme substrates ELF®97 or their derivatives.

According to a preferred embodiment, if the reaction medium according to the invention in which the antimicrobial compounds according to the invention are used as a selective agent in order to specifically target a Gram-negative (Gram-) bacterium, such as one belonging to the genus *Salmonella*, said reaction medium may also comprise at least one anti-Gram-positive (anti-Gram+) selective system and/or antifungal selective system. Anti-Gram+ and/or antifungal selective systems are well known to the person skilled in the art. By way of example, mention may be made of surfactants, glycopeptides, amphotericin, azoles, crystal violet (non-exhaustive list) at concentrations known to the person skilled in the art to obtain their intended effect, namely the elimination of Gram-positive bacteria. By analogy, if the reaction medium according to the invention uses at least one new antimicrobial compound as a selective agent of at least one Gram-positive (Gram+) bacterium, such as a bacterium of the species *Staphylococcus aureus*, at least one anti-Gram- and/or antifungal selective system, well known to the person skilled in the art, may be used. By way of example, mention may be made of aztreonam, polymixins, nalidixic acid.

If incubation is necessary in order to enable growth of the target/sought microorganisms, the reaction medium according to the invention seeded with the biological sample to be tested is incubated. "Incubate" is understood to mean raising to and holding at an appropriate temperature, generally of between 20° C. and 50° C., preferably between 30 and 45° C., for between 1 and 48 hours, preferably between 4 and 24 hours, more preferably between 16 and 24 hours.

"At least one target microorganism" is understood to mean, in terms of the present invention, at least one microorganism which it is desired to detect and/or identify and/or count.

Conversely, "non-target microorganisms" are understood to mean microorganisms which it is not desired to detect and/or identify and/or count and which do not present any interest insofar as it is not desired to detect and/or identify and/or count them. It is vital to avoid this or these non-target microorganism(s) insofar as they are capable of inducing false positive results and therefore of affecting the specificity of detection and/or identification and/or counting of said at least one target microorganism.

BRIEF DESCRIPTION OF THE DRAWINGS AND FIGURES

FIG. 1 presents the structure of the six antimicrobial compounds A-F, the inhibiting capacity of which against the main bacteria groups is evaluated in example 2 below (the new antimicrobial compounds according to the invention being illustrated by structures C and E; structures A, B, D and F concerning compounds from the prior art).

Figure 2:
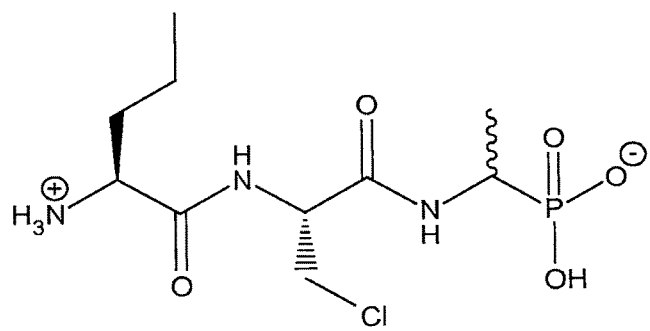
Figure 2:
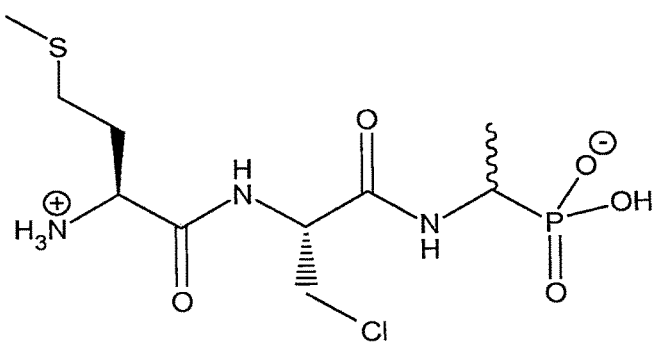
Figure 2:
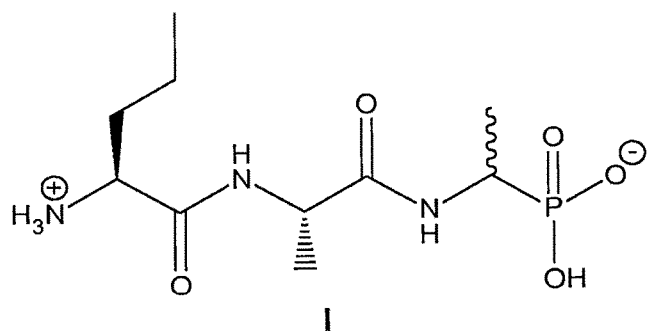
Figure 2:
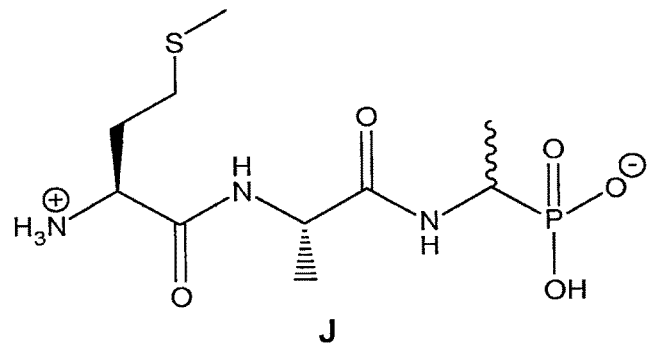

FIG. 2 presents the structure of four other antimicrobial compounds according to the invention, namely compounds G-J.

Figure 3A:
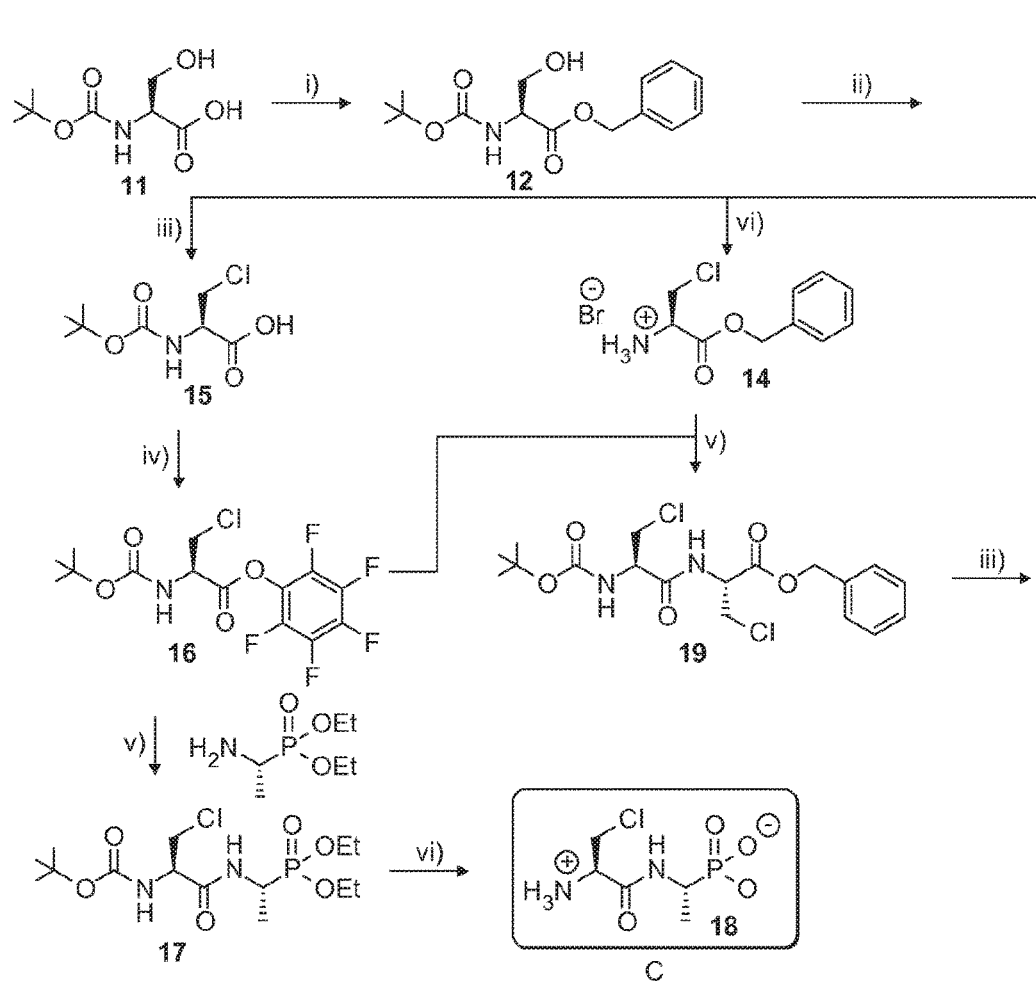
Figure 3B:
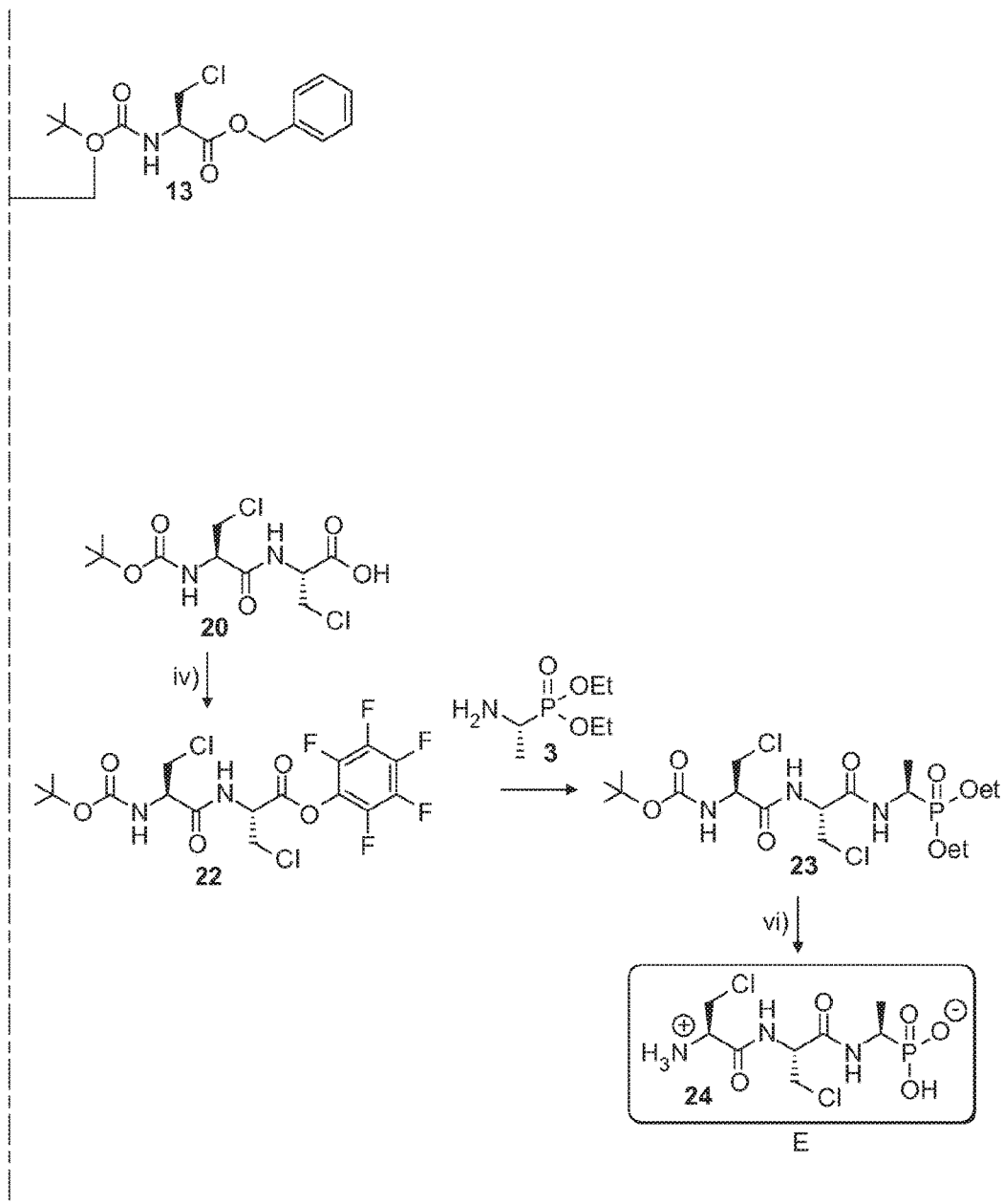

FIGS. 3A and 3B, meanwhile, illustrate the various steps in a synthesis method for the preparation of ß-chloro-L-alanyl-L-1-aminoethylphosphonic acid 18 (represented by structure C in FIG. 1) and of ß-chloro-L-alanyl-ß-chloro-L-alanyl-L-1-aminoethylphosphonic acid 24 (for the structure represented by structure E in FIG. 1).

Figure 4:
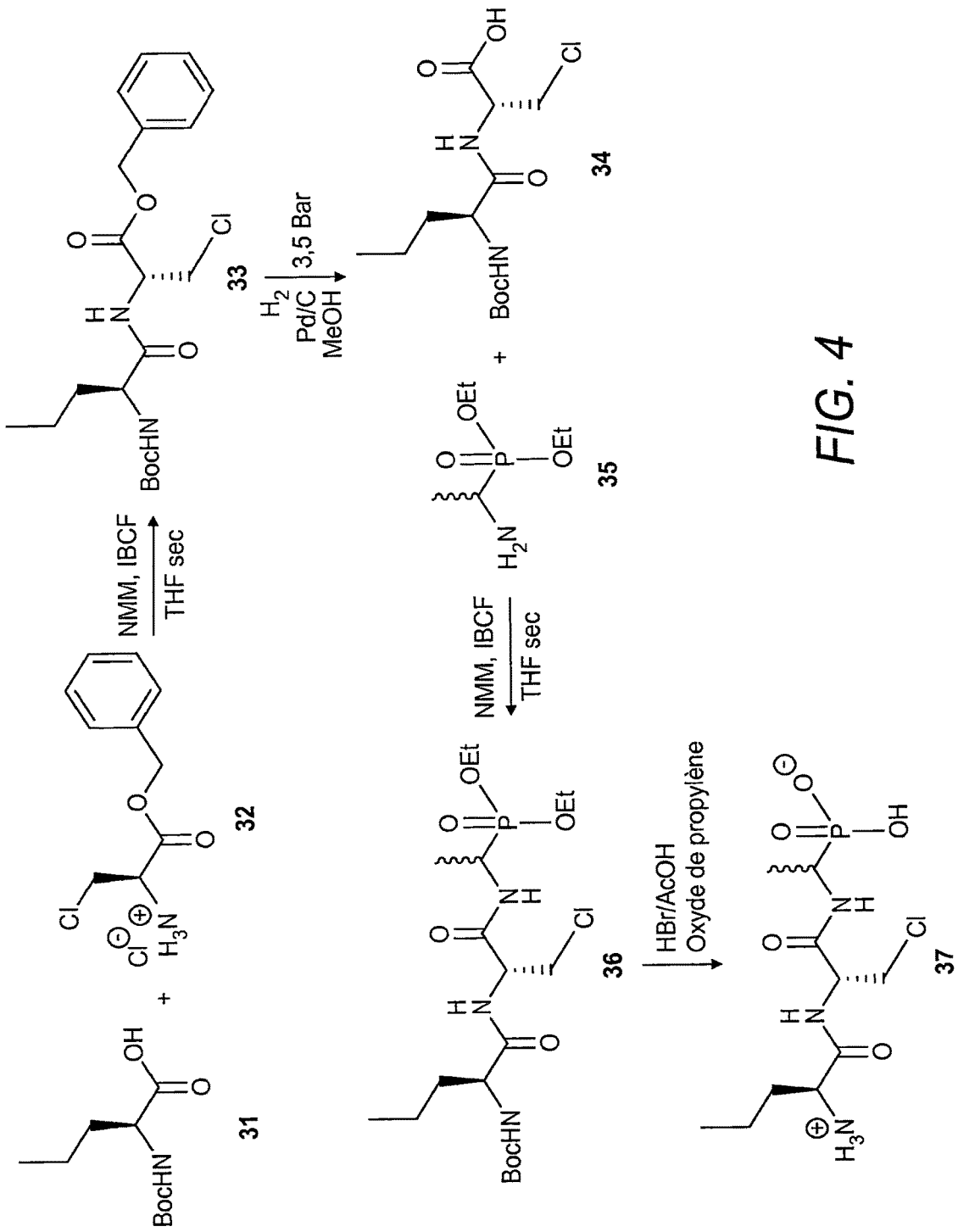

FIG. 4 presents, schematically, the synthesis method of another antimicrobial compound according to the present invention, namely the compound L-Norvalinyl-L-β-chloro-alanyl-D/L-fosfalin 37 (compound G in FIG. 2).

Figure 5:
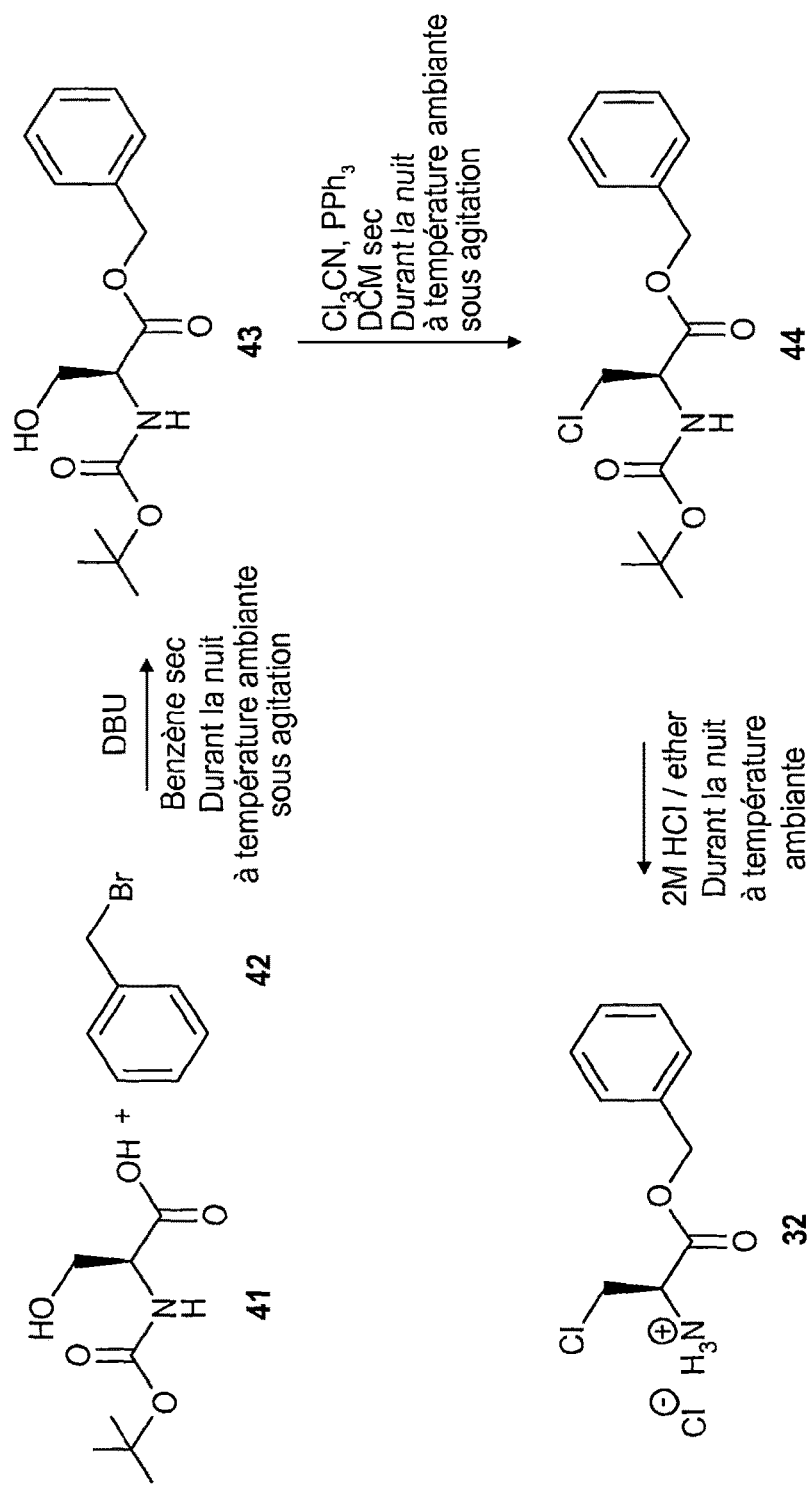

FIG. 5 illustrates the various synthesis steps of a reaction intermediate making it possible to obtain the compound L-Norvalinyl-L-β-chloroalanyl-D/L-fosfalin 37, namely β-chloro-L-alanine O-benzyl ester 32 (from tBoc-L-serine 41).

Figure 6:
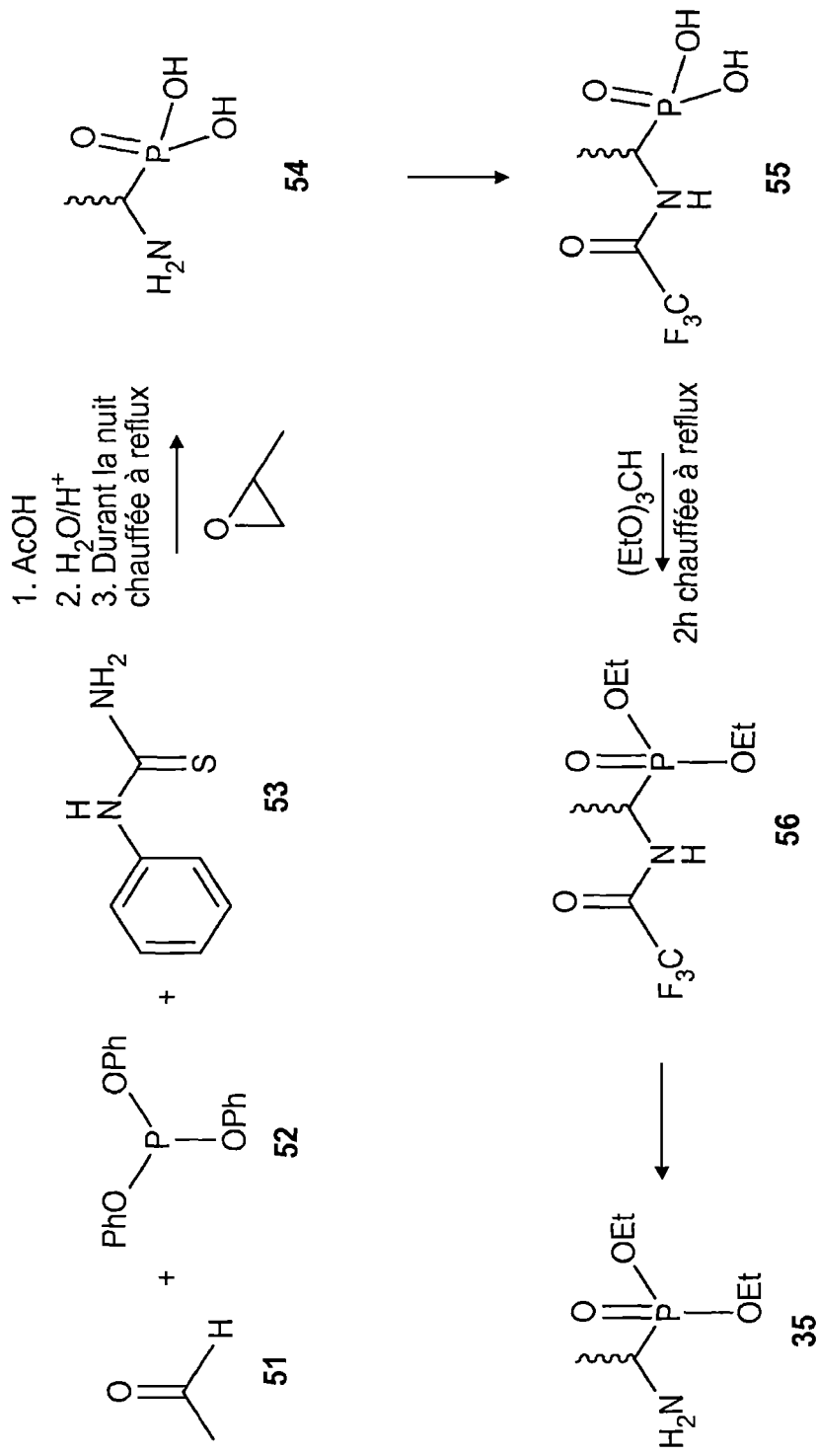

FIG. 6, meanwhile, represents the various synthesis steps of another reaction intermediate making it possible to obtain the compound L-Norvalinyl-L-β-chloroalanyl-D/L-fosfalin 37, namely D/L-fosfalin diethyl ester 35.

DETAILED DESCRIPTION OF THE INVENTION

The examples below will enable the present invention to be better understood. Nevertheless, these examples are given merely by way of illustration and must by no means be regarded as limiting the scope of said invention in any way.

Example 1: Synthesis Method of Antimicrobial Compounds C and E According to the Invention (FIG. 1)

1.1 General Points

The synthesis of the prior art compounds represented by formulae A, B, D and F in FIG. 1 is well known to the person skilled in the art. The synthesis method of the new antimicrobial compounds according to the invention is illustrated below, for the compounds represented by formulae C and E in FIG. 1. This synthesis method is moreover outlined in FIGS. 3A and 3B. The reagents and conditions used within the framework of this synthesis method are as follows: i) benzyl bromide, DBU, benzene; ii) Cl$_3$CCN, PPh$_3$, DCM, N$_2$, t.a.; iii) H$_2$, 10% Pd/C, MeOH; iv) PFP, DCC, EtOAc; v) DCC, DCM, DMF; vi) HBr, AcOH, then propylene oxide.

The NMR spectra were obtained on a Bruker Ultrashield 300 spectrometer (at 300 MHz for the $^1$H spectra and at 75 MHz for the $^{13}$C spectra). The chemical shifts are indicated in ppm downfield from tetramethylsilane, using the residual chloroform (δ=7.26 in $^1$H NMR) or the middle peak of the CDCl$_3$ carbon triplet (δ=77.23 in $^{13}$C NMR) as an internal standard. The melting points were obtained by means of a Reichart-Kofler heating plate microscope and are non-corrected. The infrared spectra were recorded using a Perkin-Elmer Spectrum BX FT-IR instrument. The low-resolution mass spectra were recorded on a Bruker Esquire 3000plus analyser using a positive ion mode electrovaporisation source. The high-resolution mass spectra were obtained on an LTQ Orbitrap XL instrument in nanospray ionisation mode. The elemental analyses were performed using an Exeter Analytical CE-440 Elemental Analyzer. All the commercially available reagents and solvents were obtained from Sigma-Aldrich, Alfa-Aesar, Fisher Scientific and Fluka, and were used without any additional purification. Thin-layer chromatography was performed on Merck silica gel plates (60E-254).

1.2 Preparation of tBoc-L-serine benzyl ester 12

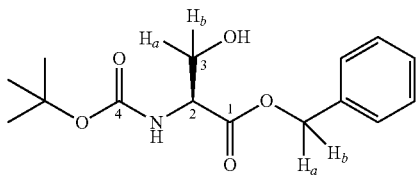

Some $^t$Boc-serine 11 (16.60 g, 81.0 mmol) was dissolved in benzene (250 mL) and some DBU (18.90 g, 21.6 mL, 124.0 mmol) was added. Some benzyl bromide (21.25 g, 15 mL, 124.0 mmol) was then added dropwise to the agitated reaction mixture. After agitation at ambient temperature overnight, the reaction was neutralised with a 1M solution of HCl (150 mL). The benzene was eliminated at low pressure, and the residue was taken up in ethyl acetate. The solution was washed with brine, the organic layer was dried on Na$_2$SO$_4$, and then the solvent was eliminated under vacuum to give the raw product. After column chromatography (50% petroleum ether, 50% ethyl acetate), tBoc-serine benzyl ester 12 was obtained in the form of a white solid (16.90 g, 57.0 mmol, 71%); melting point 61-63° C. (melting point in the literature 69-70° C. [16]); [Found: C, 60.63; H, 7.16; N, 4.64. C$_{15}$H$_{21}$NO$_5$ requires C, 61.00; H, 7.17; N, 4.74%]; $v_{max}$/cm$^{-1}$ 3417, 3356 (NH and OH), 1756 (C=O, ester), 1667 (C=O, carbamate), 1523 (amide II); $^1$H NMR (300 MHz, CDCl$_3$) δ$_H$ 1.44 (9H, s, C(CH$_3$)$_3$), 2.24 (1H, br, OH), 3.91 (1H, br d, J=11.1 Hz, CH$_a$-3), 3.98 (1H, br d, J=11.1 Hz, CH$_b$-3), 4.41 (1H, br, CH-2), 5.19 (1H, d, J=12.3 Hz, COOCH$_a$), 5.24 (1H, d, J=12.3 Hz, COOCH$_b$), 5.44 (1H, br, NH), 7.35-7.37 (5H, m, 5×CH$_{Ar}$); $^{13}$C NMR (75 MHz, CDCl$_3$) δ$_C$ 27.9 (CH$_3$, C(CH$_3$)$_3$), 55.6 (CH, C-2), 63.3

(CH$_2$), 67.1 (CH$_2$), 80.1 (quat., C(CH$_3$)$_3$), 127.8 (2×CH$_{Ar}$), 128.1 (CH$_{Ar}$), 128.3 (2×CH$_{Ar}$), 134.9 (quat., C$_{Ar}$), 153.0 (quat., C=O), 170.3 (quat., C=O); MS (ESI) m/z 318.3 (MNa$^+$).

1.3 Preparation of $^t$Boc-β-chloro-L-alanine benzyl ester 13

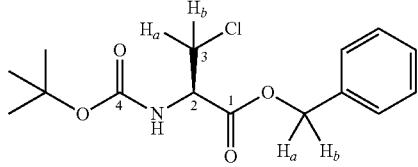

Some trichloro-acetonitrile (15.16 g, 10.5 mL, 105.0 mmol) was added to a solution of $^t$Boc-serine benzyl ester 12 (15.58 g, 52.8 mmol) in dichloromethane (200 mL), under nitrogen, followed by 10 minutes of agitation at ambient temperature. Some triphenylphosphine (27.54 g, 105.0 mmol) was dissolved in dichloromethane (150 mL) under nitrogen, and this solution was added dropwise to the agitated reaction mixture. After agitation at ambient temperature overnight, the reaction was neutralised with brine (250 mL); after separation, the organic layer was extracted with brine (3×100 mL). The organic layer was dried on anhydrous sodium sulfate, and the solvent was eliminated under low pressure to give the raw product. Purification by column chromatography (70% petroleum ether, 30% ethyl acetate) gave the product 13 in the form of a white solid (14.94 g, 47.6 mmol, 90%); melting point 54-57° C.; [Found: C, 57.53; H, 6.49; N, 4.38. C$_{15}$H$_{20}$ClNO$_4$ requires C, 57.42; H, 6.42; N, 4.46%]; $v_{max}$/cm$^{-1}$ 3364 (NH), 1725 (C=O, ester), 1680 (C=O, carbamate), 1518 (amide II); $^1$H NMR (300 MHz, CDCl$_3$) δ$_H$ 1.45 (9H, s, C(CH$_3$)$_3$), 3.84 (1H, dd, J=3.3 and 11.4 Hz, CH$_a$-3), 4.00 (1H, dd, J=3.3 and 11.4 Hz, CH$_b$-3), 4.74 (1H, m, CH-2), 5.22 (1H, d, J=12.3 Hz, COOCH$_a$), 5.27 (1H, d, J=12.3 Hz, COOCH$_b$), 5.43 (1H, d, J=7.2 Hz, NH), 7.36 (5H, m, 5×CH$_{Ar}$); $^{13}$C NMR (75 MHz, CDCl$_3$) δ$_C$ 28.3 (CH$_3$, C(CH$_3$)$_3$), 45.5 (CH$_2$, C-3), 54.6 (CH, C-2), 67.8 (COOCH$_2$), 80.5 (quat., C(CH$_3$)$_3$), 128.3 (CH), 128.6 (2×CH), 128.6 (2×CH), 134.9 (quat., C$_{Ar}$), 155.0 (quat., C=O), 169.0 (quat., C=O); HRMS (nanospray ionisation) calculated for (C$_{15}$H$_{21}$NO$_4$Cl)$^+$ 314.1154, found 314.1159.

1.4 Preparation of β-chloro-L-alanine HBr benzyl ester 14

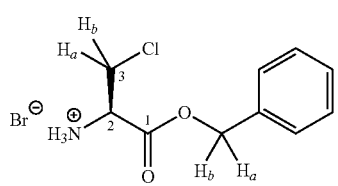

Some $^t$Boc-β-chloro-L-alanine benzyl ester 13 (1.40 g, 4.46 mmol) was dissolved in a minimal quantity of acetic acid (5 mL), and then HBr in AcOH (33% m/m) was added (5.53 mL, 30.7 mmol of HBr) and the reaction mixture was agitated for 10 minutes at ambient temperature. The reaction was neutralised with diethyl ether (200 mL) and the solution was kept in the freezer overnight. At rest, a white solid precipitated out, which was collected by filtration, and washed with cold diethyl ether to give the product 14 (1.10 g, 3.6 mmol, 81%); melting point 131-134° C.; [Found: C, 40.56; H, 4.51; N, 4.68. C$_{10}$H$_{13}$BrClNO$_2$ requires C, 40.77; H, 4.45; N, 4.75%]; $v_{max}$/cm$^{-1}$ 2950, 2875, 2846 (br NH$_3^+$), 1750 (C=O, ester), 1489, 1228, 1208 (C—O); $^1$H NMR (300 MHz, D$_2$O) δ$_H$ 4.17 (1H, dd, J=3.3 and 12.6 Hz, CH$_a$-3), 4.31 (1H, dd, J=3.3 and 12.6 Hz, CH$_b$-3), 4.81 (1H, m, CH-2), 5.31 (1H, d, J=12.3 Hz, COOCH$_a$), 5.39 (1H, d, J=12.3 Hz, COOCH$_b$), 7.55 (5H, m, 5×CH$_{Ar}$); $^{13}$C NMR (75 MHz, D$_2$O) δ$_C$ 41.8 (CH$_2$, C-3), 53.9 (CH, C-2), 69.2 (COOCH$_2$), 128.7 (2×CH), 128.9 (2×CH), 129.1 (CH), 134.5 (quat., C$_{Ar}$), 167.0 (quat., C=O); HRMS (nanospray ionisation) calculated for (C$_{10}$H$_{13}^{35}$ClNO$_2$)$^+$ 214.0629, found 214.0630.

1.5 Preparation of the compound $^t$Boc-β-chloro-L-alanine 15

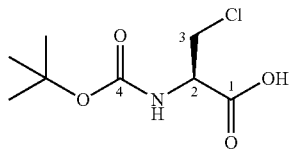

Some tBoc-β-chloro-L-alanine benzyl ester 13 (1.57 g, 5.0 mmol) was dissolved in methanol (50 mL) and 10% palladium on charcoal (0.16 g) in ethyl acetate (20 mL) was added. The reaction was agitated at a pressure of 1.5 bar H$_2$ overnight. The catalyst was eliminated by filtration through a Celite plug and washed out with methanol (200 mL). After elimination of the methanol at low pressure, the raw product was purified by column chromatography (95% dichloromethane, 5% methanol) to give the product 15 in the form of a white solid (0.99 g, 4.4 mmol, 88%); melting point 119-123° C. (melting point in the literature 123-125° C. (13)); $v_{max}$/cm$^{-1}$ 3434 (NH), 2975 (OH), 1752 (C=O), 1734 (C=O), 1677, 1521 (amide II), 1370, 1212; $^1$H NMR (300 MHz, CDCl$_3$) δ$_H$1.47 (9H, s, C(CH$_3$)$_3$), 3.90 (1H, dd, J=2.7 and 11.1 Hz, CH$_a$-3), 4.05 (1H, d, J=11.1 Hz, CH$_b$-3), 4.78 (1H, m, CH-2), 5.47 (1H, d, J=6.3 Hz, NH); $^{13}$C NMR (75 MHz, CDCl$_3$) δ$_C$ 28.3 (CH$_3$, C(CH$_3$)$_3$), 45.2 (CH$_2$, C-3), 54.3 (CH, C-2), 80.9 (quat., C(CH$_3$)$_3$), 155.3 (quat., C=O, C-4), 173.2 (quat., C=O, C-1); HRMS (nanospray ionisation) calculated for (C$_8$H$_{13}$NO$_4^{35}$Cl)$^-$ 222.0539, found 222.0541.

1.6 Preparation of $^t$Boc-β-chloro-L-alanine pentafluorophenol ester 16

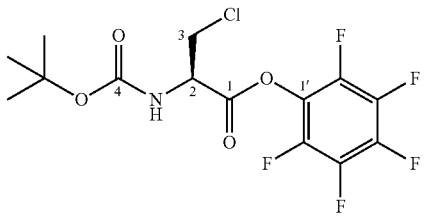 [SMILES: CC(C)(C)OC(=O)N[C@@H](CCl)C(=O)Oc1c(F)c(F)c(F)c(F)c1F]

Some tBoc-β-chloro-L-alanine 15 (1.16 g, 5.2 mmol) and pentafluorophenol (0.95 g, 5.7 mmol) was dissolved in ethyl acetate (25 mL) and cooled in an ice bath. Some dicyclohexylcarbodiimide (1.05 g, 5.7 mmol) was added and the solution was agitated for 3 hours. The precipitated urea by-product was eliminated by filtration. The residue was concentrated at low pressure, and any additional precipitate was eliminated by filtration. The remaining ethyl acetate was eliminated by evaporation. The oil thus obtained was triturated with petroleum ether to give the product 16 in the form of a white solid (3.35 g, 8.6 mmol, 69%) which was collected by filtration; melting point 128-131° C.; [Found: C, 43.53; H. 3.49; N, 3.63. $C_{14}H_{13}{}^{35}ClF_5NO_4$ requires C, 43.15; H, 3.36; N, 3.59%]; $v_{max}/cm^{-1}$ 3367 (NH), 1780 (C=O), 1681 (C=O), 1518 (amide II); $^1$H NMR (300 MHz, CDCl$_3$) $\delta_H$ 1.48 (9H, s, C(CH$_3$)$_3$), 3.94 (1H, dd, J=3.6 and 11.4 Hz, CH$_a$-3), 3.96 (1H, dd, J=3.6 and 11.4 Hz, CH$_b$-3), 5.10 (1H, br t, J=3.6 Hz, CH-2), 5.46 (1H, d, J=7.5 Hz, NH); $^{13}$C NMR (75 MHz, CDCl$_3$) $\delta_C$ 28.25 (CH$_3$, C(CH$_3$)$_3$), 44.78 (CH$_2$, C-3), 54.55 (CH, C-2), 81.26 (quat., C(CH$_3$)$_3$), 118.94 (m, C—F$_{Ar}$), 154.74 (quat., C-1'), 154.79 (quat., C=O, C-4), 166.77 (quat., C=O, C-1); $^{19}$F NMR (282 MHz, CDCl$_3$) $\delta_F$ −161.67 (2F, t, J=19.8 Hz, CF-3' and 5'), −156.73 (1F, t, J=23.1 Hz, CF-4'), −151.63 (2F, d, J=18.9 Hz, CF-2' and 6'); MS (ESI) m/z 388.8 (M-H)$^-$.

1.7 Preparation of $^t$Boc-β-chloro-L-alanyl-L-fosfalin diethyl ester 17

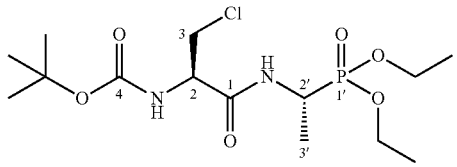 [SMILES: CCOP(=O)(OCC)[C@H](C)NC(=O)[C@H](CCl)NC(=O)OC(C)(C)C]

Some L-fosfalin diethyl ester (1.10 g, 6.1 mmol) was dissolved in dry DCM (50 mL) and cooled in an ice bath. $^t$Boc-β-chloro-alanylpentafluorophenol ester 16 (2.37 g, 6.1 mmol) was added in portions and the reaction mixture was agitated at ambient temperature until completion. The reaction was neutralised with water (150 mL), and then extraction was performed with dichloromethane (3×100 mL). The organic layer was dried on anhydrous MgSO$_4$ and the solvent was eliminated under vacuum. The residue was purified by column chromatography (50% petroleum ether, 50% ethyl acetate up to 90% ethyl acetate, 10% methanol) to give the product 17 in the form of a white solid (1.45 g, 3.8 mmol, 62%); melting point 80-83° C.; [Found: C, 43.46; H, 7.27; N, 7.21. $C_{14}H_{28}ClN_2O_6P$ requires C, 43.47; H, 7.30; N, 7.24%]; $v_{max}/cm^{-1}$ 3303, 3215, 3065, 2978 (NH), 1716 (C=O), 1667 (C=O), 1555, 1518 (amide II); $^1$H NMR (300 MHz, CDCl$_3$) $\delta_H$ 1.25-1.42 (9H, m, 3×CH$_3$), 1.46 (9H, s, C(CH$_3$)$_3$), 3.73 (1H, dd, J=4.2 and 11.1 Hz, CH$_a$-3), 4.00 (1H, dd, J=4.2 and 11.1 Hz, CH$_b$-3), 4.07-4.18 (4H, m, 2×OCH$_2$), 4.39-4.54 (2H, m, CH-2 and 2'), 5.35 (1H, d, J=8.4 Hz, NH), 6.77 (1H, d, J=8.7 Hz, NH); $^{13}$C NMR (75 MHz, CDCl$_3$) $\delta_C$ 15.8 (CH$_3$, C-3'), 16.3-16.5 (2×CH$_3$, m, CH$_3$CH$_2$O), 28.2 (3×CH$_3$, C(CH$_3$)$_3$), 40.3 (CH), 42.4 (CH), 44.9 (CH$_2$, C-3), 62.6 (CH$_2$, d, J=6.75 Hz, OCH$_2$CH$_3$), 62.9 (CH$_2$, d, J=6.6 Hz, OCH$_2$CH$_3$), 80.8 (quat., C(CH$_3$)$_3$), 155.0 (quat., C=O), 168.3 (quat., C=O); $^{31}$P NMR (121.5 MHz, CDCl$_3$) $\delta_P$ 24.6 (m); MS (ESI) m/z 387.3 (MH$^+$), 409.3 (MNa$^+$), 385.1 (M$^-$).

1.8 Obtaining the compound β-chloro-L-alanyl-L-fosfalin 18 (compound C in FIG. 1)

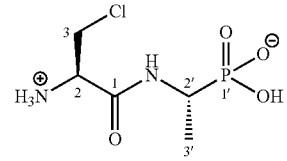

Some tBoc-β-chloro-L-alanyl-L-fosfalin diethyl ester 17 (1.33 g, 3.4 mmol) was agitated in 33% m/m HBr in acetic acid (17 mL) for 24 h. The reaction mixture was poured into diethyl ether (200 mL) and placed in the freezer (−15° C.) overnight. The diethyl ether was decanted off and the residual precipitate was taken up in a minimal quantity of methanol (approximately 10 mL). Then propylene oxide was added in large excess (approximately 250 mL). The hygroscopic precipitate was filtered and recrystallised from water and acetone to give the product 18 in the form of a white solid (0.99 g, 3.2 mmol, 93%); melting point 210-212° C.; [Found: C, 25.80; H, 5.21; N, 12.04. $C_5H_{12}ClN_2O_4P$ requires C, 26.04; H, 5.25; N, 12.15%] $v_{max}/cm^{-1}$ 3258 (br NH), 3100, 2930 (br) (OH), 1654 (C=O), 1565, 1514 (amide II), 1038; $^1$H NMR (300 MHz, D$_2$O) $\delta_H$ 1.30 (3H, dd, J=7.2 and 15 Hz, CH$_3$-3'), 3.97-4.11 (3H, m, CH$_2$-3 and CH-2'), 4.39 (1H, m, CH-2); $^{13}$C NMR (75 MHz, D$_2$O) $\delta_C$ 15.2 (CH$_3$, C-3'), 42.6 (CH$_2$, C-3), 44.2 (CH, d, J=147.9 Hz, C-2'), 54.2 (CH, C-2), 165.6 (quat., C=O, C-1); $^{31}$P NMR (121.5 MHz, CDCl$_3$) $\delta_P$ 18.6 (m); HRMS (nanospray ionisation) calculated for $(C_5H_{11}N_2O_4P^{35}Cl)^-$ 229.0150, found 229.0154.

1.9 Preparation of $^t$Boc-β-chloro-L-alanyl-β-chloro-L-alanine benzyl ester 19

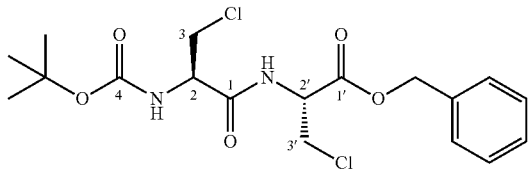 [SMILES: CC(C)(C)OC(=O)N[C@@H](CCl)C(=O)N[C@@H](CCl)C(=O)OCc1ccccc1]

Some β-chloro-L-alanine benzyl ester hydrobromide 14 (1.13 g, 3.9 mmol) was dissolved in DMF (30 mL) and added to a solution of tBoc-β-chloro-L-alanine pentafluorophenol ester 16 (1.50 g, 3.9 mmol) in dichloromethane (10 mL) at 0° C. Some diisopropylethylamine (0.50 g, 0.66 mL, 3.9 mmol) was added dropwise to this solution. The mixture thus obtained was agitated at ambient temperature for 2 hours, and then heated to 35° C., and the progress of the reaction was monitored by TLC (80% petroleum ether, 20% ethyl acetate). Once the reaction was finished, it was neutralised with a 1M solution of HCl (50 mL) and the organic layer was washed with water (100 mL) and brine (100 mL). The organic layer was dried on anhydrous sodium sulfate and the solvent was evaporated under vacuum. The raw product was purified by gradient column chromatography (from 80% petroleum ether, 20% ethyl acetate; to 50% petroleum ether, 50% ethyl acetate) to give the product 19 in the form of a white solid (1.16 g, 2.8 mmol, 70%); melting point 89-91° C.; [Found: C, 51.83; H, 5.78; N, 6.78. $C_{18}H_{24}{}^{35}Cl_2N_2O_5$ requires C, 51.56; H, 5.77; N, 6.68%]; $v_{max}/cm^{-1}$ 3336 (NH), 3321 (NH), 1739 (C=O), 1655 (m, C=O), 1508 (amide II); $^1H$ NMR (300 MHz, CDCl$_3$) $\delta_H$ 1.48 (9H, s, C(CH$_3$)$_3$), 3.73 (1H, dd, J=4.8 and 11.1 Hz, CH), 3.89-4.06 (3H, m, 3×CH), 4.55 (1H, br, CH), 4.98 (1H, m, CH), 5.24 (2H, m, COOCH$_2$), 5.35 (1H, br, NH), 7.25 (1H, br, NH), 7.37 (5H, br s, 5×CH$_{Ar}$); $^{13}C$ NMR (75 MHz, CDCl$_3$) $\delta_C$ 28.24 (CH$_3$, C(CH$_3$)$_3$), 33.90 (CH$_2$Ph), 44.5 (CH), 44.60 (CH$_2$), 53.61 (CH), 68.13 (CH$_2$), 81.37 (quat., C(CH$_3$)$_3$), 128.22 (CH$_{Ar}$), 128.41 (CH$_{Ar}$), 128.69 (CH$_{Ar}$), 134.71 (quat.), 168.19 (2×quat., C=O), 168.90 (quat., C=O); HRMS (nanospray ionisation) calculated for $(C_{18}H_{25}N_2O_5{}^{35}Cl)^+$ 419.1135, found 419.1139.

1.10 Preparation of the compound $^t$Boc-β-chloro-L-alanyl-β-chloro-L-alanine

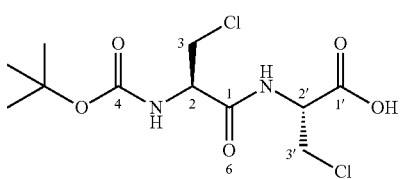 [SMILES: CC(C)(C)OC(=O)N[C@@H](CCl)C(=O)N[C@@H](CCl)C(=O)O]

Some $^t$Boc-β-chloro-L-alanine-β-chloro-L-alanine benzyl ester 19 (1.00 g, 2.4 mmol) was dissolved in methanol (50 mL) and 10% palladium on charcoal (0.10 g) in ethyl acetate (20 mL) was added. The reaction mixture was agitated in an H$_2$ atmosphere (1.8 bar) for 24 h, and then filtered through a Celite plug and washed with methanol (200 mL). The solvents were eliminated under vacuum and, after purification by column chromatography (95% DCM, 5% methanol), upon trituration with petroleum ether, the product 20 was obtained in the form of a white solid (0.52 g, 1.6 mmol, 66%); melting point 72-74° C.; $v_{max}/cm^{-1}$ 3320 (NH), 2978 (NH), 1724 (C=O), 1665 (C=O), 1530 (amide II); $^1H$ NMR (300 MHz, DMSO-d$_6$) $\delta_H$ 1.39 (9H, s, C(CH$_3$)$_3$), 3.67 (1H, dd, J=8.4 and 11.1 Hz, CH), 3.79-3.95 (3H, m, CH$_2$ and CH), 4.36 (1H, br, CH), 4.61-4.67 (1H, m, CH), 7.16 (1H, d, J=8.1 Hz, NH), 8.38 (1H, d, J=7.5 Hz, NH); HRMS (nanospray ionisation) calculated for $(C_{11}H_{17}{}^{35}Cl_2N_2O5)^-$ 327.0520, found 327.0517;

1.11 Preparation of $^t$Boc-β-chloro-L-alanyl-β-chloro-L-alanine pentaflurophenol ester 22

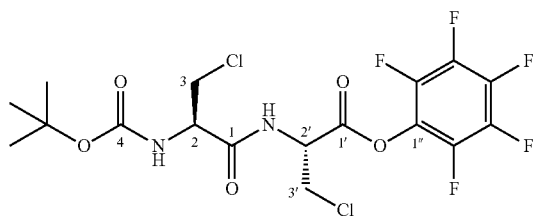 [SMILES: CC(C)(C)OC(=O)N[C@@H](CCl)C(=O)N[C@@H](CCl)C(=O)Oc1c(F)c(F)c(F)c(F)c1F]

Some $^t$Boc-β-chloro-L-alanyl-β-chloro-L-alanine 20 (0.48 g, 1.46 mmol) was dissolved in ethyl acetate (50 mL) and cooled in an ice bath, which was followed by the addition of pentafluorophenol (0.29 g, 1.56 mmol) and dicyclohexylcarbodiimide (0.33 g, 1.61 mmol). The solution was agitated at 0° C. for 2 hours and the precipitated urea was eliminated by filtration. The residue was concentrated under vacuum and any new precipitate was also eliminated by filtration. The ethyl acetate was eliminated under vacuum and the oil thus obtained was triturated with petroleum ether to give the product 22 in the form of a white solid (0.65 g, 1.3 mmol, 89%), which was collected by filtration and taken on to the next step without any other purification; $v_{max}/cm^{-1}$ 3334 (NH), 3006, 2970, 2939 (NH), 1787 (C=O), 1688 (C=O), 1664 (C=O), 1514 (amide II); $^1H$ NMR (300 MHz, CDCl$_3$) $\delta_H$ 1.46 (9H, s, C(CH$_3$)$_3$), 3.76 (1H, dd, J=4.7 and 11.3 Hz, CH$_a$), 3.98 (1H, dd, J=3.5 and 11.7 Hz, CH$_c$), 4.06 (1H, dd, J=4.4 and 11.3 Hz, CH$_b$), 4.16 (1H, dd, J=3.2 and 11.7 Hz, CH$_d$), 4.53 (1H, br, CH), 5.32-5.37 (2H, m, CH and NH), 7.31 (1H, d, J=7.1 Hz, NH);

1.12 Preparation of $^t$Boc-β-chloro-L-alanyl-β-chloro-L-alanyl-L-fosfalin diethyl ester 23

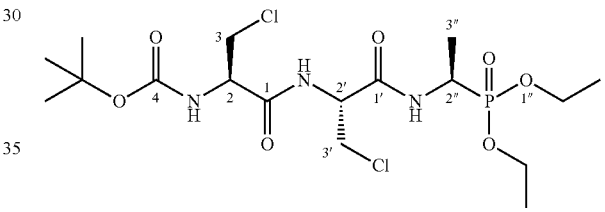

Some $^t$BOC-β-chloro-L-alanyl-β-chloro-L-alanine pentafluorophenol ester 22 (0.95 g, 1.9 mmol) and diethyl 1-aminoethylphosphonate 3 (0.32 g, 1.9 mmol) was dissolved in dichloromethane (25 mL) at 0° C., and then agitated at ambient temperature until completion of the reaction, followed by a TLC. After extraction with water (100 mL), the organic layer was dried on anhydrous MgSO$_4$ and the volatile components were eliminated at low pressure. The raw solid was purified by column chromatography (97% DCM, 3% MeOH) to give the product 23 in the form of a white solid (0.62 g, 1.3 mmol, 66%); melting point 154.6-155.9° C.; $v_{max}/cm^{-1}$ 3291, 3265, 2962, 2848 (NH), 1680 (C=O), 1639 (C=O), 1523 (amide II); $^1H$ NMR (300 MHz, CDCl$_3$) $\delta_H$ 1.35-1.41 (9H, m, 3×CH$_3$), 1.48 (9H, s, C(CH$_3$)$_3$), 3.73-3.80 (2H, m, CH$_a$-3 and CH$_a$-3'), 4.01-4.2 (6H, m, CH$_b$-3, CH$_b$-3' and 2×OCH$_2$), 4.43-4.54 (2H, m, CH-2" and CH-2), 4.79-4.84 (1H, m, CH-2'), 5.38 (1H, d, J=6.9 Hz, NH), 7.05 (1H, d, J=9.0 Hz, NH), 7.19 (1H, d, J=7.8 Hz, NH); $^{13}C$ NMR (75 MHz, CDCl$_3$) $\delta_C$ 15.7 (CH$_3$, C-3'), 16.6 (CH$_3$, OCH$_2$CH$_3$), 16.7 (CH$_3$, OCH$_2$CH$_3$), 28.4 (3×CH$_3$, C(CH$_3$)$_3$), 40.7 (CH), 44.5 (CH$_2$), 44.6 (CH$_2$), 49.4 (CH), 54.1 (CH), 62.8 (CH$_2$, d, J=15.5 Hz, OCH$_2$CH$_3$), 63.1 (CH$_2$, d, J=15.7 Hz, OCH$_2$CH$_3$), 81.6 (quat., C(CH$_3$)$_3$), 156.9 (quat., C=O), 168.9 (quat., C=O), 177.3 (quat., C=O); MS m/z 514.3, 515.2, 516.2 (MNa$^+$); HRMS (nanospray ionisation) calculated for $(C_{17}H_{33}N_2O_7P^{35}Cl_2)^+$ 492.1428, found 492.1422.

1.13 Obtaining β-chloro-L-alanyl-β-chloro-L-alanyl-L-fosfalin 24 (compound E in FIG. 1)

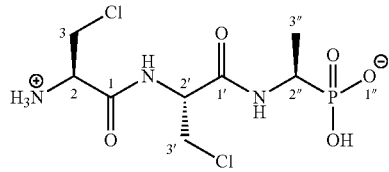 [SMILES: C[C@H](NC(=O)[C@H](CCl)NC(=O)[C@@H]([NH3+])CCl)P(=O)([O-])O]

Some 'BOC-β-chloro-L-alanyl-β-chloro-L-alanyl-L-fosfalin diethyl ether 23 (0.36 g, 0.7 mmol) was dissolved in acetic acid (5 mL) and HBr in AcOH (33% m/m (4 mL) was added. The solution was agitated at ambient temperature overnight, and then the reaction was neutralised with diethyl ether (200 mL). After resting in the freezer (−15° C.) for 4 h, the brown oil thus obtained was separated by decanting off the diethyl ether. The raw product was then washed with cold diethyl ether (5×50 mL). The residue was taken up in methanol (3 mL) and, upon addition of propylene oxide (150 mL), a white precipitate formed. The liquid later was decanted off and the residue was triturated with cold diethyl ether (5×30 mL) to give the product 24 in the form of a white solid (0.18 g, 0.4 mmol, 59%); melting point 157-159° C.; $v_{max}/cm^{-1}$ 3285, 3258 (br NH), 1646 (br) (C=O), 1539 (large amide II), 1152, 1044; $^1$H NMR (300 MHz, D$_2$O) $\delta_H$ 1.37 (3H, dd, J=7.2 and 15.3 Hz, CH$_3$-3"), 3.98-4.2 (5H, m, CH$_2$-3 and CH$_2$-3' and CH), 4.62 (1H, t, J=4.8 Hz, CH), 4.87-4.90 (1H, m, CH); $^{13}$C NMR (75 MHz, D$_2$O) $\delta_C$ 15.4 (CH$_3$, C-3"), 42.4 (CH$_2$), 43.4 (CH$_2$), 45.1 (CH, C-2"), 53.8 (CH), 55.1 (CH), 166.8 (quat., C=O), 168.9 (quat., C=O); HRMS (nanospray ionisation) calculated for $(C_8H_{15}N_3O_5P^{35}Cl_2)^-$ 336.0102, found 336.0096.

Example 2: Evaluation of Antibacterial Activity of Antimicrobial Ccompounds C and E Synthesised According to Example 1

2.1 Introduction

This example 2 presents the results of a study aimed at:
evaluating the antibacterial activity of the compounds according to the invention, as synthesised in Example 1, namely compounds C and E as represented in FIG. 1, and
comparing this antibacterial activity with that obtained by three mimetic peptides of the prior art, namely compounds A, B and D in FIG. 1 and fosfomycin (compound F).

The antibacterial activity of five compounds A-E was evaluated with a large collection of 297 bacteria which included a predominance of multi-resistant strains including carbapenemase-producing enterobacteria (n=128), methicillin-resistant Staphylococci aureus (n=37) and glycopeptide-resistant enterococci (n=43). Fosfomycin, a naturally present antibiotic also containing a phosphonic acid group (F) was included for comparison purposes.

As a reminder, compounds A-F are as follows:
A: L-alanyl-L-1-aminoethylphosphonic acid (alafosfalin);
B: L-alanyl-L-alanyl-L-1-aminoethylphosphonic acid (dialanyl fosfalin);
C: β-chloro-L-alanyl-L-1-aminoethylphosphonic acid (β-Cl-alafosfalin);
D: β-chloro-L-alanyl-β-chloro-L-alanine (β-Cl-Ala-β-Cl-Ala);
E: β-chloro-L-alanyl-β-chloro-L-alanyl-L-1-aminoethylphosphonic acid (β-Cl-Ala-β-Cl-alafosfalin);
F: disodium [(2R,3S)-3-methyloxiran-2-yl] phosphonate (fosfomycin).

2.2 Materials and Methods

Antibacterial agents and media. Fosfomycin, alafosfalin, glucose-6-phosphate and all the ingredients of the antagonist-free agar medium were purchased from Sigma Chemical Company, Poole, United Kingdom. The agar medium IsoSensitest was purchased from Oxoid, Basingstoke, United Kingdom.

Bacterial isolates. The enterobacteria (n=197) were obtained from various international sources, and all possessed β-lactamases which were defined on a molecular level by benchmark laboratories and/or experts renowned in the field. These included Citrobacter freundii (n=5), other species of Citrobacter (n=4), Enterobacter aerogenes (n=1), Enterobacter cloacae (n=27), Escherichia coli (n=53), Klebsiella oxytoca (n=5), Klebsiella pneumoniae (n=87), Kluyvera spp (n=1), Proteus mirabilis (n=8), Providencia rettgeri (n=2), Salmonella spp (n=3), and Serratia marcescens (n=1). Among these 197 isolates, there were 128 (65%) carbapenemase producers, including; 87 with NDM-1, 9 with IMP, 11 with KPC, 14 with OXA-48 and 7 with VIM. The majority of the carbapenemase producers jointly produced broad-spectrum β-lactamases (BSBL) or cephalosporinases (AmpC β-lactamases), but the latter are not documented for the sake of clarity. Among the remaining isolates, 47 possessed BSBLs (20 with CTX-M, 19 with an SHV type, and 8 with a TEM type) and 22 possessed AmpC (3 with ACC-1, 6 with a CMY type, 6 with DHA-1, 3 with an FOX type and 4 with an LAT type).

A collection of 50 isolates of Staphylococci aureus included 36 strains of methicillin-resistant S. aureus (MRSA) frequently encountered in Europe, including strains isolated in Belgium, Finland, France, Germany and the United Kingdom. Another strain of MRSA, NCTC 11939, was included as a control, as well as a methicillin-sensitive control (NCTC 6571). Twelve other isolates of methicillin-sensitive Staphylococcus aureus (MSSA) recently collected from blood cultures were also included. Finally, 50 isolates of enterococci included two control strains (Enterococcus faecalis NCTC 755 and Enterococcus faecium NCTC 7171) and 48 isolates originating from clinical samples obtained from at least three different hospitals. The clinical isolates included E. faecalis (n=10), E. faecium (n=33), Enterococcus casseliflavus (n=3), Enterococcus gallinarum (n=2). Among the 50 isolates, 43 were vancomycin-resistant, as demonstrated by the MIC value and the confirmation of the resistance genes by PCR.

Determining the minimum inhibitory concentrations (MIC). All the MICs were determined using an agar dilution method [16]. This required use of a medium without a defined antagonist (peptone-free), prepared as described previously with the inclusion of 2% horse blood lysed with saponin, 25.0 μg/mL of NAD and 25.0 μg/mL of hemin [17]. The compounds tested were dissolved in sterile deionised water and incorporated into the agar medium in a concentration range of 0.0031 to 8.0 μg/mL (0.016 to 32 μg/mL for gram-positive bacteria). All the isolates were prepared at a density equivalent to 0.5 McFarland units in sterile deionised water using a densitometer (approximately 1.5×10$^8$ CFU/mL), and then diluted to 1 for 15. An aliquot of 1 μL of each diluted suspension was then placed onto plates with a multispot inoculator to give the final recommended inoculation of 10 000 CFU/spot [16]. The MICs of fosfomycin were determined by the same method, except that the IsoSensitest medium (Oxoid, Basingstoke, United Kingdom) was used, plus 25.0 μg/mL of glucose-6-phosphate (Sigma, Poole, United Kingdom) and an extended range of fosfomycin concentrations. All the dishes (including the antimicrobial-free controls) were incubated for 22 hours at 37° C. All the tests were performed on at least two independent replicates in order to examine the reproducibility.

2.3 Results

The minimum inhibitory concentrations (MIC) 50 and 90 of the five compounds A-E were calculated and are presented in Table 1 below. These values correspond respectively to the smallest antibiotic concentration sufficient to inhibit in vitro 50 and 90% of the growth of a bacteria strain, respectively $MIC_{50}$ and $MIC_{90}$.

More specifically, Table 1 below indicates the MICs of the six antimicrobials against the main bacteria groups tested. Alafosfalin presented good activity against most of the enterobacteria isolates, although different species exhibited different degrees of sensitivity. A high activity was observed against 53 isolates of E. coli, of which 35 isolates (66%) were carbapenemase producers. The $MIC_{90}$ for E. coli was 0.25 μg/mL and growth of all the isolates was inhibited by 2 μg/mL. It was found that the activity of alafosfalin was approximately four times higher than that of fosfomycin.

Although the antibacterial activity of alafosfalin against E. coli is satisfactory, as indicated previously, the activity of β-Cl-alafosfalin against E. coli proved to be at least twice that of alafosfalin and at least eight times higher than that of fosfomycin. The $MIC_{90}$ was 0.125 μg/mL and all the isolates saw their growth inhibited by 0.5 μg/mL.

K. pneumoniae was less sensitive to all the compounds tested when compared to E. coli, although numerous isolates presented relatively low MICs. For example, 87% of K. pneumoniae isolates were inhibited by 8 μg/mL alafosfalin and 93% were inhibited by 8 μg/mL β-Cl-alafosfalin.

All the E. cloacae isolates (n=27) were inhibited by 4 μg/mL alafosfalin, which was typically 32 times more active than fosfomycin against this species. As previously, β-Cl-alafosfalin proved to be the most active compound with all the isolates inhibited by 1 μg/mL. The other enterobacteria species are excluded from Table 1, since there were fewer than 10 isolates tested.

For the taxa Citrobacter (n=9), E. aerogenes (n=1), Kluyvera sp. (n=1), and S. marcescens (n=1), all the isolates were sensitive to ≤4 μg/mL alafosfalin and ≤2 μg/mL β-Cl-alafosfalin. One of the five isolates of K. oxytoca required a MIC>8 μg/mL alafosfalin, but all were inhibited by ≤2 μg/mL β-Cl-alafosfalin, demonstrating once more the highly satisfactory antibacterial activity of the latter.

Eight P. mirabilis isolates and two P. rettgeri isolates required MICs ≥8 μg/mL for all the agents tested (including fosfomycin).

Three Salmonella isolates exhibited MICs ≥8.0 μg/mL for alafosfalin but only from 2.0 to 4.0 μg/mL for β-Cl-alafosfalin.

β-Cl-alafosfalin and β-Cl-Ala-β-Cl-Ala had the greatest activity against Staphylococci aureus, but there was a slight overall difference between the five peptide antimicrobials. 90% of the MRSA isolates, originating from various geographic sources, were inhibited by 8.0 μg/mL alafosfalin and all the isolates were inhibited by 2.0 μg/mL β-Cl-alafosfalin, demonstrating once more, a greater antibacterial activity than that of alafosfalin.

Against enterococci, the most noticeable observation was the high activity of di-alanyl fosfalin, for which the MICs were (on average) 16 times lower than those of alafosfalin and, in certain cases, 256 times lower. Among the 34 E. faecium isolates (including 31 vancomycin-resistant isolates), all were inhibited by 32 μg/mL alafosfalin or 4 μg/mL di-alanyl fosfalin. In any event, among the enterococci, the antibacterial activity of β-Cl-Ala-β-Cl-alafosfalin (compound according to the invention) proved greater than that of alafosfalin.

2.4 Conclusion

As we have shown in this study, the antimicrobial compounds according to the present invention, and notably β-Cl-alafosfalin, present a useful in vitro antibacterial activity (very frequently greater than that of alafosfalin) against the majority of bacteria and notably of multi-resistant bacteria. Thus, by way of example, the $MIC_{50}$ and $MIC_{90}$ of alafosfalin for the CPEs were respectively 1 μg/mL and 4 μg/mL, whereas the phosphonopeptide according to the invention, g-Cl-alafosfalin, presented one of the values of 0.5 μg/mL and 2 μg/mL. Alafosfalin was only moderately active against MRSA presenting an $MIC_{90}$ of 8 μg/mL, whereas β-Cl-alafosfalin was more active with an $MIC_{90}$ of 2 μg/mL. Compared to alafosfalin, β-Cl-Ala-β-Cl-alafosfalin enables an inhibition gain targeted on certain species. This may be very useful for inhibiting a species without altering the rest of the microbial flora, for example inhibiting E. coli without inhibiting the other enterobacteria, or E. faecalis without inhibiting E. faecium. This becomes particularly advantageous for specifically isolating a species by inhibiting other bacteria, for example for seeking S. aureus.

TABLE 1

Minimum inhibitory concentrations of various antimicrobial agents against groups of bacteria, including isolates endowed with definite resistance mechanisms.

| Organism (number tested) and antimicrobial agent | Concentration (μg/mL) | | | |
| --- | --- | --- | --- | --- |
| | Modal MIC (most frequent MIC) | $MIC_{50}$ | $MIC_{90}$ | Range |
| Enterobacteriaceae (197) | | | | |
| Alafosfalin | 2 | 2 | >8 | ≤0.031->8 |
| Di-alanyl fosfalin | >8 | 8 | >8 | ≤0.031->8 |
| β-Cl-Alafosfalin | 1 | 0.5 | 8 | ≤0.031->8 |

TABLE 1-continued

Minimum inhibitory concentrations of various antimicrobial agents against groups of bacteria, including isolates endowed with definite resistance mechanisms.

| Organism (number tested) and antimicrobial agent | Concentration (μg/mL) | | | |
|---|---|---|---|---|
| | Modal MIC (most frequent MIC) | $MIC_{50}$ | $MIC_{90}$ | Range |
| β-Cl-Ala-β-Cl-Ala | >8 | >8 | >8 | 2->8 |
| β-Cl-Ala-β-Cl-Alafosfalin | 4 | 2 | >8 | ≤0.031->8 |
| Fosfomycin | 4 | 4 | >32 | 0.125->32 |
| *E. coli* (53) | | | | |
| Alafosfalin | 0.063 | 0.125 | 0.25 | ≤0.031-2 |
| Di-alanyl fosfalin | 0.25 | 0.5 | 2 | ≤0.031->8 |
| β-Cl-Alafosfalin | 0.063 | 0.063 | 0.125 | ≤0.031-0.5 |
| β-Cl-Ala-β-Cl-Ala | 8 | 8 | >8 | 2->8 |
| β-Cl-Ala-β-Cl-Alafosfalin | 0.25 | 0.25 | 1 | ≤0.031-1 |
| Fosfomycin | 0.5 | 0.5 | 1 | 0.125-8 |
| *K. pneumoniae* (87) | | | | |
| Alafosfalin | 2 | 2 | >8 | 0.25->8 |
| Di-alanyl fosfalin | >8 | >8 | >8 | 0.5->8 |
| β-Cl-Alafosfalin | 1 | 1 | 8 | 0.125->8 |
| β-Cl-Ala-β-Cl-Ala | >8 | >8 | >8 | 8->8 |
| β-Cl-Ala-β-Cl-Alafosfalin | 4 | 4 | >8 | 0.5->8 |
| Fosfomycin | 4 | 8 | >32 | 2->32 |
| *E. cloacae* (27) | | | | |
| Alafosfalin | 1 | 1 | 1 | 0.125-4 |
| Di-alanyl fosfalin | 4 | >8 | >8 | 0.25->8 |
| β-Cl-Alafosfalin | 0.5 | 0.5 | 0.5 | 0.063-1 |
| β-Cl-Ala-β-Cl-Ala | >8 | >8 | >8 | 8->8 |
| β-Cl-Ala-β-Cl-Alafosfalin | 1 | 1 | 4 | 0.25-8 |
| Fosfomycin | 16 | 16 | 32 | 4->32 |
| CPE (128) | | | | |
| Alafosfalin | 2 | 1 | 4 | ≤0.031->8 |
| Di-alanyl fosfalin | >8 | 8 | >8 | 0.063->8 |
| β-Cl-Alafosfalin | 1 | 0.5 | 2 | ≤0.031->8 |
| β-Cl-Ala-β-Cl-Ala | >8 | >8 | >8 | 2->8 |
| β-Cl-Ala-β-Cl-Alafosfalin | 4 | 2 | 8 | ≤0.031->8 |
| Fosfomycin | 16 | 4 | 32 | 0.125->32 |
| BSBL (47) | | | | |
| Alafosfalin | 2 | 2 | >8 | ≤0.031->8 |
| Di-alanyl fosfalin | >8 | 8 | >8 | ≤0.031->8 |
| β-Cl-Alafosfalin | 0.063 | 0.5 | >8 | 0.031->8 |
| β-Cl-Ala-β-Cl-Ala | >8 | >8 | >8 | 2->8 |
| β-Cl-Ala-β-Cl-Alafosfalin | >8 | 4 | >8 | 0.063->8 |
| Fosfomycin | >32 | 8 | >32 | 0.125->32 |
| AmpC (22) | | | | |
| Alafosfalin | >8 | 4 | >8 | 0.063->8 |
| Di-alanyl fosfalin | >8 | >8 | >8 | 0.063->8 |
| β-Cl-Alafosfalin | >8 | 2 | >8 | ≤0.031->8 |
| β-Cl-Ala-β-Cl-Ala | >8 | >8 | >8 | 8->8 |
| β-Cl-Ala-β-Cl-Alafosfalin | >8 | 8 | >8 | 0.25->8 |
| Fosfomycin | 32 | 8 | >32 | 0.125->32 |
| All *S. aureus* (50) | | | | |
| Alafosfalin | 4 | 4 | 8 | 0.125-16 |
| Di-alanyl fosfalin | 4 | 8 | 16 | 0.5-32 |
| β-Cl-Alafosfalin | 2 | 1 | 2 | 0.125-4 |
| β-Cl-Ala-β-Cl-Ala | 2 | 2 | 4 | 0.125-16 |
| β-Cl-Ala-β-Cl-Alafosfalin | 16 | 16 | 16 | 2-16 |
| Fosfomycin | 8 | 4 | 16 | 0.5->32 |
| MRSA (37) | | | | |
| Alafosfalin | 4 | 4 | 8 | 0.125-16 |
| Di-alanyl fosfalin | 4 | 8 | 16 | 0.5-32 |
| β-Cl-Alafosfalin | 2 | 2 | 2 | 0.125-2 |
| β-Cl-Ala-β-Cl-Ala | 2 | 2 | 4 | 0.125-16 |
| β-Cl-Ala-β-Cl-Alafosfalin | 16 | 16 | 16 | 2-16 |
| Fosfomycin | 8 | 4 | 16 | 0.5->32 |

TABLE 1-continued

Minimum inhibitory concentrations of various antimicrobial agents against groups of bacteria, including isolates endowed with definite resistance mechanisms.

| Organism (number tested) and antimicrobial agent | Concentration (μg/mL) | | | |
|---|---|---|---|---|
| | Modal MIC (most frequent MIC) | $MIC_{50}$ | $MIC_{90}$ | Range |
| MSSA (13) | | | | |
| Alafosfalin | 4 | 4 | 8 | 0.25-16 |
| Di-alanyl fosfalin | 16 | 8 | 16 | 0.5-32 |
| β-Cl-Alafosfalin | 1 | 1 | 2 | 0.5-4 |
| β-Cl-Ala-β-Cl-Ala | 1 | 1 | 2 | 0.5-2 |
| β-Cl-Ala-β-Cl-Alafosfalin | 16 | 16 | 16 | 4-16 |
| Fosfomycin | 4 | 4 | 16 | 2-16 |
| **All *Enterococci* (50)** | | | | |
| Alafosfalin | 8 | 16 | >32 | 4->32 |
| Di-alanyl fosfalin | 0.5 | 0.5 | 2 | ≤0.016->32 |
| β-Cl-Alafosfalin | 8 | 8 | 16 | 2->32 |
| β-Cl-Ala-β-Cl-Ala | 16 | 16 | 32 | 2-16 |
| β-Cl-Ala-β-Cl-Alafosfalin | 8 | 8 | 16 | 0.125->32 |
| Fosfomycin | >32 | >32 | >32 | 16->32 |
| ***E. faecalis* (11)** | | | | |
| Alafosfalin | 8 | 8 | 32 | 4->32 |
| Di-alanyl fosfalin | 0.031 | 0.063 | 0.5 | ≤0.016->32 |
| β-Cl-Alafosfalin | 8 | 8 | 16 | 4->32 |
| β-Cl-Ala-β-Cl-Ala | 8 | 8 | 16 | 4-16 |
| β-Cl-Ala-β-Cl-Alafosfalin | 0.25 | 0.25 | 4 | 0.125->32 |
| Fosfomycin | 32 | 32 | >32 | 32->32 |
| ***E. faecium* (34)** | | | | |
| Alafosfalin | 16 | 16 | 16 | 4-32 |
| Di-alanyl fosfalin | 0.5 | 0.5 | 2 | ≤0.016-4 |
| β-Cl-Alafosfalin | 4 | 4 | 8 | 2-32 |
| β-Cl-Ala-β-Cl-Ala | 16 | 16 | 32 | 2->32 |
| β-Cl-Ala-β-Cl-Alafosfalin | 8 | 8 | 8 | 0.125->32 |
| Fosfomycin | >32 | >32 | >32 | 16->32 |
| GRE (43) | | | | |
| Alafosfalin | 16 | 16 | >32 | 4->32 |
| Di-alanyl fosfalin | 0.5 | 0.5 | >32 | ≤0.016->32 |
| β-Cl-Alafosfalin | 4 | 8 | 16 | 2->32 |
| β-Cl-Ala-β-Cl-Ala | 16 | 16 | >32 | 4->32 |
| β-Cl-Ala-β-Cl-Alafosfalin | 8 | 8 | 16 | 0.125->32 |
| Fosfomycin | >32 | >32 | >32 | 32->32 |

Abbreviations: CPE: carbapenemase-producing Enterobacteriaceae; BSBL: Enterobacteriaceae with a broad-spectrum β-lactamase; MRSA: methicillin-resistant *Staphylococcus aureus*; MSSA: methicillin-sensitive *Staphylococcus aureus*; GRE: glycopeptide-resistant *enterococci*.

Example 3: Reaction Medium According to the Invention for Detecting Bacteria of the Genus *Salmonella*

3.1 Composition of the Medium

The present Example 3 aims to compare the detection specificity of a reaction medium according to the invention, intended to detect bacteria of the genus *Salmonella*, namely the medium "modified chromID *Salmonella*" against a reference detection medium for the same bacteria, namely the medium "chromID *Salmonella*".

The respective compositions of the reaction medium according to the present invention and of the reference reaction medium are presented below, within Table 2.

TABLE 2

Compositions of the reaction medium according to the invention and of the reference medium

| Modified chromID *Salmonella* medium = beta | | ChromID *Salmonella* medium = IDSalm | |
|---|---|---|---|
| | g/L | | g/L |
| Peptones | 6.25 g | Peptones | 6.25 g |
| Glucose | 0.5 | Glucose | 0.5 |
| Bile salts | 1.5 | Bile salts | 1.5 |
| NaCl | 5.0 | NaCl | 5.0 |
| Buffer | 0.2 | Buffer | 0.2 |
| Agar | 14.0 | Agar | 14.0 |
| Chromogenic mixture | 9.6 | Chromogenic mixture | 9.6 |
| β-Cl-Alafosfalin | 0.002 | | |

3.2 Results

The results obtained are presented in Table 3 below:

TABLE 3

| | | IDSalm | | beta | |
|---|---|---|---|---|---|
| Reference # | Bacteria | Growth | Colour | Growth | Colour |
| | *Salmonella* montevideo | ++ | ++ Mauve | ++ | ++ Mauve |
| | *Salmonella* seftenberg | ++ | ++ Mauve | ++ | ++ Mauve |
| | *Salmonella* choleraesuis | ++ | ++ Mauve | ++ | ++ Mauve |
| | *Salmonella* meleagridis | ++ | ++ Mauve | ++ | ++ Mauve |
| NCTC 12023 | *Salmonella* typhimurium | ++ | ++ Mauve | ++ | ++ Mauve |
| | *Salmonella* berta | ++ | ++ Mauve | ++ | ++ Mauve |
| | *Salmonella* stanley | ++ | ++ Mauve | ++ | ++ Mauve |
| NCTC 6676 | *Salmonella* enteritidis | ++ | ++ Mauve | ++ | ++ Mauve |
| | *Salmonella* simsburg | ++ | ++ Mauve | ++ | ++ Mauve |
| | *Salmonella* lexington | ++ | ++ Mauve | ++ | ++ Mauve |
| | *Salmonella* limete | ++ | ++ Mauve | ++ | ++ Mauve |
| | *Salmonella* corvalis | ++ | ++ Mauve | ++ | ++ Mauve |
| | *Salmonella* haifa | ++ | ++ Mauve | ++ | ++ Mauve |
| | *Salmonella* zanzibar | ++ | ++ Mauve | ++ | ++ Mauve |
| | *Salmonella* indiana | ++ | ++ Mauve | ++ | ++ Mauve |
| | *Salmonella* javiana | ++ | ++ Mauve | ++ | ++ Mauve |
| NCTC 11304 | *Salmonella* indiana | ++ | ++ Mauve | ++ | ++ Mauve |
| | *Salmonella* oranienburg | ++ | ++ Mauve | ++ | ++ Mauve |
| NCTC 4840 | *Salmonella* poona | ++ | ++ Mauve | ++ | ++ Mauve |
| | *Salmonella* tennessee | ++ | ++ Mauve | ++ | ++ Mauve |
| | *Salmonella* emek | ++ | ++ Mauve | ++ | + Mauve |
| | *Salmonella* virohrady | ++ | ++ Mauve | ++ | ++ Mauve |
| | *Salmonella* java | ++ | ++ Mauve | ++ | ++ Mauve |
| | *Salmonella* augustenborg | ++ | ++ Mauve | ++ | ++ Mauve |
| | *Salmonella* alachia | ++ | ++ Mauve | ++ | ++ Mauve |
| | *Salmonella* panama | ++ | ++ Mauve | ++ | ++ Mauve |
| | *Salmonella* virchow | ++ | ++ Mauve | ++ | ++ Mauve |
| | *Salmonella* paratyphi | ++ | ++ Mauve | ++ | ++ Mauve |
| | *Salmonella* orthmarschen | ++ | ++ Mauve | ++ | ++ Mauve |
| | *Salmonella* vilvorde | ++ | ++ Mauve | ++ | ++ Mauve |
| | *Salmonella* gallinarum | + | +/− Mauve | + | +/− Mauve |
| NCTC 8385 | *Salmonella* typhi | ++ | + Mauve | + | − |
| NCTC 9528 | *K. pneumoniae* | ++ | ++ Blue | ++ | ++ Blue |
| NCTC 11936 | *E. cloacae* | ++ | + Blue | ++ | + Blue |
| NCTC 10322 | *S. marcescens* | ++ | ++ Blue | ++ | ++ Blue |
| NCTC 10662 | *P. aeruginosa* | − | − | − | − |
| NCTC | *S. maltophilia* | +/− | − | +/− | − |
| NCTC 19606 | *A. baumannii* | ++ | ++ Mauve | ++ | ++ Mauve |
| NCTC 7475 | *P. rettgeri* | − | − | − | − |
| WILD 462213 | *M. morganii* | ++ | − | ++ | − |
| 69052 | *Escherichia coli* | ++ | − | ++ | − |
| 68957 | *Escherichia coli* | ++ | − | ++ | − |
| 68958 | *Escherichia coli* | ++ | +/− Blue | ++ | − |
| 68805 | *Escherichia coli* | ++ | +/− Blue | + | − |
| 69367 | *Escherichia coli* | + | +/− Blue | + | − |
| 69371 | *Escherichia coli* | ++ | − | ++ | − |
| 69035 | *Escherichia coli* | ++ | V. Blue | ++ | − |
| 69051 | *Escherichia coli* | + | +/− Blue | + | − |
| 69017 | *Escherichia coli* | ++ | − | ++ | − |
| 69148 | *Escherichia coli* | − | − | − | − |
| 68880 | *Escherichia coli* | ++ | − | ++ | − |
| 68886 | *Escherichia coli* | ++ | − | ++ | − |
| 69102 | *Escherichia coli* | ++ | − | ++ | − |
| 69157 | *Escherichia coli* | 1 colony − | | +/− | − |
| 69285 | *Escherichia coli* | 2 colonies − | | +/− | − |
| 69130 | *Escherichia coli* | ++ | − | ++ | − |
| 69134 | *Escherichia coli* | ++ | − | ++ | − |
| 69135 | *Escherichia coli* | + | − | + | − |
| 69174 | *Escherichia coli* | − | − | − | − |
| 69176 | *Escherichia coli* | +/− | +/− Blue | +/− | − |

3.3 Conclusion

The addition of β-Cl-Alafosfalin to the chromID *Salmonella* medium makes it possible to selectively inhibit the osidase activities of the strains of *Escherichia coli*. Insofar as it proves easier to detect one or more mauve colonies in a medium of colourless colonies than in a medium of blue colonies, if a salmonella strain is present in low concentration in mixture with one or more *Escherichia coli* strains, it becomes significantly easier to detect it in the reaction medium of the present invention.

Example 4: Synthesis Method of Antimicrobial Compound G According to the Invention (FIG. 2): L-Norvalinyl-β-chloro-L-alanyl-D/L-fosfalin L-Norvalinyl-β-chloro-L-alanyl-D/L-fosfalin (L-Nva-β-Cl-L-Ala-D/L-fosfalin) is represented by the following formula:

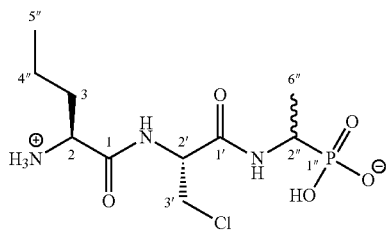 [SMILES: CCC[C@H]([NH3+])C(=O)N[C@@H](CCl)C(=O)NC(C)P(=O)([O-])O]

The synthesis of this antimicrobial compound is detailed below. The corresponding synthesis method is moreover illustrated in FIG. 4.

As represented in FIG. 4, the abovementioned compound according to the invention was synthesised from $^t$BOC-L-norvaline (commercially available), β-chloro-L-alanine O-benzyl ester (the synthesis of which is represented in FIG. 5) and D/L-fosfalin diethyl ester (the synthesis of which is represented in FIG. 6).

4.1 Synthesis of the Reaction Intermediate β-chloro-L-alanine O-benzyl ester 32 from the Compound $^t$BOC-L-serine 41 (As Illustrated in FIG. 5)

4.1.1 Synthesis of (S)-benzyl 2-((tert-butoxycarbonyl)amino)-3-hydroxypropanoate ($^t$BOC-L-serine O-benzyl ester) 43 [9]

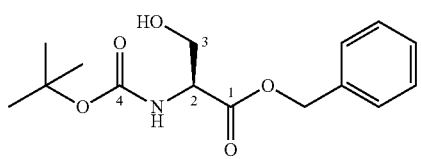 [SMILES: CC(C)(C)OC(=O)N[C@@H](CO)C(=O)OCc1ccccc1]

Some $^t$BOC-L-serine (commercially available) 41 (30 mmol, 6.16 g) was dissolved in dry benzene (100 mL), to which some 1,8-diazabicyclo[5,4,0]undec-7-ene (DBU) (36 mmol, 5.5 mL) and some benzyl bromide 42 (36 mmol, 4.4 mL) was then added. The solution was agitated overnight at ambient temperature under nitrogen, and the solvent was later eliminated under low pressure to give an off-white liquid residue. Some ethyl acetate (200 mL) was added, and the contents of the flask were ultrasound-treated, then washed with a 1M solution of HCl (2×50 mL), a 10% weight/volume aqueous solution of $K_2CO_3$ (2×50 mL) and brine (2×50 mL). The organic layer was dried on $MgSO_4$, filtered, concentrated under vacuum and purified by column chromatography [petrol/ethyl acetate (1:1)] to give the product 43 in the form a white solid (8.05 g, 27.3 mmol, 91%); m.p. 61-66° C. (lit. m.p. [10] 59-60° C.); $[α]^{21}_D$ –18.5° (c 1.0, $CH_3OH$); $ν_{max}$/cm$^{-1}$ 3419 (NH), 3361 (OH), 2978 (CH), 1758 (C=O), 1668 (C=O), 1524 (NH bend), 1155 (C—O), 1068 (C—O); $^1$H NMR (300 MHz, DMSO) $δ_H$ 1.38 (9H, s, $C(CH_3)_3$), 3.68 (2H, t, J=6.0 Hz, $CH_2OH$), 4.10-4.16 (1H, m, CH-2), 4.91 (1H, t, J=6.0 Hz, OH), 5.10 (1H, d, J=12.0 Hz, $OCH_{2a}Ar$), 5.17 (1H, d, J=12.0 Hz, $OCH_{2b}Ar$), 6.97 (1H, d, J=9.0 Hz, NH), 7.32-7.38 (5H, m, 5×$CH_{Ar}$); $^{13}$C NMR (75 MHz, DMSO) $δ_C$ 28.6 ($C(CH_3)_3$), 57.0 (CH-2), 61.8 ($CH_2$-3), 66.2 ($OCH_2Ar$), 78.8 ($C(CH_3)_3$), 128.0 ($CH_{Ar}$), 128.4 ($CH_{Ar}$), 128.8 ($CH_{Ar}$), 136.5 ($CH_{Ar}$ quat), 155.8 (C-4, quat), 171.4 (C-1, quat).

4.1.2 Synthesis of (R)-benzyl 2-((tert-butoxycarbonyl)amino)-3-chloropropanoate ($^t$BOC-β-chloro-L-alanine O-benzyl ester) 44 [11]

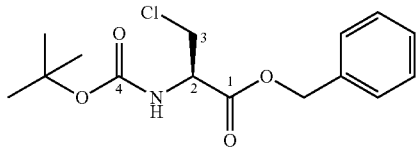

((S)-benzyl 2-((tert-butoxycarbonyl)amino)-3-hydroxypropanoate 43 (25 mmol, 7.39 g), obtained in step 4.1.1 above, was dissolved in dry DCM (100 mL), and then some trichloro-acetonitrile (50 mmol, 5.0 mL) was added. The solution was agitated at ambient temperature for 2 hours. Some triphenylphosphine (50 mmol, 13.15 g) in dry DCM (50 mL) was added slowly to this solution. The solution thus obtained was agitated overnight at ambient temperature under nitrogen. Some brine (100 mL) was added to stop the reaction. After separation, the organic layer was washed with brine (3×60 mL), dried on $MgSO_4$, filtered and concentrated under vacuum to give a liquid orange residue. The residue was purified by column chromatography [petrol/ethyl acetate (7:3)] to give the product 44 in the form of an off-white solid (7.41 g, 23.6 mmol, 95%); m.p. 53-58° C.; $[α]^{22}_D$ –23.0° (c 1.0, $CH_3OH$); $ν_{max}$/cm$^{-1}$ 3365 (NH), 2917 (CH), 1727 (C=O), 1679 (C=O), 1522 (NH bend), 1181 (C—O), 1158 (C—O); $^1$H NMR (300 MHz, CDCl$_3$) $δ_H$ 1.45 (9H, s, $C(CH_3)_3$), 3.85 (1H, dd, J=12.0 Hz, 3.0 Hz, $CH_{2a}$-3), 3.99 (1H, dd, J=12.0 Hz, 3.0 Hz, $CH_{2b}$-3), 4.74 (1H, m, CH-2), 5.20 (1H, d, J=12.0 Hz, $OCH_{2a}Ar$), 5.25 (1H, d, J=12.0 Hz, $OCH_{2b}Ar$), 5.44 (1H, d, J=6.0 Hz, NH), 7.33-7.38 (5H, m, 5×$CH_{Ar}$); $^{13}$C NMR (75 MHz, CDCl$_3$) $δ_C$ 27.3 ($C(CH_3)_3$), 44.5 ($CH_2$-3), 53.5 (CH-2), 66.8 ($OCH_2Ar$), 79.5 ($C(CH_3)_3$), 127.3 ($CH_{Ar}$), 127.6 ($CH_{Ar}$), 127.6 ($CH_{Ar}$), 133.9 ($CH_{Ar}$ quat), 154.0 (C-4, quat), 168.0 (C-1, quat); CHN [Found: C, 57.71; H, 6.46; N, 4.18. $C_{15}H_{20}ClNO_4$ requires C, 57.42; H, 6.42; N, 4.46%].

4.1.3 Synthesis of (R)-1-(benzyloxy)-3-chloro-1oxopropan-2-aminium chloride (β-chloro-L-alanine hydrochloride) 32

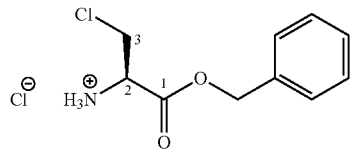 [SMILES: [Cl-] ; [NH3+][C@@H](CCl)C(=O)OCc1ccccc1]

Compound 44 (10 mmol, 3.14 g), obtained in step 4.1.2. above, was dissolved in a 2M solution of HCl in ether (200 mL). The solution was agitated at ambient overnight. The solid thus obtained was filtered and washed with diethyl ether to give the product 32 in the form of a white solid (2.36 g, 9.5 mmol, 95%); m.p. 145° C. (secondary); $v_{max}/cm^{-1}$ 2848 (CH), 1749 (C=O), 1593 (Ar C—C), 1490 (Ar C—C), 1231 (C—O); $^1H$ NMR (300 MHz, DMSO) $\delta_H$ 4.16 (1H, dd, J=12.0 Hz, 3.0 Hz, $CH_{2a}$-3), 4.22 (1H, dd, J=12.0 Hz, 3.0 Hz, $CH_2$b-3), 4.77 (1H, t, J=3.0 Hz, CH-2), 5.26 (1H, d, J=12.0 Hz, $OCH_{2a}$Ar), 5.31 (1H, d, J=15.0 Hz, $OCH_{2b}$Ar), 7.33-7.46 (5H, m, 5×$CH_{Ar}$), 9.09 (3H, br, $NH_3^+$); $^{13}C$ NMR (75 MHz, DMSO) $\delta_C$ 43.3 ($CH_2$-3), 53.5 (CH-2), 68.0 ($OCH_2$Ar), 128.6 ($CH_{Ar}$), 128.8 ($CH_{Ar}$), 128.9 ($CH_{Ar}$), 135.4 ($CH_{Ar}$ quat), 167.0 (C-1, quat); CHN [Found: C, 47.16; H, 5.43; N, 5.43. $C_{10}H_{13}Cl_2NO_2.0.2H_2O$ requires C, 47.34; H, 5.32; N, 5.52%].

4.2 Synthesis of (R)-benzyl 2-((S)-2-((tert-butoxycarbonyl)amino)pentanamido)-3-chloropropanoate ($^t$BOC-L-Norvalinyl-β-chloro-L-alanine O-benzyl ester) 33

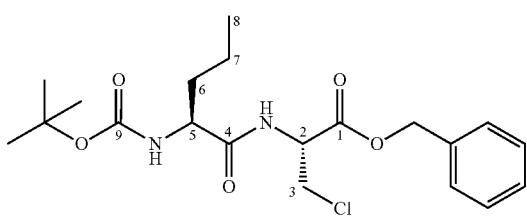 [SMILES: CCC[C@H](NC(=O)OC(C)(C)C)C(=O)N[C@@H](CCl)C(=O)OCc1ccccc1]

Some $^t$BOC-L-Norvaline (commercially available) 31 (6.0 mmol, 1.31 g) was dissolved in dry THF (50 mL) and some N-methyl morpholine (6.0 mmol, 0.66 mL) was added. The solution was then cooled to 0° C. and some isobutyl chloroformate (6.0 mmol, 0.78 mL) was added dropwise. The mixture was agitated at 0° C. under nitrogen for 1 hour. Some (R)-1-(benzyloxy)-3-chloro-1oxopropan-2-aminium chloride (chloride salt of β-Cl-L-alanine benzyl ester) 32 (5.4 mmol, 1.36 g), obtained in step 4.1.3 above, in dry DCM (30 mL) previously neutralised by N-methyl morpholine (5.4 mmol, 0.59 mL) at 0° C. was added to the agitated solution. The solution thus obtained was agitated overnight under nitrogen at ambient temperature. The solution was filtered and concentrated under vacuum. The residue was dissolved in DCM (60 mL) and washed with a 10% weight/volume solution of citric acid (2×25 mL), then with water (25 mL). The organic layer was dried on $MgSO_4$, filtered and concentrated under vacuum to give a yellow liquid which was purified by column chromatography [petrol/ethyl acetate (7:3)] to give the product 33 in the form of a white solid (1.74 g, 4.2 mmol, 78%); m.p. 95-98° C.; $[\alpha]^{25}_D$–25.0° (c 1.0, $CH_3OH$); $v_{max}/cm^{-1}$ 3327 (NH), 2960 (CH), 1738 (C=O), 1668 (C=O), 1518 (NH bend), 1169 (C—O); $^1H$ NMR (300 MHz, $CDCl_3$) $\delta_H$ 0.92 (3H, t, J=9.0 Hz, $CH_3$-8), 1.35-1.45 (11H, [m, $CH_2$-7], [s, $C(CH_3)_3$]), 1.52-1.65 (1H, m, $CH_{2a}$-6), 1.75-1.82 (1H, m, $CH_{2b}$-6), 3.89 (1H, dd, J=12.0 Hz, 3.0 Hz, $CH_{2a}$-3), 3.99 (1H, dd, J=12.0 Hz, 3.0 Hz, $CH_{2b}$-3), 4.11-4.15 (1H, m, CH-5), 4.96-5.00 (2H, [m, CH-2], [m, $HNCO_2$]), 5.20 (1H, d, J=12.0 Hz, $OCH_{2a}$ Ar), 5.25 (1H, d, J=12.0 Hz, $OCH_{2a}$—Ar), 6.97 (1H, d, J=6.0 Hz, HNCO), 7.33-7.37 (5H, m, 5×$CH_{Ar}$); $^{13}C$ NMR (75 MHz, $CDCl_3$) $\delta_C$ 12.7 ($CH_3$-8), 17.8 ($CH_2$-7), 27.3 ($C(CH_3)_3$), 33.4 ($CH_2$-6), 43.8 ($CH_2$-3), 52.2 (CH-2), 53.4 (CH-5), 67.0 ($OCH_2$Ar), 79.3 ($C(CH_3)_3$), 127.4 ($CH_{Ar}$), 127.6 ($CH_{Ar}$), 127.7 ($CH_{Ar}$), 133.8 ($CH_{Ar}$, quat), 154.5 (C-9, quat), 167.5 (C-1, quat), 171.2 (C-4, quat); CHN [Found: C, 58.49; H, 7.22; N, 6.81. $C_{20}H_{29}ClN_2O_5$ requires C, 58.18; H, 7.08; N, 6.78%]; HRMS (nanospray ionisation) calculated for $(C_{20}H_{30}ClN_2O5)+413.1838$, found $MH^+$ 413.1837.

4.3 Synthesis of (R)-2-((S)-2-((tert-butoxycarbonyl)amino)pentanamido)-3-chloropropanoic acid ($^t$BOC-L-norvalinyl-β-chloro-L-alanine) 34

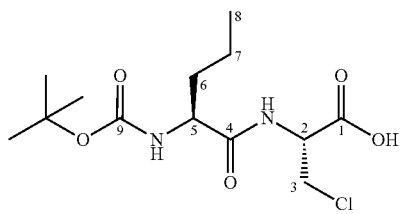 [SMILES: CCC[C@H](NC(=O)OC(C)(C)C)C(=O)N[C@@H](CCl)C(=O)O]

The product 33, (1.8 mmol, 0.75 g), obtained in step 4.2 above, was dissolved in methanol (60 mL) and added to the stainless steel pressure vessel. 10% palladium on charcoal (0.0941 g) was added and the solution thus obtained was agitated at 3.5 bar $H_2$ pressure at ambient temperature for 72 hours. The catalyst was eliminated by filtration on Celite, washed with methanol and concentrated under vacuum to give the product 34 in the form of a light yellow solid (0.573 g, 1.78 mmol, 99%); m.p. 59-63° C.; $[\alpha]^{25}_D$ –12.0° (c 1.0, $CH_3OH$); $v_{max}/cm^{-1}$ 3313 (NH), 2964 (CH), 1655 (C=O), 1509 (NH bend), 1161 (C—O); $^1H$ NMR (300 MHz, $CDCl_3$) $\delta_H$ 0.87 (3H, t, J=4.2 Hz, $CH_3$-8), 1.38 (11H, [m, $CH_2$-7], [s, $C(CH_3)_3$]), 1.51-1.62 (1H, m, $CH_{2a}$-6), 1.67-1.79 (1H, m, $CH_2$b-6), 3.91 (2H, m, $CH_2$-3), 4.19 (1H, m, CH-5), 4.85 (1H, m, CH-2), 5.20 (1H, m, NH carbamate), 6.45 (1H, br, OH), 7.25 (1H, m, NH amide); $^{13}C$ NMR (75 MHz, $CDCl_3$) $\delta_C$ 12.7 ($CH_3$-8), 17.9 ($CH_3$-7), 27.3 ($C(CH_3)_3$), 33.6 ($CH_2$-6), 43.4 (CH-3), 52.4 (CH-2), 53.2 (CH-5), 79.7 ($C(CH_3)_3$), 155.1 (C-9, quat), 170.7 (C-1/4, quat), 172.0 (C-1/4, quat); CHN [Found: C, 48.77; H, 7.61; N, 8.22. $C_{13}H_{23}ClN_2O_5$ requires C, 48.37; H, 7.18; N, 8.68%].

4.4 Synthesis of the reaction intermediate D/L-fosfalin diethyl ester 35

As represented in FIG. 6, D/L-fosfalin diethyl ester 35 was synthesised from N-phenylthio-urea 53, triphenylphosphite 52 and acetaldehyde 51 under acidic conditions, according to the Kudzin and Stec method 191 The synthesis of this reaction intermediate is detailed below.

4.4.1 Synthesis of (β)-(1-aminoethyl)phosphonic acid (D/L-fosfalin) 54 [12]

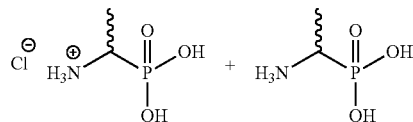

Some N-phenylthio-urea 53 (40 mmol, 6.10 g) was dissolved in glacial acetic acid (20 mL). Acetaldehyde 51 (60 mmol, 3.40 mL) was added dropwise, and then triphenyl phosphite 52 (40 mmol, 11 mL) was added. The solution was agitated at ambient temperature for 5 mins, and then heated to reflux at 85° C. for 1 hour. A mixture of glacial acetic acid (2 mL) and hydrochloric acid (37%, 20 mL) was added and the reaction was heated to reflux overnight at 145° C. The solution was cooled at ambient temperature, transferred and washed with ethanol in a 500 mL round-bottomed flask. A small quantity of fosfalin hydrochloride salt was obtained by filtration and the filtrate was concentrated under vacuum to give a dark orange liquid residue. The residue was dissolved in a minimum quantity of ethanol (20 mL) and propylene oxide (120 mL) was added to produce a white precipitate. The white solid was filtered under nitrogen and dried in a desiccator (on phosphorus pentoxide) for 3 days, which was followed by recrystallisation from hot water/ethanol to give the zwitterion product 54 in the form of a white solid (4.39 g, 35 mmol, 88%); m.p. 265-268° C. (s) (lit. m.p. [13] 271-275° C.); $v_{max}/cm^{-1}$ 2910 (br OH), 1616 (P—OH), 1532 (NH bend), 1143 (P=O), 1035 (P—O), 930 (P—O); $^1$H NMR (500 MHz, D$_2$O) $\delta_H$ 1.47 (3H, dd, $J_{P-H}$=14.9 Hz and $J_{H-H}$=7.3 Hz, CH$_3$), 3.40 (1H, m, CH); $^{13}$C NMR (125 MHz, D$_2$O) $\delta_C$ 13.5 (CH$_3$, d, $J_{P-C}$=2.7 Hz), 44.7 (CH, d, $J_{P-C}$=144.2 Hz).

4.4.2 Synthesis of diethyl (1-(2,2,2-trifluoro-acetamido)ethyl) phosphonate 56 [14]

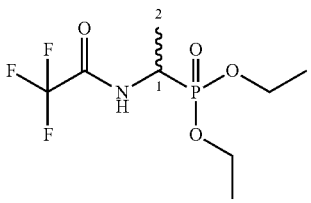

Some 1-aminoethylphosphonic acid 44 (40 mmol, 6.47 g), obtained in step 4.4.1. above, was added to a mixture of trifluoroacetic acid (5 mL) and trifluoroacetic anhydride (25 mL). The solution was agitated and heated to reflux at 60° C. After 1 hour, the solution was cooled and triethyl orthoformate (150 mL) was added slowly. The solution was heated to reflux at 110° C. for 2 hours, and then cooled to ambient temperature. The solvent was eliminated under vacuum to give a brown solid. The solid was redissolved in DCM and purified by column chromatography [DCM/MeOH (9:1)] to give the product 56 in the form of an off-white solid (11.00 g, 39.6 mmol, 99%); m.p. 98-103° C. (s) (lit m.p.$^3$ 101-102° C.); $v_{max}/cm^{-1}$ 3202 (NH), 1715 (C=O), 1565 (NH bend), 1210 (P=O), 1011 (C—F), 968 (P—O); $^1$H NMR (300 MHz, CDCl$_3$) $\delta_H$ 1.23 (3H, t J=6.0 Hz, OCH$_2$CH$_3$-a), 1.28 (3H, t J=9.0 Hz, OCH$_2$CH$_3$-b), 1.38 (3H, dd, $J_{P-H}$=15.0 Hz and $J_{H-H}$=6.0 Hz, CH$_3$-2), 3.98-4.13 (4H, m, 2×OCH$_2$CH$_3$), 4.32-4.47 (1H, m, CH-1), 8.11 (1H, d, J=9.0 Hz, NH); $^{13}$C NMR (75 MHz, CDCl$_3$) $\delta_C$ 13.7 (CH$_3$-2), 15.2 (OCH$_2$CH$_3$, d, $J_{P-C}$=2.3 Hz), 15.3 (OCH$_2$CH$_3$, d, $J_{P-C}$=1.5 Hz), 40.8 (CH-1, d, $J_{P-C}$=159.0 Hz), 61.8 (OCH$_2$CH$_3$, d, $J_{P-C}$=6.8 Hz), 62.2 (OCH$_2$CH$_3$, d, $J_{P-C}$=7.5 Hz), 114.9 (CF$_3$, q, $J_{F-C}$=285.8 Hz), 156.0 (C=O, q, $J_{F-C}$=6.0 Hz); $^{31}$P-$^1$H$_{decoup}$ NMR (121 MHz, CDCl$_3$) $\delta_P$ 23.0; $^{19}$F-$^1$H$_{decoup}$ NMR (282 MHz, CDCl$_3$) $\delta_P$-75.5.

4.4.3 Synthesis of (β)-diethyl (1-aminoethyl)phosphonate (D/L-fosfalin diethyl ester) 35 [15]

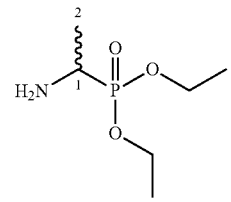

Diethyl (1-(2,2,2-trifluoro-acetamido)ethyl)phosphonate 56 (20 mmol, 5.55 g), obtained in step 4.4.2. above, was dissolved in ethanol (200 mL) and sodium borhydrate (200 mmol, 7.57 g) was slowly added. The mixture thus obtained was agitated at ambient temperature for 1 hour, and then heated to reflux (90° C.) for 3 hours. The solution was cooled to ambient temperature and the solvent was eliminated under low pressure to give a white solid residue. The residue was treated with a saturated solution of NaHCO$_3$ (96 g/L) (150 mL) and extracted in DCM (6×50 mL). The organic layer was dried on MgSO$_4$ and filtered. The filtrate was concentrated under vacuum to give a light yellow liquid, and purified by column chromatography [DCM/MeOH (9.0:1.0)] to give the product 35 in the form of a yellow liquid (2.52 g, 13.9 mmol, 70%); $v_{max}/cm^{-1}$ 3431 (NH), 2980 (CH), 1215 (P=O), 1020 (P—O), 957 (P—O); $^1$H NMR (300 MHz, CDCl$_3$) $\delta_H$1.19-1.30 (9H, [dd, $J_{P-H}$=17.4 Hz, 7.2 Hz, CH$_3$-2], [t, J=7.2 Hz, 2×OCH$_2$CH$_3$], 1.65 (2H, br, NH$_2$), 2.99-3.09 (1H, m, CH-1), 4.02-4.14 (4H, m, 2×OCH$_2$CH$_3$); $^{13}$C NMR (75 MHz, CDCl$_3$) $\delta_C$ 15.5 (OCH$_2$CH$_3$-a), 15.6 (OCH$_2$CH$_3$-b), 16.3 (CH$_3$-2), 43.3 (CH-1, d, $J_{P-C}$=148.5 Hz), 61.1 (OCH$_2$CH$_3$-a, d, $J_{P-C}$=1.5 Hz), 61.2 (OCH$_2$CH$_3$-b, d, $J_{P-C}$=1.5 Hz); $^{31}$P-$^1$H$_{decoup}$ NMR (121 MHz, CDCl$_3$) $\delta_P$29.6.

4.5 Synthesis of tert-butyl ((2S-1-(((2R)-3-chloro-1-((1-(diethoxyphosphoryl)ethyl)amino)-1-oxopropan-2-yl)amino)-1-oxopentan-2-yl)carbamate ($^t$BOC-L-norvalinyl-β-chloro-L-alanyl-D/L-fosfalin diethyl ester) 36

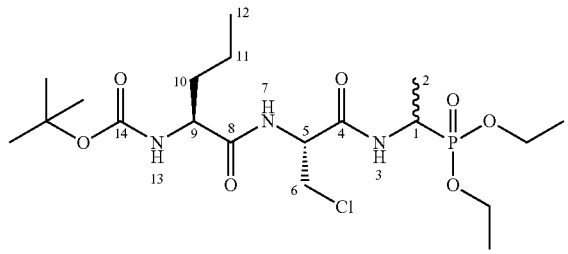 [SMILES: CCC[C@H](NC(=O)OC(C)(C)C)C(=O)N[C@@H](CCl)C(=O)NC(C)P(=O)(OCC)OCC]

(R)-2-((S)-2-((tert-butoxycarbonyl)amino)pentanamido)-3-chloropropanoic acid ($^t$BOC-L-norvalinyl-β-chloro-L-alanine) 34 (1.8 mmol, 0.58 g), obtained in step 4.3 above, was dissolved in dry THF (35 mL), then N-methyl morpholine (1.9 mmol, 0.21 mL) was added. The solution was cooled to 0° C. and some isobutyl chloroformate (1.9 mmol, 0.25 mL) was added dropwise. The mixture was agitated at 0° C. for 1 hour. Some diethyl 1-aminoethylphosphonate (D/L-fosfalin diethyl ester) 35 (1.8 mmol, 0.33 g)—obtained in step 4.4.3. above—in dry THF (10 mL) was added to the agitated solution, and the solution thus obtained was agitated overnight under nitrogen at ambient temperature. The solution was filtered and concentrated under vacuum. The residue was dissolved in DCM (60 mL) and washed with a 10% weight/volume solution of citric acid (2×30 mL), 10% weight/volume potassium carbonate (30 mL) and water (30 mL). The organic layer was dried on $MgSO_4$, filtered and concentrated under vacuum to give a light yellow liquid residue. The residue was purified by column chromatography [ethyl acetate/methanol (96:4)] to give the product 36 in the form of a sticky white solid (0.45 g, 0.93 mmol, 52%); m.p. 196° C. (decomposition); $[\alpha]^{24}_D$ –22.5° (c 1.0, $CH_3OH$); $\nu_{max}$/cm$^{-1}$ 3272 (NH), 2977 (CH), 1709 (C=O), 1644 (C=O), 1530 (NH bend), 1229 (C—O), 1165 (P—O), 1019 (P—O), 972 (P—O); $^1$H NMR (300 MHz, $CDCl_3$) $\delta_H$ 0.86 (3H, t, J=6.0 Hz, $CH_3$-12), 1.17-1.38 (20H, [m, 2×$OCH_2CH_3$], [m, $CH_3$-2], [s, $C(CH_3)_3$], [m, $CH_2$-11]), 1.53-1.59 (1H, m, $CH_{2a}$-10), 1.70-1.86 (1H, m, $CH_{2b}$-10), 3.69 (1H, dd, J=12.0 Hz, 3.0 Hz, $CH_{2a}$-6), 3.91 (1H, dd, J=12.0 Hz, 3.0 Hz, $CH_{2a}$-6), 3.97-4.13 (5H, [m, 2×$OCH_2CH_3$], [m, CH-9]), 4.35-4.46 (1H, m, CH-1), 4.73-4.79 (1H, m, CH-5), 4.97-5.03 (1H, m, NH-13), 7.00-7.10 (1H, 2×d, J=9.0 Hz, 9.0 Hz, NH-7, diastereo-isomers L,L,L and L,L,D), 7.23-7.34 (1H, 2×d, J=9.0 Hz, 9.0 Hz, NH-3, diastereo-isomers L,L,L and L,L,D); $^{13}$C NMR (75 MHz, $CDCl_3$) $\delta_C$ 12.7 ($CH_3$-12), 14.5 ($CH_3$-2), 15.3, 15.5 (2×$OCH_2CH_3$), 17.9 ($CH_2$-11), 27.3 ($C(CH_3)_3$), 33.2 ($CH_2$-10), 40.4, 52.7 ($J_{P-C}$=157.5 Hz, CH-1), 43.4 ($CH_2$-6), 52.7 (CH-5), 61.4, 61.9 (2×$OCH_2CH_3$), 79.4 ($C(CH_3)_3$), 155.0 (C-14, quat), 166.8 (C-4, quat), 171.4 (C-8, quat); $^{31}$P—$^1H_{decoup}$ NMR (121 MHz, $CDCl_3$) $\delta_P$ 24.8; HRMS (nanospray ionisation) calculated for $(C_{19}H_{38}ClN_3O_7P)^+$ 486.2130, found 486.2124; CHN [Found: C, 46.51; H, 7.76; N, 8.21. $C_{19}H_{37}ClN_3O_7P$ requires C, 46.96; H, 7.67; N, 8.65%].

4.6 Synthesis of hydrogeno (1-((R)-2-((S)-2-ammoniopentanamido)-3-chloropropanamido)ethyl) phosphonate (L-Norvalinyl-β-chloro-L-alanyl-D/L-fosfalin) 37

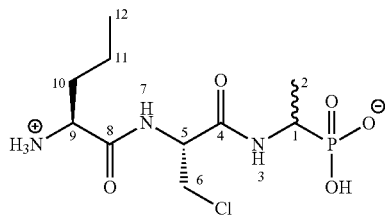 [SMILES: CCC[C@H]([NH3+])C(=O)N[C@@H](CCl)C(=O)NC(C)P(=O)([O-])O]

Some tert-Butyl ((2S)-1-(((2R)-3-chloro-1-((1-(diethoxyphosphoryl)ethyl)amino)-1-oxopropan-2-yl)amino)-1-oxopentan-2-yl)carbamate ($^t$BOC-L-norvalinyl-β-chloro-L-alanyl-D/L-fosfalin diethyl ester) 36 (2.0 mmol, 0.99 g), obtained in step 4.5. above, was dissolved in HBr and acetic acid (33%) (3.0 mL). The solution was agitated overnight at ambient temperature. Dry diethyl ether (150 mL) was added and the mixture was stored at –20° C. overnight. The solvent was decanted off and the oily brown raw product was triturated with dry diethyl ether (5×60 mL). The orange-brown hygroscopic residue was dissolved in dry methanol (5 mL), followed by the addition of excess propylene oxide. The solution was filtered and washed with diethyl ether to give a pale green solid which was later filtered to give the end product 37 in the form of a pale green solid (0.64 g, 1.94 mmol, 97%); m.p. 175° C. (secondary) $[\alpha]^{21}_D$ –2.50° (c 1.0, $H_2O$+DIEA, 9.9:0.1); $\nu_{max}$/cm$^{-1}$ 3294 (NH$^+$), 2963 (CH), 1668 (C=O), 1645 (C=O), 1538 (NH bend), 1132 (P—O), 1039 (P—O), 998 (P—O); $^1$H NMR (300 MHz, $D_2O$) $\delta_H$ 1.01 (3H, t, J=9.0 Hz, $CH_3$-12), 1.30-1.37 (3H, m, $CH_3$-2), 1.44-1.54 (2H, m $CH_3$-11), 1.90-1.98 (2H, m, $CH_2$-10), 3.91-4.15 (4H, [m, $CH_2$-6], [m, CH-9], [m, CH-1]), 4.79 (1H, m, CH-5); $^{13}$C NMR (75 MHz, $D_2O$) $\delta_C$ 12.9 ($CH_3$-12), 15.7 ($CH_3$-2), 17.6 ($CH_2$-11), 33.0 ($CH_2$-10), 43.3 ($CH_2$-6), 53.1 (CH-1, CH-9), 55.0 (CH-5), 170.4 (C-4, C-8, quat); $^{31}$P—$^1H_{decoup}$ NMR (121 MHz, $CDCl_3$) $\delta_P$ 18.5; HRMS (nanospray ionisation) calculated for $(C_{10}H_{20}ClN_3O_5P)^-$ 328.0835, found 328.0833.

Example 5: Synthesis Method of Antimicrobial Compound H According to the Invention (FIG. 2): L-methionyl-β-chloro-L-alanyl-D/L-fosfalin L-methionyl-β-chloro-L-alanyl-D/L-fosfalin (L-Met-β-Cl-L-Ala-D/L-fosfalin) is represented by the following formula:

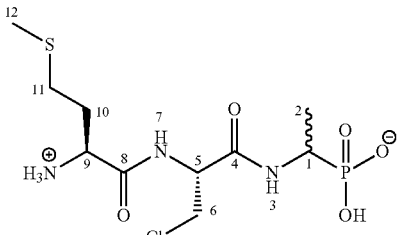

The synthesis of this antimicrobial compound is detailed below.

5.1. Synthesis of the reaction intermediate Tert-butyl((2R)-3-chloro-1-((1-(diethoxyphosphoryl) ethyl)amino)-1-oxopropan-2-yl)carbamate ($^t$BOC-β-Cl-L-Ala-D/L-Fos diethyl ester)

$^t$Boc-β-Cl-L-Ala-D/L-Fos diethyl ester is represented by the following formula:

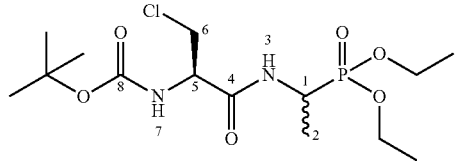 [SMILES: CCOP(=O)(OCC)C(C)NC(=O)[C@H](CCl)NC(=O)OC(C)(C)C]

Some N-methylmorpholine (7.8 mmol, 0.90 mL) was added to a suspension of $^t$BOC-β-Cl-L-Ala-OH (7.8 mmol, 1.74 g) in dry THF (60 mL) at –5° C. Some isobutyl chloroformate (7.8 mmol, 1.00 mL) was added slowly and the resulting mixture was agitated at –5° C. for 1 hour. Some diethyl 1-aminoethylphosphonate (8.6 mmol, 1.57 g) in dry THF (20 mL) was added to the agitated mixture at –5° C. The resulting mixture was agitated under nitrogen at –5° C. for 30 minutes, and then at ambient temperature overnight. The mixture was filtered and the solvent was eliminated under vacuum to give a pale yellow liquid, which was washed with 10% weight/volume citric acid (2×25 mL), 10% weight/volume potassium carbonate (25 mL) and water (25 mL). The combined organic layers were dried on magnesium sulfate, filtered and concentrated under vacuum to give a pale yellow liquid. The liquid was purified by column chromatography, using 100% DCM, and then increasing progressively to 90:10 DCM/MeOH, to give the product in the form of a yellow syrup consisting of 2 diastereoisomers, $^tBOC$-β-Cl-L-Ala-L-Fos diethyl ester and $^tBOC$-β-Cl-L-Ala-D-Fos diethyl ester (2.70 g, 7.0 mmol, 90%); $\nu_{max}/cm^{-1}$ 3261 (NH), 1713 (C=O), 1670 (C=O), 1517 (NH bend), 1225 (P=O), 1164 (P—O), 1020 (P—O), 970 (P—O); $^1$H NMR (300 MHz, CDCl$_3$) $\delta_H$ 1.15-1.39 (18H, [s, C(CH$_3$)$_3$], [m, CH$_3$-2], [m, 2×OCH$_2$CH$_3$]), 3.64-3.71 (1H, m, CH.$_{a/b}$-6), 3.89-3.96 (1H, m, CH.$_{a/b}$-6), 4.01-4.12 (4H, m, 2×OCH$_2$CH$_3$), 4.42-4.49 (2H, [m, CH-1], [m, CH-5]), 5.40 (1H, d, J=3.0 Hz, NH-3 or NH-7-A), 5.43 (1H, d, J=6.0 Hz, NH-3 or NH-7-A), 7.00 (1H, d, J=9.0 Hz, NH-3 or NH-7-A), 7.07 (1H, d, J=9.0 Hz, NH-3 or NH-7-B); $^{13}$C NMR (75 MHz, CDCl$_3$) $\delta_C$ 15.6 (d, $J_{P-C}$=5.3 Hz, CH$_3$-2), 16.3 (d, $J_{P-C}$=2.3 Hz, OCH$_2$CH$_3$), 16.5 (d, $J_{P-C}$=2.3 Hz, OCH$_2$CH$_3$), 28.3 (C(CH$_3$)$_3$) 41.2 (d, $J_{P-C}$=157.5 Hz, CH-1-A), 41.3 (d, $J_{P-C}$=156.8 Hz, CH-1-B), 44.9 (CH$_2$-6-A), 45.0 (CH$_2$-6-B), 55.3 (CH-5), 62.5 (d, $J_{P-C}$=3.0 Hz, OCH$_2$CH$_3$-A), 62.6 (d, $J_{P-C}$=3.8 Hz, OCH$_2$CH$_3$—B), 62.9 (d, $J_{P-C}$=3.0 Hz, OCH$_2$CH$_3$-A), 63.0 (d, $J_{P-C}$=3.0 Hz, OCH$_2$CH$_3$—B), 80.7 (C(CH$_3$)$_3$), 154.9 (C=O-8), 168.3 (C=O-4); $^{31}$P—$^1$H$_{decoup}$ NMR (121 MHz, CDCl$_3$) $\delta_P$ 24.8.

5.2. Synthesis of the reaction intermediate (2R)-3-chloro-1-((1-(diethoxyphosphoryl)ethyl)amino)-1-oxopropan-2-aminium chloride (β-Cl-L-Ala-D/L-Fos diethyl ester hydrochloride)

β-Cl-L-Ala-D/L-Fos diethyl ester hydrochloride is represented by the following formula:

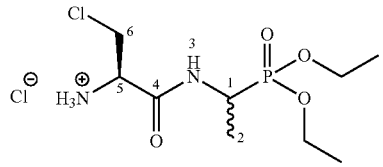 [SMILES: [Cl-] ; CCOP(=O)(OCC)C(C)NC(=O)[C@@H]([NH3+])CCl]

A solution of $^tBOC$-β-Cl-L-Ala-D/L-Fos diethyl ester (obtained in step 5.1.; 6.7 mmol, 2.59 g) in a 2M HCl solution in diethyl ether (100 mL) was agitated under nitrogen at ambient temperature overnight. The mixture was then filtered and the off-white hygroscopic solid was washed with diethyl ether. The solid was then dried overnight in a desiccator containing phosphorus (V) oxide and triturated with petrol to give the product in the form of a pale green solid consisting of 2 diastereoisomers, β-Cl-L-Ala-L-Fos diethyl ester hydrochloride and β-Cl-L-Ala-D-Fos diethyl ester hydrochloride (1.51 g, 4.7 mmol, 70%); m.p. 127-131° C. (decomp.); $\nu_{max}/cm^{-1}$ 3204 (NH), 1687 (C=O), 1562 (NH bend), 1204 (P=O), 1010 (P—O), 961 (P—O); $^1$H NMR (300 MHz, D$_2$O) $\delta_H$ 1.28 (3H, t, J=6.0 Hz, OCH$_2$CH$_3$), 1.29 (3H, t, J=6.0 Hz, OCH$_2$CH$_3$), 1.37 (3H, dd, $^3J_{P-H}$=18.0 Hz, $^3J_{H-H}$=6.0 Hz, CH$_3$-2), 3.92-4.04 (2H, m, CH$_2$-6), 4.07-4.21 (4H, m, 2×OCH$_2$CH$_3$), 4.38-4.48 (2H, [m, CH-1], [m, CH-5]); $^{13}$C NMR (75 MHz, D$_2$O) $\delta_C$ 13.7 (CH$_3$-2), 14.0 (CH$_3$-2), 15.7 (OCH$_2$CH$_3$), 15.7 (OCH$_2$CH$_3$), 41.7 (d, $J_{P-C}$=158.3 Hz, CH-1), 42.0 (d, $J_{P-C}$=157.5 Hz, CH-1), 42.4 (CH$_2$-6), 53.7 (CH-5), 53.8 (CH-5), 64.3 (d, $J_{P-C}$=6.8 Hz, OCH$_2$CH$_3$), 64.5 (d, $J_{P-C}$=6.8 Hz, OCH$_2$CH$_3$—B), 165.7 (C=O-4-A), 165.8 (C=O-4-B); $^{31}$P-$^1$H$_{decoup}$ NMR (121 MHz, CDCl$_3$) $\delta_P$ 26.1.

5.3. Synthesis of the reaction intermediate Tert-butyl((2S)-1-(((2R)-3-chloro-1-((1-(diethoxyphosphoryl)ethyl)amino)-1-oxopropan-2-yl)amino)-4-(methylthio)-1-oxobutan-2-yl)carbamate ($^tBOC$-L-Met-β-Cl-L-Ala-D/L-Fos diethyl ester)

$^tBoc$-L-Met-β-Cl-L-Ala-D/L-Fos diethyl ester is represented by the following formula:

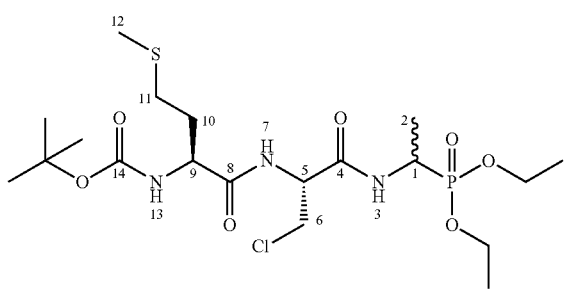 [SMILES: CCOP(=O)(OCC)C(C)NC(=O)[C@H](CCl)NC(=O)[C@H](CCSC)NC(=O)OC(C)(C)C]

Some N-methylmorpholine (3.4 mmol, 0.40 mL) was added to a solution of $^tBOC$-L-Met-OH (3.4 mmol, 0.85 g) in dry THF (60 mL). The solution was cooled to −5° C. and some isobutyl chloroformate (3.4 mmol, 0.45 mL) was added dropwise. The mixture was agitated at −5° C. for 1 hour. Some β-Cl-L-Ala-D/L-Fos diethyl ester hydrochloride obtained in step 5.2. (3.4 mmol, 1.10 g) in dry DCM (20 mL), which had been neutralised with N-methylmorpholine (3.4 mmol, 0.40 mL) at −5° C. was added dropwise to the agitated mixture. The resulting mixture was agitated under nitrogen at −5° C. for 30 minutes, and then at ambient temperature overnight. The mixture was then filtered and concentrated under vacuum, then washed with 10% weight/volume citric acid (2×25 mL), 10% weight/volume potassium carbonate (25 mL), water (25 mL) and brine (30 mL). The organic layer was dried on MgSO$_4$, filtered and the solvent was eliminated under vacuum to give a yellow liquid, which was purified by column chromatography [DCM/MeOH (95:5)] to give a colourless liquid. Recrystallisation from diethyl ether/petrol gave the product in the form of a white solid consisting of 2 diastereoisomers, $^tBOC$-L-Met-β-Cl-L-Ala-L-Fos diethyl S ester and $^tBOC$-L-Met-β-Cl-L-Ala-D-Fos diethyl ester (0.88 g, 1.7 mmol, 50%); m.p. 96-99° C.; $\nu_{max}/cm^{-1}$ 3278 (NH), 1709 (C=O), 1639 (C=O), 1523 (NH bend), 1228 (P=O), 1018 (P≥O), 970 (P≥O); $^1$H NMR (300 MHz, CDCl$_3$) $\delta_H$ 1.17-1.36 (9H, [m, CH$_3$-2], [m, 2×OCH$_2$CH$_3$]), 1.38 (9H, s, C(CH$_3$)$_3$), 1.87-2.07 (5H, [s, CH$_3$-12], [m, CH$_2$-10]), 2.48-2.54 (2H, m, CH$_2$-11), 3.71 (1H, dd, J=12.0 Hz, 6.0 Hz, CH$_{a/b}$-6), 3.88 (1H, dd, J=12.0 Hz, 6.0 Hz, CH$_{a/b}$-6), 3.99-4.13 (4H, m, 2×OCH$_2$CH$_3$), 4.20 (1H, m, CH-9), 4.37-4.47 (1H, m, CH-1), 4.78-4.84 (1H, m, CH-5), 5.39 (1H, d, J=6.0 Hz, NH-13-A), 5.41 (1H, d, J=6.0 Hz, NH-13-B), 7.15 (1H, d, J=6.0 Hz, NH-7-A), 7.24 (1H, d, J=6.0 Hz, NH-7-B), 7.52 (1H, m, NH-3); $^{13}$C NMR (75 MHz, CDCl$_3$) $\delta_C$ 14.4 (CH$_3$-2 or CH$_3$-12), 14.5 (CH$_3$-2 or CH$_3$-12), 15.4 (OCH$_2$CH$_3$), 15.5 (OCH$_2$CH$_3$), 27.3 (C(CH$_3$)$_3$), 29.2 (CH$_2$-11-A), 29.3 (CH$_2$-11-B), 30.2 (CH$_2$-10-A), 30.4 (CH$_2$-10-B), 40.3 (d, $J_{P-C}$=159.0 Hz, CH-1), 43.5 (CH$_2$-6-A), 43.7 (CH$_2$-6-B), 52.7 (CH-5), 53.1 (CH-9), 61.6 (d, $J_{P-C}$=6.8 Hz, OCH$_2$CH$_3$-A), 61.7 (d, $J_{P-C}$=6.0 Hz, OCH$_2$CH$_3$—B), 62.0 (d, $J_{P-C}$=6.8 Hz, OCH$_2$CH$_3$-A), 62.1 (d, $J_{P-C}$=7.5 Hz, OCH$_2$CH$_3$—B), 79.6 (C(CH$_3$)$_3$), 154.8 (C=O-14), 166.7 (C=O-4-A), 166.8 (C=O-4-B), 170.7 (C=O-8-A), 170.8 (C=O-8-B); $^{31}$P-$^1$H$_{decoup}$ NMR (121 MHz, CDCl$_3$) $\delta_P$ 24.8; CHN [Found: C, 44.08; H, 7.47; N, 8.18. C$_{19}$H$_{37}$ClN$_3$O$_7$PS requires C, 44.06; H, 7.20; N, 8.11%].

5.4. Synthesis of antimicrobial compound H (FIG. 2), namely the compound Hydrogeno(1-((R)-2-((S)-2-ammonio-4-(methylthio)butanamido)-3-chloropropanamido)ethyl)phosphonate (L-Met-β-Cl-L-Ala-D/L-Fos)

The antimicrobial compound L-Met-β-Cl-L-Ala-D/L-Fos is represented by the following formula:

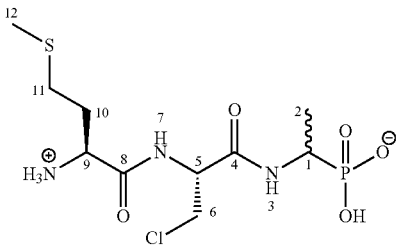 [SMILES: CSCC[C@H]([NH3+])C(=O)N[C@@H](CCl)C(=O)NC(C)P(=O)([O-])O]

A solution of $^t$BOC-L-Met-β-Cl-L-Ala-D/L-Fos diethyl ester obtained in step 5.3. (1.4 mmol, 0.71 g) in hydrogen bromide/glacial acetic acid (33%) (8.0 mL) was agitated overnight at ambient temperature. Some dry diethyl ether (70 mL) was then added and the mixture was placed in a freezer overnight. The solvent was decanted off and the raw product was triturated with dry diethyl ether (5×50 mL). The brownish-orange raw product was dissolved in methanol (5 mL) and excess propylene oxide was added. The mixture was filtered and washed with dry diethyl ether to give a green solid, which was dried in a desiccator containing phosphorus (V) oxide and recrystallised from hot water/ethanol to give the product in the form of a pale green solid consisting of 2 diastereoisomers, L-Met-β-Cl-L-Ala-L-Fos and L-Met-β-Cl-L-Ala-D-Fos (0.17 g, 0.48 mmol, 35%); m.p. 175-179° C. (decomp.); $v_{max}$/cm$^{-1}$ 3264 (NH$^+$), 2829 (large OH), 1641 (C=O), 1546 (NH bend), 1149 (P—O), 1041 (P—O), 921 (P—O); $^1$H NMR (300 MHz, D$_2$O) $\delta_H$ 1.10-1.50 (3H, m, CH$_3$-2), 2.08-2.32 (5H, [m, CH$_3$-12], [m, CH$_2$-10]) 2.61 (2H, CH$_2$-11), 3.37-4.16 (4H, [m, CH$_2$-6], [m, CH-1], [m, CH-9]), 4.48 (1H, m, CH-5); $^{13}$C NMR (75 MHz, D$_2$O) $\delta_C$ 14.0 (CH$_3$-12), 15.5 (CH$_3$-2), 28.2 (CH$_2$-11), 30.0 (CH$_2$-10), 43.3 (CH$_2$-6), 44.8 (CH-1), 52.3 (CH-9), 55.0 (CH-5), 169.4 (C=O-4 and C=O-8); $^{31}$P—$^1$H$_{decoup}$ NMR (121 MHz, CDCl$_3$) $\delta_P$ 18.7.

Example 6: Evaluation of the antibacterial activity of L-Norvalinyl-β-chloro-alanyl-D/L-fosfalin (compound G; cf. FIG. 2) and of L-Methionyl-β-chloro-alanyl-D/L-fosfalin (compound H; cf. FIG. 2) synthesised respectively according to Examples 4 and 5

6.1. Introduction

The minimum inhibitory concentrations of compounds G and H for 12 strains of Gram-negative bacteria and 6 strains of Gram-positive bacteria were determined after 22 hours of incubation using an agar dilution method as described in example 2 (cf. notably section "2.2 Materials and methods").

6.2 Results

The results obtained are presented in Table 4 below

TABLE 4

Minimum inhibitory concentrations of the antimicrobial compounds G and H against various bacteria species

| Species | Strain reference | Minimum inhibitory concentration (MIC) of compound G (μg/mL) | Minimum inhibitory concentration (MIC) of compound H (μg/mL) |
|---|---|---|---|
| *Acinetobacter baumannii* | ATCC 19606 | >8 | >8 |
| *Burkholderia cepacia* | ATCC 25416 | >8 | >8 |
| *Enterobacter cloacae* | NCTC 11936 | 4 | 4 |
| *Escherichia coli* | NCTC 10418 | 1 | 0.5 |
| *Escherichia coli* | NCTC 12241 | 0.5 | 0.5 |
| *Klebsiella pneumoniae* | NCTC 9528 | 0.5 | 0.5 |
| *Providencia rettgeri* | NCTC 7475 | >8 | >8 |
| *Pseudomonas aeruginosa* | NCTC 10662 | >8 | >8 |
| *Salmonella* typhimurium | NCTC 74 | >8 | >8 |
| *Salmonella* enteritidis | NCTC 6676 | >8 | >8 |
| *Serratia marcescens* | NCTC 10211 | 0.5 | 0.25 |
| *Yersinia enterocolitica* | NCTC 11176 | 0.25 | 0.25 |
| *Enterococcus faecalis* | NCTC 775 | 0.063 | 0.032 |
| *Enterococcus faecium* | NCTC 7171 | 1 | 1 |
| *Listeria monocytogenes* | NCTC 11994 | >8 | >8 |
| *Staphylococci epidermidis* | NCTC 11047 | 2 | 1 |
| *Staphylococcus aureus* | NCTC 6571 | 4 | 2 |
| *Staphylococcus aureus* (SARM) | NCTC 11939 | >8 | >8 |

According to the data presented in table 4 above, it clearly appears that compounds G and H are strongly inhibiting against the tested strains of certain Gram-negative bacteria species and of certain Gram-positive bacteria species, notably concerning *Escherichia coli, Klebsiella pneumoniae, Serratia marcescens, Yersinia enterocolitica, Enterococcus faecalis*, and less inhibiting against other Gram-negative and Gram-positive bacteria species, notably with regard to *Acinetobacter baumannii, Burkholderia cepacia,*

Pseudomonas aeruginosa, Salmonella typhimurium, Salmonella enteritidis, Listeria monocytogenes.

6.3 Conclusion

The very significant differences in terms of inhibitory concentration observed between various bacteria species make compounds G and H particularly well suited compounds to be incorporated in reaction media making it possible to selectively seek and/or isolate certain bacteria species in biological samples, and notably selectively seek:
Gram-negative bacteria (Gram-negative target bacteria) such as *Acinetobacter baumannii, Burkholderia cepacia, Pseudomonas aeruginosa, Salmonella typhimurium, Salmonella enteritidis*; or
Gram-positive bacteria (Gram-positive target bacteria) such as *Listeria monocytogenes*.

Example 7: Synthesis method of the Antimicrobial Compound I According to the Invention (FIG. 2): L-norvalinyl-L-alanyl-D/L-fosfalin L-norvalinyl-L-alanyl-D/L-fosfalin (L-Nva-L-Ala-D/L-fosfalin) is represented by the following formula:

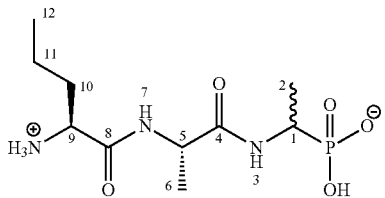 [SMILES: CCC[C@H]([NH3+])C(=O)N[C@@H](C)C(=O)NC(C)P(=O)([O-])O]

The synthesis of this antimicrobial compound is detailed below.

7.1. Synthesis of the reaction intermediate (S)-Benzyl 2-((S)-2-((tert-butoxycarbonyl)amino)pentanamido)propanoate ($^t$BOC-L-Nva-L-Ala-OBzl)

The compound $^t$BOC-L-Nva-L-Ala-OBzl is represented by the following formula:

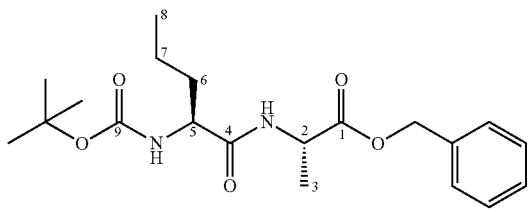 [SMILES: CCC[C@H](NC(=O)OC(C)(C)C)C(=O)N[C@@H](C)C(=O)OCc1ccccc1]

Some N-methylmorpholine (15.0 mmol, 1.65 mL) was added to a solution of $^t$BOC-L-Nva-OH (10.0 mmol, 2.17 g) in dry THF (60 mL). The solution was cooled to −5° C. and some isobutyl chloroformate (15.0 mmol, 1.95 mL) was added dropwise. The mixture was agitated at −5° C. for 1 hour. Some L-alanine benzyl ester p-toluenesulfonate salt (10.0 mmol, 3.52 g) in dry DCM (30 mL) which had been neutralised with diisopropylethylamine (15.0 mmol, 2.60 mL) at −5° C., was added dropwise to the agitated mixture. The resulting solution was agitated under nitrogen at −5° C. for 30 minutes, and then overnight at ambient temperature. The solution was filtered and concentrated under vacuum, then washed with 10% weight/volume citric acid (2×25 mL), 10% weight/volume potassium carbonate (25 mL) and water (25 mL). The organic layer was dried on $MgSO_4$, filtered and concentrated under vacuum to give a yellow hygroscopic liquid, which was purified by column chromatography [40-60 petrol/ethyl acetate (7:3)] to give the product in the form of an off-white solid (2.40 g, 6.3 mmol, 63%); m.p. 60-63° C.; $v_{max}$/cm$^{-1}$ 3299 (NH), 1743 (C=O), 1655 (C=O), 1527 (NH bend), 1245 (C—O), 1162 (C—O); $^1$H NMR (300 MHz, CDCl$_3$) $\delta_H$ 0.83 (3H, t, J=9.0 Hz, CH$_3$-8), 1.25-1.36 (14H, [d, J=6.0 Hz, CH$_3$-3], [m, CH$_2$-7], [s, C(CH$_3$)$_3$]), 1.42-1.54 (1H, m, CH$_{a/b}$-6), 1.64-1.73 (1H, m, CH$_{a/b}$-6), 4.02 (1H, m, CH-5), 4.54 (1H, pentet, J=6.0 Hz, CH-2), 4.96 (1H, d, J=9.0 Hz, NHCO$_2$), 5.07 (1H, d, J=12.0 Hz, OCH$_{a/b}$Ar), 5.12 (1H, d, J=12.0 Hz, OCH$_{a/b}$Ar), 6.56 (1H, d, J=6.0 Hz, NHCO), 7.27 (5H, m, 5×CH$_{Ar}$); $^{13}$C NMR (75 MHz, CDCl$_3$) $\delta_C$ 12.7 (CH$_3$-8), 17.3 (CH$_3$-3), 17.8 (CH$_2$-7), 27.3 (C(CH$_3$)$_3$), 33.7 (CH$_2$-6), 47.1 (CH-2), 53.4 (CH-5), 66.1 (OCH$_2$Ar), 79.0 (C(CH$_3$)$_3$), 127.1-127.6 (5×CH$_{Ar}$), 134.3 (CH$_{Ar}$ quat.), 154.6 (C=O-9), 170.8 (C=O-4), 171.5 (C=O-1); CHN [Found: C, 63.75; H, 8.37; N, 7.86. $C_{20}H_{30}N_2O_5$ requires C, 63.47; H, 7.99; N, 7.40%]; HRMS (nanospray ionisation) calculated for $(C_{20}H_{31}N_2O_5)^+$ 379.2227, found 379.2222.

7.2. Synthesis of the reaction intermediate (S)-2-((S)-2-((tert-butoxycarbonyl)amino)pentanamido)propanoic acid ($^t$BOC-L-Nva-L-Ala-OH)

The compound $^t$BOC-L-Nva-L-Ala-OH is represented by the following formula:

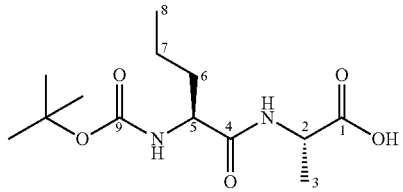 [SMILES: CCC[C@H](NC(=O)OC(C)(C)C)C(=O)N[C@@H](C)C(=O)O]

Some $^t$BOC-L-Nva-L-Ala-OBzl obtained in step 7.1. (6.0 mmol, 2.27 g) was dissolved in methanol (60 mL) and hydrogenated in the presence of 5% palladium on charcoal (0.23 g) at a pressure of 3.5 bar H$_2$ at ambient temperature overnight. The catalyst was eliminated by filtration through Celite and washed with methanol. The solution was concentrated under vacuum to give the product in the form of a white solid (1.66 g, 5.7 mmol, 96.0%); m.p. 53-58° C. (decomp.); $v_{max}$/cm$^{-1}$ 3500-2500 (br, OH), 3300 (NH), 2961 (NH), 1688 (C=O), 1655 (C=O), 1522 (NH bend), 1245 (C—O), 1164 (C—O); $^1$H NMR (300 MHz, CDCl$_3$) $\delta_H$ 0.85 (3H, t, J=9.0 Hz, CH$_3$-8), 1.27-1.39 (14H, [m, CH$_3$-3], [m, CH$_2$-7], [s, C(CH$_3$)$_3$]), 1.48-1.53 (1H, m, CH$_{a/b}$-6), 1.67-1.71 (1H, m, CH$_{a/b}$-6), 4.10 (1H, m, CH-5), 4.50 (1H, m, CH-2), 5.27 (1H, m, NHCO$_2$), 6.93 (1H, m, NHCO), 8.87 (1H, br, OH); $^{13}$C NMR (75 MHz, CDCl$_3$) $\delta_C$ 13.7 (CH$_3$-8), 18.0 (CH$_3$-3), 18.8 (CH$_2$-7), 28.3 (C(CH$_3$)$_3$), 34.5 (CH$_2$-6), 48.1 (CH-2), 54.3 (CH-5), 80.4 (C(CH$_3$)$_3$), 156.0 (C=O-9), 172.5 (C=O-4), 175.5 (C=O-1); CHN [Found: C, 54.18; H, 8.78; N, 9.62. $C_{13}H_{24}N_2O_5$ requires C, 54.15; H, 8.39; N, 9.72%]; HRMS (nanospray ionisation) calculated for $(C_{13}H_{25}N_2O_5)^+$ 289.1758, found 289.1758.

7.3. Synthesis of the reaction intermediate tert-Butyl((2S)-1-(((2S)-1-((1-(diethoxyphosphoryl)ethyl)amino)-1-oxopropan-2-yl)amino)-1-oxopentan-2-yl)carbamate (ᵗBOC-L-Nva-L-Ala-D/L-Fos diethyl ester)

ᵗBoc-L-Nva-L-Ala-D/L-Fos diethyl ester is represented by the following formula:

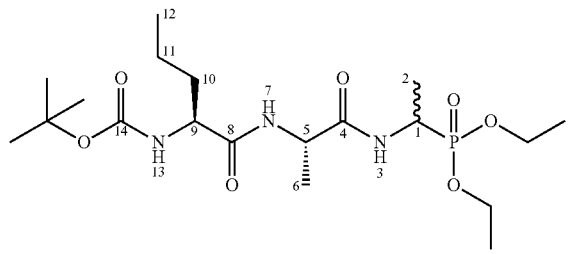 [SMILES: CCC[C@H](NC(=O)OC(C)(C)C)C(=O)N[C@@H](C)C(=O)NC(C)P(=O)(OCC)OCC]

Some N-methylmorpholine (5.3 mmol, 0.58 mL) at −5° C. was added to a solution of ᵗBOC-L-Nva-L-Ala-OH (5.0 mmol, 1.45 g; obtained from step 7.2.) in dry THF (50 mL). Some isobutyl chloroformate (5.3 mmol, 0.70 mL) was added slowly and the resulting mixture was agitated at −5° C. for 1 hour. Some diethyl 1-aminoethylphosphonate (4.8 mmol, 0.87 g; the synthesis of which is described in example 4.4 and represented in FIG. 6) in dry THF (15 mL) at −5° C. was added to the agitated mixture. The resulting mixture was agitated under nitrogen at −5° C. for 30 minutes, then at ambient temperature overnight. The mixture was filtered and the solvent was eliminated under vacuum to give a white solid, which was redissolved in DCM (50 mL) and washed with 10% weight/volume citric acid (2×25 mL), 10% weight/volume potassium carbonate (25 mL) and water (25 mL). The organic layer was dried on magnesium sulfate, filtered and concentrated under vacuum to give a white solid, which was purified by column chromatography using 100% DCM, increasing to 90:10 DCM/methanol, to give a white solid consisting of 2 diastereoisomers, ᵗBOC-L-Nva-L-Ala-L-Fos diethyl ester and ᵗBOC-L-Nva-L-Ala-D-Fos diethyl ester (1.70 g, 3.8 mmol, 78%); m.p. 165-168° C.; $v_{max}$/cm$^{-1}$ 3267 (NH), 1708 (C=O), 1638 (C=O), 1537 (NH bend), 1227 (P=O), 1019 (P—O), 966 (P—O); $^{1}$H NMR (300 MHz, CDCl$_3$) $\delta_H$ 0.85 (3H, t, J=9.0 Hz, CH$_3$-12), 1.18-1.34 (14H, [m, 2×OCH$_2$CH$_3$], [CH$_3$-2], [m, CH$_3$-6], [m, CH$_2$-11]), 1.37 (s, C(CH$_3$)$_3$), 1.47-1.54 (1H, m, CH$_{a/b}$-10), 1.65-1.73 (1H, m, CH$_{a/b}$-10), 3.98-4.12 (5H, [m, 2×OCH$_2$CH$_3$], [m, CH$_3$-5 or CH$_3$-9]), 4.33-4.44 (1H, m, CH-1), 4.48-4.54 (1H, m, CH-5 or CH-9), 5.18-5.23 (1H, d, J=6.0 Hz, NH-7 or NH-13), 5.18-5.23 (1H, d, J=6.0 Hz, NH-7 or NH-13), 6.77-6.88 (1H, d, J=6.0 Hz, NH-7 or NH-13), 6.77-6.88 (1H, d, J=6.0 Hz, NH-7 or NH-13), 7.13-7.24 (1H, d, J=9.0 Hz, 9.0 Hz, NH-3), 7.13-7.24 (1H, d, J=9.0 Hz, 9.0 Hz, NH-3); $^{13}$C NMR (75 MHz, CDCl$_3$) $\delta_C$ 12.7 (CH$_3$-12), 14.5 (CH$_3$-2, d, J$_{P—C}$=6.0 Hz), 15.3 (OCH$_2$CH$_3$-A), 15.4 (OCH$_2$CH$_3$-A), 15.5 (OCH$_2$CH$_3$—B), 15.6 (OCH$_2$CH$_3$—B), 17.6 (CH$_3$-6-A), 17.7 (CH$_3$-6-B), 17.8 (CH$_2$-11-A), 17.9 (CH$_2$-11-B), 27.3 (C(CH$_3$)$_3$), 33.8 (CH$_2$-10-A), 33.9 (CH$_2$-10-B), 39.9 (CH-1-A, d, J$_{P—C}$=157.5 Hz), 40.0 (CH-1-B, d, J$_{P—C}$=156.8 Hz), 47.7 (CH-5 or CH-9-A), 47.9 (CH-5 or CH-9-B), 53.5 (CH-5 or CH-9-A), 53.5 (CH-5 or CH-9-B), 61.4-62.0 (2×OCH$_2$CH$_3$-A and B, 4×d, J=7.5 Hz, 6.8 Hz, 7.5 Hz, 7.5 Hz), 78.9 (C(CH$_3$)$_3$), 154.7 (C=O-14), 170.6 (C=O-4 or C=O-8-A), 170.7 (C=O-4 or C=O-8-B), 171.0 (C=O-4 or C=O-8-A), 171.1 (C=O-4 or C=O-8-B); $_{31}$P—$^{1}$H$_{decoup}$ NMR (121 MHz, CDCl$_3$) $\delta_P$ 24.8; CHN [Found: C, 50.74; H, 8.55; N, 9.51. C$_{19}$H$_{38}$N$_3$O$_7$P requires C, 50.54; H, 8.48; N, 9.31%]; HRMS (nanospray ionisation) calculated for (C$_{19}$H$_{39}$N$_3$O$_7$P)$^+$ 452.2520, found 452.2518.

7.4. Synthesis of compound I, namely the compound Hydrogeno(1-((S)-2-((S)-2-ammoniopentanamido)propanamido)ethyl)phosphonate (L-Nva-L-Ala-D/L-Fos)

As indicated previously, the compound L-Nva-L-Ala-D/L-Fos is represented by the following formula:

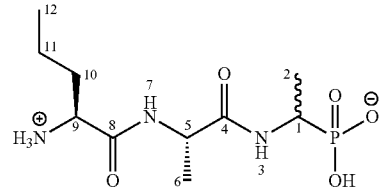 [SMILES: CCC[C@H]([NH3+])C(=O)N[C@@H](C)C(=O)NC(C)P(=O)([O-])O]

The ᵗBOC-L-Nva-L-Ala-D/L-Fos diethyl ester obtained in step 7.3. (1.6 mmol, 0.72 g) was dissolved in glacial acetic acid (30 mL) and some hydrogen bromide/acetic acid (33%) (25 mL) was added. The solution was agitated overnight at ambient temperature. Some dry diethyl ether (150 mL) was added and the mixture was placed in a freezer overnight. The solvent was decanted off and the raw product was triturated with dry diethyl ether (5×100 mL). The yellowish-orange raw product was dissolved in methanol (5 mL) and excess propylene oxide was added. The solution was filtered and washed with diethyl ether to give a pale green solid, which was recrystallized from hot water/acetone to give the product in the form of a pale green solid consisting of 2 diastereoisomers, L-Nva-L-Ala-L-Fos and L-Nva-L-Ala-D-Fos (0.22 g, 0.75 mmol, 47%); m.p. 200-210° C. (decomp.); $v_{max}$/cm$^{-1}$ 3280 (NH$^+$), 1643 (C=O), 1552 (NH bend), 1149 (P—O), 1037 (P—O), 922 (P—O); $^{1}$H NMR (300 MHz, D$_2$O) $\delta_H$ 0.96 (3H, t, CH$_3$-12), 1.29 (3H, m, CH$_3$-6) 1.42-1.40 (5H, [m, CH$_3$-2], [m, CH$_2$-11]), 1.88-1.86 (2H, m, CH$_2$-10), 4.02-4.00 (2H, [m, CH-5], [m, CH-9]), 4.34-4.39 (1H, m, CH-1); $^{13}$C NMR (75 MHz, D$_2$O) $\delta_C$ 13.4 (CH$_3$-12), 16.0 (CH$_3$-2), 17.1 (CH$_3$-6), 17.2 (CH$_3$-6), 18.1 (CH$_2$-11), 33.5 (CH$_2$-10), 50.7 (d, J$_{P—C}$=22.5 Hz, CH-1), 53.5 (CH-5 or CH-9), 170.4 (C=O-8), 174.7 (C=O-4); HRMS (nanospray ionisation) calculated for (C$_{10}$H$_{23}$N$_3$O$_5$P)$^+$ 296.1370, found 296.1373; $^{31}$P—$^{1}$H$_{decoup}$ NMR (121 MHz, CDCl$_3$) $\delta_P$ 18.5; CHN [Found: C, 37.61; H, 7.51; N, 12.91. C$_{10}$H$_{22}$N$_3$O$_5$P.1.4H$_2$O requires C, 37.48; H, 7.80; N, 13.11%].

Example 8: Synthesis method of antimicrobial compound J (FIG. 2): L-methionyl-L-alanyl-D/L fosfalin The compound L-methionyl-L-alanyl-D/L fosfalin is represented by the following formula:

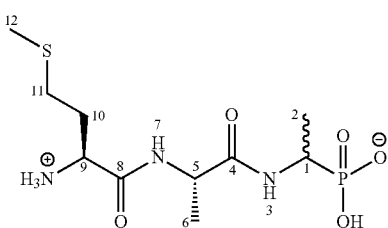 [SMILES: CSCC[C@H]([NH3+])C(=O)N[C@@H](C)C(=O)NC(C)P(=O)([O-])O]

The synthesis of this antimicrobial compound is detailed below.

8.1. Synthesis of the reaction intermediate Tert-butyl ((S)-1-(((R)-1-(diethoxyphosphoryl)ethyl)amino)-1-oxopropan-2-yl)carbamate (tBOC-L-Ala-D/L-Fos diethyl ester)

tBoc-L-Ala-D/L-Fos diethyl ester is represented by the following formula:

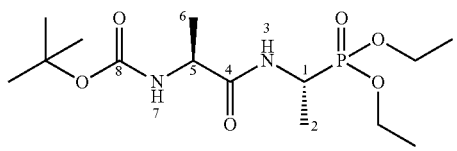 [SMILES: CCOP(=O)(OCC)[C@H](C)NC(=O)[C@H](C)NC(=O)OC(C)(C)C]

Some N-methylmorpholine (15.0 mmol, 1.65 mL) at −5° C. was added to a solution of tBOC-L-Ala-OH (10.0 mmol, 1.90 g) in dry THF (60 mL). Some isobutyl chloroformate (15.0 mmol, 1.90 mL) and the resulting mixture were agitated at −5° C. for 1 hour. Some diethyl 1-aminoethylphosphonate (10.0 mmol, 1.84 g) in dry THF (20 mL) at −5° C. was added to the agitated mixture. The resulting mixture was agitated under nitrogen at −5° C. for 30 minutes, then at ambient temperature overnight. The solution was filtered and concentrated under vacuum to give a pale yellow syrup, which was redissolved in DCM (60 mL) and washed with 10% weight/volume citric acid (2×25 mL), 10% weight/volume potassium carbonate (25 mL) and water (25 mL). The combined organic layers were dried on magnesium sulfate, filtered and concentrated under vacuum to give a pale yellow syrup, which was purified by column chromatography, using initially 100% DCM and increasing to 95:5 DCM/methanol, to give the product in the form of an off-white solid consisting of 2 diastereoisomers, tBOC-L-Ala-L-Fos diethyl ester and tBOC-L-Ala-D-Fos diethyl ester (2.49 g, 7.1 mmol, 71%); m.p. 102-105° C.; $v_{max}$/cm$^{-1}$ 3280 (NH), 1710 (C=O), 1652 (C=O), 1556 (NH bend), 1229 (P=O), 1173 (P—O), 1013 (P—O), 973 (P—O); $^1$H NMR (300 MHz, CDCl$_3$) $\delta_H$ 1.23-1.44 (21H, [s, C(CH$_3$)$_3$], [m, CH$_3$-2], [m, CH$_3$-6], [m, 2×OCH$_2$CH$_3$]), 4.06-4.23 (5H, [m, 2×OCH$_2$CH$_3$], [m, CH-5]), 4.40-4.52 (1H, m, CH-1), 5.11-5.15 (1H, 2×d, J=1.5 Hz, 1.5 Hz, NH-7), 6.70-6.78 (1H, 2×d, J=2.3 Hz, 2.3 Hz, NH-3); $^{13}$C NMR (75 MHz, CDCl$_3$) $\delta_C$ 15.6 (CH$_3$-2), 16.3 (d, J=3.0 Hz, OCH$_2$CH$_3$), 16.4 (d, J=2.3 Hz, OCH$_2$CH$_3$), 16.4 (d, J=3.8 Hz, OCH$_2$CH$_3$), 16.5 (d, J=1.5 Hz, OCH$_2$CH$_3$), 18.4 (CH$_3$-6), 28.3 (C(CH$_3$)$_3$) 40.8 (d, $J_{P-C}$=156.8 Hz, CH-1), 41.0 (d, $J_{P-C}$=156.8 Hz, CH-1), 50.0 (CH-5), 62.4-62.8 (4×d, $J_{P-C}$=6.8 Hz, 6.8 Hz, 6.8 Hz, 6.8 Hz, 2×OCH$_2$CH$_3$), 80.0 (C(CH$_3$)$_3$), 155.2 (C=O-8), 172.1 (C=O-4); CHN [Found: C, 48.22; H, 8.58; N, 7.87. C$_{14}$H$_{29}$N$_2$O$_6$P requires C, 47.72; H, 8.30; N, 7.95%].

8.2. Synthesis of the reaction intermediate (S)-1-(((R)-1-(diethoxyphosphoryl)ethyl)amino)-1-oxopropan-2-aminium chloride (L-Ala-D/L-Fos diethyl ester hydrochloride)

L-Ala-D/L-Fos diethyl ester hydrochloride is represented by the following formula:

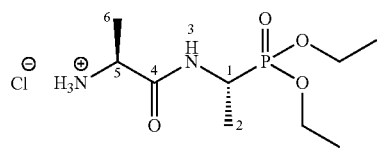 [SMILES: [Cl-] ; CCOP(=O)(OCC)[C@H](C)NC(=O)[C@H](C)[NH3+]]

A solution of tBOC-L-Ala-D/L-Fos diethyl ester (obtained in step 8.1.; 6.0 mmol, 2.13 g) in 2M HCl in diethyl ether (100 mL) was agitated under nitrogen at ambient temperature overnight. The resulting solid was collected by filtration and washed with dry diethyl ether. The off-white hygroscopic solid was dried overnight in a desiccator containing phosphorus (V) oxide and washed with petrol to give the product in the form of a pale green solid consisting of 2 diastereoisomers, L-Ala-L-Fos diethyl ester hydrochloride and L-Ala-D-Fos diethyl ester hydrochloride (1.46 g, 5.1 mmol, 84%); m.p. 102-105° C.; $v_{max}$/cm$^{-1}$ 2986 (NH$^+$), 1673 (C=O), 1555 (NH bend), 1017 (P—O), 950 (P—O); $^1$H NMR (300 MHz, d$_4$-CH$_3$OH) $\delta_H$ 1.29-1.44 (9H, [m, 2×OCH$_2$CH$_3$], [m, CH$_3$-2], 1.51 (3H, d, J=6.0 Hz, CH$_3$-6), 3.90-3.98 (1H, m, CH-5), 4.08-4.22 (4H, m, 2×OCH$_2$CH$_3$), 4.28-4.47 (1H, m, CH-1); $^{13}$C NMR (75 MHz, d$_4$-CH$_3$OH) $\delta_C$ 13.7 (CH$_3$-2-A), 14.0 (CH$_3$-2-B), 15.4 (2×OCH$_2$CH$_3$), 16.3 (CH$_3$-6), 41.1 (d, $J_{P-C}$=158.3 Hz, CH-1), 41.4 (d, $J_{P-C}$=158.3 Hz, CH-1), 48.8 (CH-5), 48.9 (CH-5), 62.7-63.0 (2×OCH$_2$CH$_3$), 169.0 (C=O-4).

8.3. Synthesis of the reaction intermediate Tert-butyl((2S)-1-(((2S)-1-((1-(diethoxyphosphoryl)ethyl)amino)-1-oxopropan-2-yl)amino-4-(methylthio)-1-oxobutan-2-yl)carbamate (tBOC-L-Met-L-Ala-D/L-Fos diethyl ester)

The compound tBOC-L-Met-L-Ala-D/L-Fos diethyl ester is represented by the following formula:

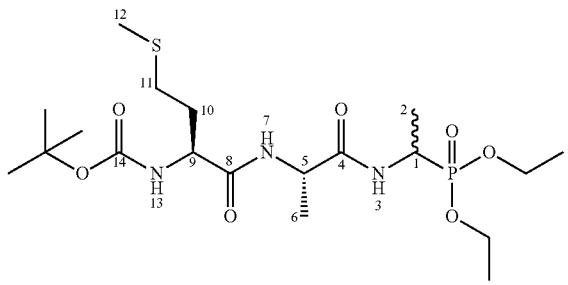 [SMILES: CCOP(=O)(OCC)C(C)NC(=O)[C@H](C)NC(=O)[C@H](CCSC)NC(=O)OC(C)(C)C]

Some N-methylmorpholine (5.1 mmol, 0.60 mL) was added to a solution of tBOC-L-Met-OH (3.4 mmol, 0.88 g) in dry THF (50 mL). The solution was cooled to −5° C. and some isobutyl chloroformate (5.1 mmol, 0.70 mL) was added dropwise. The mixture was agitated at −5° C. for 1 hour. Some L-Ala-D/L-Fos diethyl ester hydrochloride obtained in step 8.2. (3.4 mmol, 0.97 g) in dry THF (15 mL), which had been neutralised with diisopropylethylamine (5.1 mmol, 1.00 mL) at −5° C., was added dropwise to the agitated solution. The resulting solution was agitated under nitrogen at −5° C. for 30 minutes, and then overnight at ambient temperature. The solution was filtered and concentrated under vacuum, then washed with 10% weight/volume citric acid (2×25 mL), 10% weight/volume potassium carbonate (25 mL) and water (25 mL). The organic layer was dried on $MgSO_4$, filtered and concentrated under vacuum to give a yellow solid, which was purified by column chromatography [DCM/MeOH (95:5)] to give the product in the form of an off-white solid consisting of 2 diastereoisomers, $^t$BOC-L-Met-L-Ala-L-Fos diethyl ester and $^t$BOC-L-Met-L-Ala-D-Fos diethyl ester (0.53 g, 1.1 mmol, 32%); m.p. 172-176° C.; $v_{max}$/cm$^{-1}$ 3272 (NH), 1708 (C=O), 1637 (C=O), 1530 (NH bend), 1226 (P=O), 1165 (P—O), 1020 (P—O), 966 (P—O); $^1$H NMR (300 MHz, $CDCl_3$) $\delta_H$ 1.16-1.36 (12H, [m, $CH_3$-2], [m, $CH_3$-6], [m, 2×$OCH_2CH_3$]), 1.36 (9H, s, $C(CH_3)_3$), 1.82-2.01 (2H, m, $CH_2$-10), 2.04 (3H, s, $CH_3$-12), 2.49 (2H, t, J=9.0 Hz, $CH_2$-11), 4.00-4.12 (4H, m, 2×$OCH_2CH_3$), 4.21 (1H, m, CH-9), 4.33-4.43 (1H, m, CH-1), 4.45-4.53 (1H, m, CH-5), 5.40 (1H, d, J=9.0 Hz, NH-13-A), 5.44 (1H, d, J=6.0 Hz, NH-13-B), 6.85 (1H, d, J=6.0 Hz, NH-7-A), 6.92 (1H, d, J=6.0 Hz, NH-7-B), 7.07 (1H, d, J=9.0 Hz, NH-3-A), 7.16 (1H, d, J=9.0 Hz, NH-3-B); $^{13}$C NMR (75 MHz, $CDCl_3$) $\delta_C$ 14.3 ($CH_3$-2-A), 14.3 ($CH_3$-2-B), 15.4-15.5 (2×$OCH_2CH_3$), 17.7 ($CH_3$-6), 27.3 ($C(CH_3)_3$), 29.2 ($CH_2$-11-A), 29.3 ($CH_2$-11-B), 30.8 ($CH_2$-10-A), 30.8 ($CH_2$-10-B), 39.9 (d, $J_{P-C}$=156.8 Hz, CH-1-A), 40.0 (d, $J_{P-C}$=156.8 Hz, CH-1-B), 47.9 (CH-5-A), 48.0 (CH-5-B), 52.6 (CH-9), 61.5 (d, $J_{P-C}$=4.5 Hz, $OCH_2CH_3$-A), 61.6 (d, $J_{P-C}$=4.5 Hz, $OCH_2CH_3$—B), 61.7 (d, $J_{P-C}$=6.8 Hz, $OCH_2CH_3$-A), 61.9 (d, $J_{P-C}$=6.8 Hz, $OCH_2CH_3$—B), 79.1 ($C(CH_3)_3$), 154.6 (C=O-14), 170.3 (C=O-4 or C=O-8-A), 170.4 (C=O-4 or C=O-8-B), 170.5 (C=O-4 or C=O-8-A), 170.6 (C=O-4 or C=O-8-B).

8.4. Synthesis of compound J according to the invention, namely the compound Hydrogeno(1-((S)-2-((S)-2-ammonio-4-(methylthio)butanamido)propanamido)ethyl)phosphonate (L-methionyl-L-alanyl-D/L fosfalin)

As indicated previously, the compound L-methionyl-L-alanyl-D/L-fosfalin is represented by the following formula:

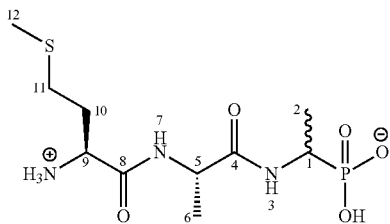

A solution of $^t$BOC-L-Met-L-Ala-D/L-Fos diethyl ester (obtained in step 8.3; 0.9 mmol, 0.43 g) in hydrogen bromide/glacial acetic acid (33%) (10 mL) was agitated overnight at ambient temperature. Some dry diethyl ether (150 mL) was added and the mixture was placed in a freezer overnight. The solvent was decanted off and the raw product was triturated with dry diethyl ether (5×100 mL). The orange brownish raw solid was dissolved in methanol (5 mL), followed by the addition of excess propylene oxide. The solution was filtered and washed with diethyl ether to give a green solid, which was recrystallized from hot ethanol and further dried in a desiccator containing phosphorus (V) oxide to give the product in the form of a pale green solid consisting of 2 diastereoisomers, L-Met-L-Ala-L-Fos and L-Met-L-Ala-D-Fos (0.13 g, 0.41 mmol, 46%); m.p. 213-217° C. (decomp.); $v_{max}$/cm$^{-1}$ 3263 (NH$^+$), 2834 (large OH), 1641 (C=O), 1552 (NH bend), 1150 (P—O), 1041 (P—O), 919 (P—O); $^1$H NMR (300 MHz, $D_2O$) $\delta_H$ 1.12-1.29 (3H, m, $CH_3$-2), 1.38 (3H, d, J=6.0 Hz, $CH_3$-6), 2.11-2.34 (5H, [s, $CH_3$-12], [m, $CH_2$-10]), 2.62 (2H, m, $CH_2$-11), 3.95-4.11 (2H, [m, CH-1], [m, CH-9]), 4.32-4.46 (1H, m, CH-5); $^{13}$C NMR (75 MHz, $D_2O$) $\delta_C$ 14.2 ($CH_3$-12), 15.5 ($CH_3$-2), 16.6 ($CH_3$-6), 28.5 ($CH_2$-11), 29.5 ($CH_2$-10), 49.9 (CH-1, CH-5 and CH-9), 169.4 (C=O-4 and C=O-8); $^{31}$P-$^1$H$_{decoup}$ NMR (121 MHz, $CDCl_3$) $\delta_P$ 20.7.

Example 9: Evaluation of the antibacterial activity of L-Norvalinyl-L-alanyl-D/L-fosfalin (compound I in FIG. 2) and of L-Methionyl-L-alanyl-D/L-fosfalin (compound J in FIG. 2) synthesised respectively according to examples 7 and 8

9.1. Introduction

As for example 6, the minimum inhibitory concentrations (MIC) of compounds I and J against 12 strains of Gram-negative bacteria and 6 strains of Gram-positive bacteria were determined after 22 hours of incubation using an agar dilution method as described in example 2 (cf. notably section "2.2 Materials and methods).

The 18 bacteria strains tested for the purposes of the present example are identical to those tested in example 6.

9.2 Results

The results obtained are presented in Table 5 below

TABLE 5

Minimum inhibitory concentrations of antimicrobial compounds I and J against various bacteria species

| Species | Strain reference | Minimum inhibitory concentration (MIC) of compound I (µg/mL) | Minimum inhibitory concentration (MIC) of compound J (µg/mL) |
|---|---|---|---|
| *Acinetobacter baumannii* | ATCC 19606 | >8 | >8 |
| *Burkholderia cepacia* | ATCC 25416 | >8 | >8 |
| *Enterobacter cloacae* | NCTC 11936 | >8 | >8 |
| *Escherichia coli* | NCTC 10418 | 1 | 2 |
| *Escherichia coli* | NCTC 12241 | 1 | 2 |
| *Klebsiella pneumoniae* | NCTC 9528 | 0.25 | 0.5 |
| *Providencia rettgeri* | NCTC 7475 | >8 | >8 |

TABLE 5-continued

Minimum inhibitory concentrations of antimicrobial compounds I and J against various bacteria species

| Species | Strain reference | Minimum inhibitory concentration (MIC) of compound I (µg/mL) | Minimum inhibitory concentration (MIC) of compound J (µg/mL) |
|---|---|---|---|
| Pseudomonas aeruginosa | NCTC 10662 | >8 | >8 |
| Salmonella Typhimurium | NCTC 74 | >8 | >8 |
| Salmonella Enteritidis | NCTC 6676 | >8 | >8 |
| Serratia marcescens | NCTC 10211 | 0.25 | 0.5 |
| Yersinia enterocolitica | NCTC 11176 | 0.125 | 0.5 |
| Enterococcus faecalis | NCTC 775 | 0.063 | 0.125 |
| Enterococcus faecium | NCTC 7171 | 1 | 4 |
| Listeria monocytogenes | NCTC 11994 | >8 | >8 |
| Staphylococci epidermidis | NCTC 11047 | 1 | 2 |
| Staphylococcus aureus | NCTC 6571 | 1 | 1 |
| Staphylococcus aureus (SARM) | NCTC 11939 | >8 | >8 |

According to the data presented in table 5 above, it clearly appears that compounds I and J are strongly inhibiting against the tested strains of certain Gram-negative bacteria species and certain Gram-positive bacteria species, notably concerning *Escherichia coli, Klebsiella pneumoniae, Serratia marcescens, Yersinia enterocolitica, Enterococcus faecalis*, and less inhibiting against other Gram-negative and Gram-positive bacteria species, notably with regard to *Acinetobacter baumannii, Burkholderia cepacia, Pseudomonas aeruginosa, Salmonella typhimurium, Salmonella enteritidis, Listeria monocytogenes*.

BIBLIOGRAPHIC REFERENCES

[1] Rao J, Lahiri J, Weis R M, Whitesides G M. 2000. Design, synthesis, and characterization of a high-affinity trivalent system derived from vancomycin and L-Lys-D-Ala-D-Ala. J. Am. Chem. Soc. 122:2698-2710.

[2] Kametani T, Suzuki Y, Kigasawa K, Hiiragi M, Wakisaka K, Sugi H, Tanigawa K, Fukawa K, Irino O, Saita O, Yamabe S. 1982. Studies on the synthesis of chemotherapeutics. Part XIII. Synthesis and biological studies on phosphonopeptides having alkyl-, phenyl-, and heterocyclic substituents. Heterocycles 18:295-319.

[3] J. Bacteriol. 1984, 160(1), 122-130 Gibson et al

[4] Cheung et al, Chloroalanyl and Propargylglycyl Diperptides. Suicide Substrate Containing Antibacterials. J. Med. Chem. 1983, 26, 1733-1741

[5] Cheung K S, Boisvert W, Lerner S A, Johnston M. 1986. Chloroalanyl antibiotic peptides: antagonism of their antimicrobial effects by L-alanine and L-alanyl peptides in gram-negative bacteria. J. Med. Chem. 29:2060-2068.

[6] Atherton et al., Synthesis and Structure-Activity Relationships of Antibacterial Phosphonopeptides Incorporating (1-Aminoethyl)phosphonic Acid and (Aminomethyl)phosphonic Acid, Chemistry Department, Roche Products Limited, 1984

[7] Arfin et al., Inhibition of Growth of *Salmonella typhimurium* and of Threonine Deaminase and Transamine B by g-Chloroalanine

[8] Orenga et al., 2009; J. Microbiol. Methods; 79(2:139-55)

[9] Lavielle, S.; Ling, N. C.; Saltman, R.; Guillemn, R. C. *Carbohydrate Research*, 1981, 89(2), 229

[10] Nakata, T.; Nakatani, M.; Takahashi, M.; Okai, J.; Kawaoka, Y.; Kouge, K.; Okai, H. Bulletin of Chemical Society of Japan, 1996, 69(4), 1099

[11] Doctoral thesis of Varadi, L., University of Sunderland, 2012

[12] Kudzin, Z. H.; Stec, W. J. *Synthesis*, 1978, 469.

[13] Boduszek, B.; Soroka, M. *Polish Journal of Chemistry*, 2002, 76(8), 1105

[14] Kudzin, Z. H.; Luczak, J. *Synthesis*, 1995, 1995(5), 509.

[15] Yuan, C.; Xu, C.; Zhang, Y. *Tetrahedron*, 2003, 59(32), 6095

[16] Andrews J M. 2001. Determination of minimum inhibitory concentrations. J. Antimicrob. Chemother. 48 Suppl 1:5-16.

[17] Atherton F R, Hall M J, Hassall C H, Lambert R W, Ringrose P S. 1979. Phosphonopeptides as antibacterial agents: rationale, chemistry, and structure-activity relationships. Antimicrob. Agents Chemother. 15:677-683.

The invention claimed is:

1. An antimicrobial compound of formula (I):

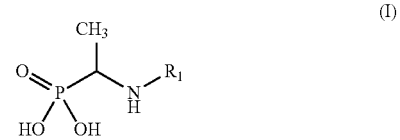

(I)

or a salt thereof,
wherein $R_1$ is:
a peptide part P1 consisting of a linear sequence of one to five amino acid residues, wherein at least one of the amino acid residues is a β-chloroalanine residue; or
a peptide part P2 of formula (II):

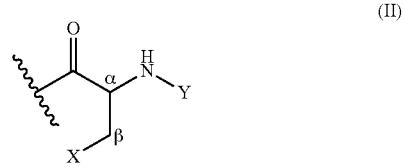

(II)

wherein X is hydrogen or chlorine, and
Y is hydrogen or a linear sequence of one to four amino acid residues; and
wherein if X is hydrogen, Y is not hydrogen and an alanine residue is not in the N-terminal position of the linear amino acid sequence or bound to another amino acid residue via a peptide bond between the α amino function of the alanine residue and the α carboxylic acid function of another amino acid residue.

2. The antimicrobial compound of claim 1, wherein at least one of the amino acid residues of the linear sequence of one to four amino acid residues Y is selected from a β-chloroalanine residue, a norvaline residue, and a methionine residue.

3. The antimicrobial compound of claim 1, wherein the β-chloroalanine residue is a β-chloro-L-alanine residue.

4. The antimicrobial compound of claim 2, wherein the β-chloroalanine residue is a β-chloro-L-alanine residue.

5. The antimicrobial compound of claim 2, wherein the norvaline residue is a L-norvaline residue.

6. The antimicrobial compound of claim 2, wherein the methionine residue is a L-methionine residue.

7. The antimicrobial compound of claim 1, wherein $R_1$ is represented by the general formula (III):

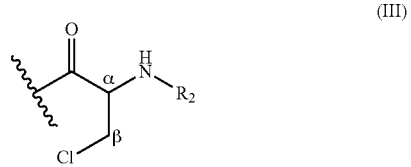

wherein $R_2$ is hydrogen or a linear sequence of one to four amino acid residues.

8. The antimicrobial compound of claim 7, wherein at least one of the amino acid residues is selected from a β-chloroalanine residue, a norvaline residue, and a methionine residue.

9. The antimicrobial compound of claim 8, wherein the β-chloroalanine residue is a β-chloro-L-alanine residue.

10. The antimicrobial compound of claim 8, wherein the norvaline residue is a L-norvaline residue.

11. The antimicrobial compound of claim 8, wherein the methionine residue is a L-methionine residue.

12. The antimicrobial compound of claim 1, wherein $R_1$ is represented by the general formula (IV):

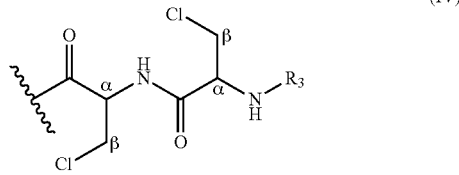

wherein $R_3$ is hydrogen or a linear sequence of one to three amino acid residues.

13. The antimicrobial compound of claim 12, wherein at least one of the amino acid residues is a β-chloroalanine residue.

14. The antimicrobial compound of claim 13, wherein the β-chloroalanine residue is a β-chloro-L-alanine residue.

15. The antimicrobial compound of claim 1, wherein $R_1$ is a linear chain of two or three amino acid residues.

16. The antimicrobial compound of claim 15, wherein $R_1$ is a linear chain of two amino acid residues.

17. The antimicrobial compound of claim 1, wherein the amino acid residue(s) is/are selected from the group consisting of: glycine, sarcosine, β-chloro-L-alanine, β-chloro-D-alanine, D/L-alanine, D/L-arginine, D/L-asparagine, D/L-aspartic acid, D/L-cysteine, D/L-glutamic acid, D/L-gamma-glutamic acid, D/L-glutamine, D/L-histidine, D/L-isoleucine, D/L-leucine, D/L-lysine, D/L-methionine, D/L-norvaline, D/L-phenylalanine, D/L-proline, D/L-pyroglutamic acid, D/L-serine, D/L-threonine, D/L-tryptophan, D/L-tyrosine, and D/L-valine.

18. The antimicrobial compound of claim 17, wherein the amino acid residue(s) is/are selected from β-chloro-L-alanine, L-alanine, L-arginine, L-asparagine, L-aspartic acid, L-cysteine, L-glutamic acid, L-gamma-glutamic acid, L-glutamine, L-histidine, L-isoleucine, L-leucine, L-lysine, L-methionine, L-norvaline, L-phenylalanine, L-proline, L-pyroglutamic acid, L-serine, L-threonine, L-tryptophan, L-tyrosine, and L-valine.

19. The antimicrobial compound of claim 17, wherein the amino acid residue(s) is/are selected from β-chloro-L-alanine, β-chloro-D-alanine, D/L-alanine, D/L-methionine, D/L-norvaline, and D/L-valine.

20. The antimicrobial compound of claim 1, wherein $R_1$ is the peptide part P2 and X is hydrogen.

21. The antimicrobial compound of claim 20, wherein Y is one amino acid residue selected from: glycine, sarcosine, β-chloro-L-alanine, β-chloro-D-alanine, D/L-arginine, D/L-asparagine, D/L-aspartic acid, D/L-cysteine, D/L-glutamic acid, D/L-gamma-glutamic acid, D/L-glutamine, D/L-histidine, D/L-isoleucine, D/L-leucine, D/L-lysine, D/L-methionine, D/L-norvaline, D/L-phenylalanine, D/L-proline, D/L-pyroglutamic acid, D/L-serine, D/L-threonine, D/L-tryptophan, D/L-tyrosine, and D/L-valine.

22. The antimicrobial compound of claim 21, wherein the amino acid residue is selected from a L-methionine residue and a L-norvaline residue.

23. The antimicrobial compound of claim 1, wherein the antimicrobial compound is selected from:
β-chloro-L-alanyl-D/L-1-aminoethylphosphonic acid;
β-chloro-L-alanyl-β-chloro-L-alanyl-D/L-1-aminoethylphosphonic acid;
L-norvalinyl-β-chloro-L-alanyl-D/L-1-aminoethylphosphonic acid;
L-methionyl-β-chloro-L-alanyl-D/L-1-aminoethylphosphonic acid;
L-norvalinyl-L-alanyl-D/L-1-aminoethylphosphonic acid; and
L-methionyl-L-alanyl-D/L-1-aminoethylphosphonic acid.

24. The antimicrobial compound of claim 1, wherein the antimicrobial compound is selected from:
β-chloro-L-alanyl-L-1-aminoethylphosphonic acid;
β-chloro-L-alanyl-β-chloro-L-alanyl-L-1-aminoethylphosphonic acid;
L-norvalinyl-β-chloro-L-alanyl-L-1-aminoethylphosphonic acid;
L-methionyl-β-chloro-L-alanyl-L-1-aminoethylphosphonic acid;
L-norvalinyl-L-alanyl-L-1-aminoethylphosphonic acid; and
L-methionyl-L-alanyl-L-1-aminoethylphosphonic acid.

25. The antimicrobial compound of claim 1, wherein the antimicrobial compound is selected from:
β-chloro-L-alanyl-L-1-aminoethylphosphonic acid; and
β-chloro-L-alanyl-β-chloro-L-alanyl-L-1-aminoethylphosphonic acid.

26. The antimicrobial compound of claim 1, wherein the amino function of the N-terminal amino acid residue of P1 or P2 is protected by a protecting group selected from: a tertiobutylocarbonyl group, a 9-fluorenylmethoxycarbonyl group and a benzyloxycarbonyl group.

27. A reaction medium comprising at least one antimicrobial compound of claim 1.

28. The reaction medium of claim 27, wherein the final concentration of the antimicrobial compound is between 0.002 mg/L and 1024.0 mg/L.

29. The reaction medium of claim 28, wherein the final concentration of the antimicrobial compound is between 0.003 mg/L and 32.0 mg/L.

30. The reaction medium of claim 29, wherein the final concentration of the antimicrobial compound is between 0.2 mg/L and 8.0 mg/L.

31. The reaction medium of claim 30, wherein the final concentration of the antimicrobial compound is between 0.2 and 2.0 mg/L.

32. The reaction medium of claim 27, wherein the reaction medium further comprises:
at least one target microorganism.

33. The reaction medium of claim 32, wherein the at least one target microorganism is a microorganism from a sample of industrial or clinical origin.

34. The reaction medium of claim 33, wherein the antimicrobial compound is a selective agent, and wherein the selective agent is capable of inhibiting the survival and/or growth of non-target microorganism(s).

35. The reaction medium of claim 34, further comprising at least one growth nutrient, wherein the nutrient is a nutrient that enables the growth of the at least one target microorganism.

36. The reaction medium of claim 34, wherein the reaction medium further comprises an enzyme substrate, wherein the enzyme substrate is specific to an enzyme activity of the at least one target microorganism.

37. The reaction medium of claim 34, wherein the selective agent is selected from:
β-chloro-L-alanyl-L-1-aminoethylphosphonic acid; and
β-chloro-L-alanyl-β-chloro-L-alanyl-L-1-aminoethylphosphonic acid; or
a mixture thereof.

38. The reaction medium of claim 34, wherein the target microorganism is selected from:

at least one Gram-negative target microorganism belonging to the genus *Salmonella*, the genus *Acinetobacter*, or the genus *Pseudomonas*; and
at least one Gram-positive target microorganism, belonging to the genus *Listeria* or the genus *Streptococcus*.

39. The reaction medium of claim 35, wherein the reaction medium further comprises:
a buffer;
at least one chromogenic marker at a concentration of between 0.05 and 15.0 g/L; and
agar at a concentration of between 9.0 and 28.0 g/L, wherein the at least one target microorganism belongs to the genus *Salmonella*, wherein the at least one nutrient agent is a peptone at a concentration of between 0.2 and 30.0 g/L, and wherein the selective agent is at a concentration of between 0.002 and 1024.0 mg/L.

40. The reaction medium of claim 34, wherein the non-target microorganism(s) belong to a genus selected from:
*Enterobacter*;
*Escherichia*;
*Klebsiella*;
*Serratia*;
*Yersinia*;
*Enterococcus*; and
*Staphylococcus*.

41. The reaction medium of claim 40, wherein the non-target microorganism(s) is/are resistant to at least one conventional antibacterial.

42. A method for detecting, identifying or counting at least one target microorganism from a sample of industrial or clinical origin, the method comprising:
a) seeding the reaction medium of claim 33;
b) incubating the reaction medium for a period of time sufficient to detect, identify or count the at least one target microorganism; and
c) detecting, identifying or counting colonies formed by the at least one target microorganism.

43. A medication for human or veterinary use comprising the antimicrobial compound of claim 1.

44. A method of treating microbial infections comprising administering the medication of claim 43 to a human or animal in need thereof.

* * * * *